US008338173B2

(12) United States Patent
Moser et al.

(10) Patent No.: US 8,338,173 B2
(45) Date of Patent: *Dec. 25, 2012

(54) PREPARATION OF ANTIGEN-PRESENTING HUMAN γδ T CELLS AND USE IN IMMUNOTHERAPY

(75) Inventors: Bernhard Moser, Utzenstorf (CH); Marlene Brandes Kuchen, Bethesda, MD (US)

(73) Assignee: University College Cardiff Consultants Limited, Cardiff (GB)

( * ) Notice: Subject to any disclaimer, the term of this patent is extended or adjusted under 35 U.S.C. 154(b) by 258 days.

This patent is subject to a terminal disclaimer.

(21) Appl. No.: 12/271,576

(22) Filed: Nov. 14, 2008

(65) Prior Publication Data

US 2009/0130074 A1 May 21, 2009

Related U.S. Application Data

(63) Continuation-in-part of application No. 11/573,912, filed as application No. PCT/CH2005/000469 on Aug. 11, 2005, now Pat. No. 8,153,426.

(51) Int. Cl.
*C12N 5/071* (2010.01)
*C12N 5/0783* (2010.01)
*C12N 15/00* (2006.01)

(52) U.S. Cl. ............. 435/347; 435/372.3; 435/373; 435/374

(58) Field of Classification Search .......... None
See application file for complete search history.

(56) References Cited

U.S. PATENT DOCUMENTS

| | | | |
|---|---|---|---|
| 5,788,963 | A | 8/1998 | Murphy et al. |
| 6,274,378 | B1 * | 8/2001 | Steinman et al. ............ 435/377 |
| 2005/0009008 | A1 * | 1/2005 | Robinson et al. ............ 435/5 |
| 2005/0196385 | A1 | 9/2005 | Romagne et al. |
| 2006/0194755 | A1 | 8/2006 | Romagne et al. |
| 2008/0075732 | A1 | 3/2008 | Moser |
| 2009/0208517 | A1 | 8/2009 | Moser |

FOREIGN PATENT DOCUMENTS

| | | | |
|---|---|---|---|
| WO | WO2004085635 | * | 3/2004 |
| WO | WO 2006/017954 | | 2/2006 |

OTHER PUBLICATIONS

Das et al (Immunity, 2001, vol. 15, pp. 83-93).*
Hintz et al (FEBS Letters, 2001, vol. 509, pp. 317-322).*
Moser et al (Trends in Immunology, Mar. 2006, vol. 27, pp. 112-118).*
Marlene Brandes, Katharina Willimann, Alois B. Lang, Ki-Hoan Nam, Chenggang Jin, Michael B. Brenner, Craig T. Morita & Bernhard Moser, Flexible Migration Program Regulates γδ T Cell Involvement in Humoral Immunity, Blood, vol. 102, No. 10, Nov. 15, 2003, pp. 3693-3701, The American Society of Hermatology.
Robert L. Modlin & Peter A. Sieling, Now Presenting γδ T Cells, Perspectives Immunology, vol. 309, Science, Jul. 8, 2005, pp. 252-268, Science Magazine, www.sciencemag.org.
Marlene Brandes, Katharina Willimann & Bernhard Moser, Professional Antigen-Presentation Function by Human γδ T Cells, Research Article, vol. 309, Science, Jul. 8, 2005, pp. 264-268, Science Magazine, www.sciencemag.org.
Nadia Caccamo, Luca Battistini, Marc Bonneville, Fabrizio Poccia, Jean Jacques Fournie, Serena Meraviglia, Giovanna Borsellino, Richard A. Kroczek, Carmela La Mendola, Emmanuel Scotet, Francesco Dieli & Alfredo Salerno, CXCR5 Identifies a Subset of Vγ9Vδ2 T Cells Which Secrete IL-4 and IL-10 and Help B Cells for Antibody Production, The Journal of Immunology, vol. 177, 2006, pp. 5290-5295, The American Association of Immunologists, Inc.
U.S. Appl. No. 12/433,030 Office Action dated Oct. 18, 2011.
U.S. Appl. No. 12/433,030 Office Action dated Apr. 27, 2011.
U.S. Appl. No. 11/573,912 Office Action dated Oct. 14, 2011.
U.S. Appl. No. 11/573,912 Office Action dated Jun. 3, 2010.
U.S. Appl. No. 11/573,912 Office Action dated Jan. 6, 2010.
U.S. Appl. No. 11/573,912 Office Action dated May 13, 2009.
U.S. Appl. No. 11/573,912 Office Action dated Nov. 17, 2008.
Bieback et al (Journal of General Virology, 2003, vol. 85, pt. 5, pp. 1179-1188).
Malkovska et al (Cancer Research, 1992, vol. 52, pp. 5610-5616).
Gossman et al (J. Med Chem, 2002, vol. 45, pp. 4868-4874).
Abstract of Wheeler (Salud publica de Mexico, (Jul.-Aug. 1997) 39 (4) 283-7).
Efferson et al (Anticancer Research, 2005, vol. 25, pp. 715-724).
Bachman et al ( Journal of Immunology, 2005, vol. 175, pp. 4677-4685).
Burgoff and Kurts (Current Opinion in Immunology, 2008, vol. 20, pp. 89-98).
Antonio Lanzavecchia, Eddy Roosnek, Tim Gregory, Phillip Berman & Sergio Abrignani, Letters to Nature, Nature, vol. 334, Aug. 11, 1988, pp. 530-532, Department of Immunology, Basel, Switzerland.
Antonio Lanzavecchia, Receptor-Mediated Antigen Uptake and Its Effect on Antigen Presentation to Class II-Restricted T Lymphocytes, 1990, pp. 773-793, Basel Institute for Immunology, Basel Switzerland. Annual Reviews, www.annualreviews.org/aronline. ISBN: 0732-0582/90/0410-0773$02.00.

(Continued)

*Primary Examiner* — Karen Canella
(74) *Attorney, Agent, or Firm* — King & Schickli, PLLC

(57) ABSTRACT

Cytotoxic αβ T cells form an essential component in immunity to infections and tumors, and are also implicated in host defense against these challenges. The present disclosure demonstrates the ability of activated γδ T cells to cross-present exogenous antigens to CD8+ αβ T cells, a process previously thought to be mediated best by dendritic cells. In particular, the present disclosure provides a method for cross-presentation of antigen derived from tumor cell or microbial organisms such as viruses, bacteria, yeasts, parasites, and the like, or from cells infected with such organisms, to a CD8+ αβ T cell. Still further, the present disclosure provides a method for treatment of a tumor or a chronic or recurrent infectious disease, comprising delivering an antigen-presenting autologous γδ T cell population above into a patient requiring such treatment. Still yet further, a method is described for preparing a peptide-specific effector T cell.

20 Claims, 30 Drawing Sheets

OTHER PUBLICATIONS

Craig T. Morita, Evan M. Beckman, Jack F. Bukowski, Yoshimase Tanaka, Hamid Band, Barry R. Bloom, David E. Golan & Michael B. Brenner, Direct Presentation of Nonpeptide Prenyl Pyrophosphate Antigens to Human yoT Cells, Immunity, vol. 3, Oct. 1995, pp. 495-507, Cell Press.

Robert A. Collins, Dirk Werling, Sara E. Duggan, A. Patricia Bland, Keith R. Parsons & Christopher J. Howard, yoT Cells Present Antigen to CD4 aB T Cells, Journal of Leukocyte Biology, vol. 63, Jun. 1998, pp. 707-714, Division of Immunology and Pathology, Institute for Animal Health, Compton, Newbury Berks, UK.

H.-H. Takamatsu, M.S. Denyer & T.E. Wileman, A Sub-Population of Circulating Porcine yo T Cells Can Act as Professional Antigen Presenting Cells, vol. 87, pp. 2223-224, Elsevier Science, Insititute for Animal Health, Veterinary Immunology and Immunopathology, Pirbright Laboratory, Woking, Surry, UK, 2000.

* cited by examiner

A

US 8,338,173 B2

PREPARATION OF ANTIGEN-PRESENTING HUMAN γδ T CELLS AND USE IN IMMUNOTHERAPY

This application is a continuation-in-part of U.S. patent application Ser. No. 11/573,912, filed on Feb. 19, 2007, now U.S. Pat. No. 8,153,426 which in turn is a national stage application of International Patent Application No. PCT/CH05/00469, filed on Aug. 11, 2005, the entirety of the disclosures of each of which are incorporated herein by reference.

TECHNICAL FIELD

The invention relates to a method for the preparation of efficient antigen-presenting human γδ T cells, to the γδ T cells prepared by such a method, and to their use in immunotherapy, antigen identification and diagnosis of immune competence. In particular, the invention relates to cross-presentation of tumor-, bacterial-, or virus-derived antigens to human $CD8^+$ αβ T cells.

BACKGROUND OF THE INVENTION

The Cellular Components of the Adaptive Immune System

The cellular components of the immune system are divided into the cells of the innate immune system and the cells of the adaptive (acquired or specific) immune system. Cells of the innate immune system include (among others) monocytes, granulocytes, natural killer cells in peripheral blood, and mast cells, macrophages and dendritic cells (DCs) in extravascular compartments including peripheral tissues, such as skin, airways, gastrointestinal and urogenital tracts, internal organs as well as secondary lymphoid tissues, such as spleen, lymph nodes (LNs) and Peyer's patches (PPs). The main functions of innate cells are a) provision of immediate protection by neutralizing and limiting dissemination of infectious particles, and by tumor cell clearing, b) immune surveillance of healthy tissues, and c) initiation of adaptive immune responses. Cells of the adaptive immune system include lymphocytes, such as T and B cells. They are distinguished from innate cells by the presence of clonotypic cell surface antigen receptors, referred to as T cell antigen receptor (TCR) and B cell antigen receptor (BCR). Each individual lymphocyte carries a distinct TCR or BCR that recognizes a particular antigen. The specificity of antigen recognition is determined by rearrangement of multiple variable TCR or BCR gene segments during T and B cell development and during antigen affinity maturation at the time of effector T and B cell generation. Naïve, antigen-inexperienced T cells in peripheral blood differ from each other in the antigen-selectivity of their TCRs, and individual naïve T cells become expanded in response to immune activation by agents containing the antigen they are specific for. Consequently, during adaptive immune responses a set of naïve T cells with TCRs specific for the potentially infectious agent becomes expanded via cell proliferation, and develops into a) effector T cells for immediate participation in the defence against the potentially infectious agent, and into b) memory T cells for long-lasting protection against this particular potentially infectious agent. Effector T cells are short-lived, i.e. disappear during the resolution phase of the immune response, whereas the memory T cells are long-lived and are divided into memory T cell subsets according to their primary tissue residence or preferential recirculation routes (Moser et al., 2004). T cells are further divided into αβ T cells and γδ T cells (see below) according to the composition of the heterodimeric TCRs; αβ-TCRs are composed of α- and β-protein chains, and γδ-TCRs are composed of γ- and δ-protein chains. The majority (>80%) of all $CD3^+$ T cells in a normal, healthy person are αβ T cells. TCRs are associated with the invariant CD3 molecule that distinguishes T cells from B cells and all other types of immune cells. The majority of αβ T cells recognize the antigen in a so-called major histocompatibility complex (MHC) molecules-restricted fashion. This is in contrast to BCRs in B cells that directly bind the nominal antigen in a MHC-non-restricted fashion. The term MHC-restriction refers to the mode by which the TCRs recognize their antigens and involves the presentation of antigenic peptides together with MHC molecules, as so-called MHC-peptide complexes, on antigen-presenting cells (APCs), including DCs (see below). There are two major classes of MHC molecules, MHC class I (MHC-I) and MHC class II (MHC-I), which trigger the TCRs of the two major subsets of αβ T cells, the $CD8^+$ αβ T cells and $CD4^+$ αβ T cells. The TCRs on $CD4^+$ αβ T cells recognize MHC-II-peptide complexes whereas the TCRs on $CD8^+$ αβ T cells recognize MHC-I-peptide complexes. In striking contrast, the major subset of γδ T cells in human peripheral blood does not express CD4 or CD8 and its TCRs do not require MHC-restriction for antigen recognition (see below).

γδ T Cells

γδ T cells are a distinct subset of $CD3^+$ T cells featuring TCRs that are encoded by Vγ- and Vδ-gene segments (Morita et al., 2000; Carding and Egan, 2002). They are further divided according to their primary residence in blood or tissues, the protein chain composition of their VγVδ-TCRs and their antigen selectivity: In humans, $Vδ1^+$-TCR chain expressing γδ T cells ($Vδ1^+$ T cells) predominate in epithelial or epithelia-associated/mucosal tissues of the skin, airways, digestive and urogenital tracts, and several internal organs, and constitute a minor fraction (<20%) of γδ T cells in peripheral blood. The TCRs of $Vδ1^+$ T cells recognize lipid antigens presented by MHC-related CD1 molecules. Further, $Vδ1^+$ T cells respond to stress-associated proteins, including MHC-related molecules MICA and MICB, and heat-shock proteins. They are thought to provide a first-line defence against tumors and otherwise stressed cells and, in addition, are thought to contribute to wound healing, tissue repair and autoimmunity. In human peripheral blood of healthy individuals γδ T cells make up 2-10% of total $CD3^+$ T cells, and the majority (>80%) of peripheral blood γδ T cells are $Vγ2Vδ2^+$-TCR chain-expressing γδ T cells ($Vγ2Vδ2^+$ γδ T cells) (Morita et al., 2000; Carding and Egan, 2002).

The TCRs of $Vγ2Vδ2^+$ γδ T cells are highly selective for small non-peptide antigens of mostly microbial origin and do not require antigen presentation by classical MHC molecules, as is typical for peptide-selective αβ T cells (see above). $Vγ2Vδ2^+$ γδ T cell antigens include prenyl-pyrophosphates, such as isopentenyl pyrophosphate (IPP), alkyl-amines and metabolites of a newly discovered isoprenold biosynthesis pathway found in most human microbial pathogens and commensal bacteria [for example, (E)-4-hydroxy-3-methyl-but-2-enyl pyrophosphate (HMB-PP); Morita et al., 2000; Eberl et al., 2003)]. Some of these $Vγ2Vδ2^+$ γδ T cell antigens, such as IPP and alkyl amines, are also released by necrotic tissue cells. The homologue of human $Vγ2Vδ2^+$ γδ T cells, carrying homologous VγVδ-TCRs with selectivity for small non-peptide antigens of microbial origin, does also exist in higher primates, such as macaques, but does not exist in rodents, including mice and rabbits. It is not clear why the presence of $Vγ2Vδ2^+$ γδ T cells is limited to higher primates but it could be speculated that they evolved to satisfy the special need for cellular protection against a distinct, species-specific selection of microbes. $Vγ2Vδ2^+$ γδ T cells rapidly expand in response to the model antigen IPP or microbial extracts in vitro during tissue culture of peripheral blood Vγ2Vδ2+ γδ T cells, or in vivo during vaccination experiments in higher primates, such as macaques (Chen and Letvin, 2003). Also, microbial infections in humans are frequently associated with tremendous expansion of peripheral blood Vγ2Vδ2+ γδ T cells, reaching levels as high as >60% of total peripheral blood CD3+ T cells. These findings support the notion that human Vγ2Vδ2+ γδ T cells play an important role in immune processes during microbial infections (Morita et al., 2000; Carding and Egan, 2002; Chen and Letvin, 2003). Their unique selectivity for non-peptide antigens that are commonly found in microbes, including pathogens and commensal bacteria, suggest that the TCRs in Vγ2Vδ2+ γδ T cells fulfil a similar function as toll-like receptors (TLR) that trigger activation and maturation of DCs and other APCs in response to diverse ligands of microbial origin.

γδ T cells contribute to pathogen elimination by rapid secretion of chemokines that initiate the recruitment of cells of the innate immune system and proinflammatory cytokines (TNF-α, IFN-γ) that stimulate antigen-presenting cells and enhance bacterial killing by granulocytes, macrophages and NK cells (Morita et al., 2000; Carding and Egan, 2002; Chen and Letvin, 2003). They also express natural killer cell receptors for killing of infected or neoplastic tissue cells. These findings support the notion that γδ T cells primarily fulfil innate functions, although secretion of pro-inflammatory cytokines, such as TNF-α, is known also to contribute to local adaptive immune responses. On the other hand, evidence for direct involvement of γδ T cells in adaptive immune responses is not clear-cut. For instance, it is reported that CD1-restricted T cells induce maturing in DCs that present CD1-lipid complexes. Also, studies in mice demonstrated a not further explained role for γδ T cells in B cell responses, and human γδ T cells were shown to regulate B cell responses during in vitro co-cultures (Brandes et al., 2003). Finally, studies in macaques demonstrated that Vγ2Vδ2+γδ T cells were able to mount in vivo memory responses to *Mycobacterium bovis* antigens (Chen and Letvin, 2003). Collectively, these findings provide evidence that γδ T cells are able to interact with cells of the adaptive immune system, such as B cells and DCs. Most of these immunomodulatory functions were attributed to cytokine production by γδ T cells or were left unexplained. Importantly, none of these findings support a role for γδ T cells in antigen presentation.

Lymphocyte function is Intimately related to the lymphocyte migration potential, as defined by the expression of chemokine receptors and adhesion molecules (Moser et al., 2004). Accordingly, αβ T cells are divided into a) naïve T cells expressing the LN-homing chemokine receptor CCR7 but lacking receptors for inflammatory chemokines, b) short-lived effector T cells bearing distinct combinations of chemokine receptors and inducible adhesion molecules that mirror the inflammatory conditions at the site of infection, and c) three subsets of resting, long-lived memory T cells. The distinction of T cell subsets according to their migration potential, i.e. their expression profile of cell surface chemokine receptors and adhesion molecules, correlates well with their state of differentiation and potential function in immune processes. Of note, the "profiling" of chemokine receptors and adhesion molecules is widely used for phenotypic and functional definition of leukocyte subsets, including DCs, and T and B cells (Moser et al., 2004).

The migration properties of human peripheral blood γδ T cells differ strikingly from those of human peripheral blood αβ T cells (Brandes et al., 2003). Most notably, the majority (>80%) of Vγ2Vδ2+ γδ T cells (hereafter referred to as "γδ T cells") lacks CCR7 and, thus, is excluded from secondary lymphoid tissues, but features an inflammatory migration profile (Brandes et al., 2003). In clear contrast, the majority (>70%) of αβ T cells in peripheral blood express CCR7, which agrees with their continuous recirculation through secondary lymphoid tissues (spleen, LNs, PPs) where they scan APCs for the presence of the appropriate MHC-peptide complexes. In case of ongoing adaptive immune responses, a selection of αβ T cells becomes activated during contact with APCs presenting their cognate antigens and differentiates into CCR7-negative effector cells with inflammatory homing potential. By contrast, peripheral blood γδ T cells feature an inflammatory migration program for their immediate tissue mobilization in response to inflammatory chemokines produced at sites of infection. Upon activation, e.g. in response to microbial extract antigens or defined small non-peptide antigens (such as IPP), the migration profile in γδ T cells rapidly switches from an inflammatory to a LN-homing phenotype, as evidenced by downmodulation of receptors for inflammatory chemokines and induction of CCR7 (Brandes et al., 2003). By contrast to αβ T cells, γδ T cells are relatively rare in LNs, which agrees with their distinct mode of activation that is fully independent of MHC-restricting APCs present at these locations (Brandes et al., 2003). The frequency of γδ T cells is increased in disease-associated LNs (notably in germinal centers), suggesting that γδ T cells may contribute to the initiation of humoral (antibody) responses and possibly other adaptive immune processes.

Collectively, migration characteristics of human γδ T cells and their occasional presence in LNs suggest a role for these cells in the initiation of adaptive immune responses. However, this role is not further defined and there is no evidence that γδ T cells may function as antigen-presenting cells.

A distinguishing feature of γδ T cells is that their TCRs are selective for conserved non-peptide compounds of microbial or tumor cell origin, which are recognized in a MHC-independent fashion. The most relevant ligands appear to be (E)-4-hydroxy-3-methyl-but-2-enyl pyrophosphate (HMB-PP), an intermediate of the non-mevalonate pathway in numerous microbes, and isopentenyl pyrophosphate (IPP), the common end product of both the classical and the non-mevalonate pathway (15, 16). The level of peripheral blood Vγ9Vδ2+ T cells in patients suffering from numerous infections, as exemplified by HMB-PP-producing *M. tuberculosis* and malaria parasites, is highly elevated (15, 16). Vγ9Vδ2+ T cells are also expanded in patents with certain viral infections and show reactivity to tumors (17, 18). Collectively, TCRs in Vγ9Vδ2+ T cells resemble receptors for pathogen-associate molecular patterns found in professional APCs (19), which become rapidly engaged upon pathogen contact. Of note, this particular TCR selectivity is unique to γδ T cells in higher primates, including man, i.e. γδ T cells from standard laboratory animals do not respond to HMB-PP or IPP.

Activated Vγ9Vδ2+ T cells (termed γδ T-APCs) resemble mature dendritic cells (DCs) in their ability to trigger CD4+ αβ T cell responses (21, 22). However, reactivity to a broad range of pathogens, including intracellular bacteria and viruses, as well as tumors suggested a role for γδ T-APCs in induction of pathogen/tumor-specific CD8+ T effector cells. Here we have examined the ability of activated human Vγ9Vδ2+ T cells to cross-present soluble microbial and tumor antigens to autologous CD8+ αβ T cells.

Dendritic Cells (DCs)

DCs form a distinct class of leukocytes, are derived from hematopoietic progenitor cells in the bone marrow, and primarily reside in extravascular sites that include epithelial/mucosal tissues (skin, airways and gastrointestinal/urogenital tracts, among others) and secondary lymphoid tissues (spleen, LNs, PPs) (Banchereau and Steinman, 1998: Steinman et al., 2003; Banchereau et al., 2004). In peripheral blood, DCs or DC precursors make up less than 1% of mononuclear leukocytes. Distinct DC subsets differ in their tissue localization, as exemplified by interstitial DCs that primarily reside in soft tissues bordering epithelia, Langerhans cells (LCs) present in the epidermis and plasmacytoid DCs with homing preferences for LNs. These DC subsets are fully differentiated non-proliferating cells with a limited life-span of several days to several weeks, indicating that they are continuously replaced under steady-state conditions by bone marrow-derived precursors. By contrast, human memory T cells survive for many years and are maintained by means of steady-state (homeostatic) proliferation.

The principal function of tissue-resident DCs is the uptake and processing of local antigens, their relocation via afferent lymphatic vessels to draining LNs and the initiation of antigen-specific adaptive immune responses (Banchereau and Steinman, 1998; Steinman et al., 2003; Banchereau et al., 2004). DCs also induce tolerance when antigens are presented to T cells under tolerogenic conditions, i.e. in the absence of pro-inflammatory T cell co-stimulation. Similarly, antigen-presenting B cells have been shown to induce tolerance (Zhong et al., 1997). Break in the immunological tolerance against self-antigens is thought to be the frequent cause of autoimmune diseases and, thus, tolerogenic DCs presenting self-antigens are essential regulators of immune homeostasis. In healthy peripheral tissues DCs are present in their fully differentiated but "immature" state. Immature DCs express a set of receptors for inflammatory chemokines for quick recruitment to local infection, inflammation or tissue damage. They themselves are poorly immunogenic, i.e. are not capable of inducing primary adaptive immune responses. Instead they are experts in antigen uptake (by means of receptor-mediated endocytic or fluid phase pinocytic mechanisms), antigen processing and peptide loading onto intracellular MHC-I/II molecules and their cell surface presentation. Since immature DCs do not generally express the LN-homing receptor CCR7 it is not known at present how this type of DCs reaches the T cell areas in spleen, LNs and PPs. A multitude of maturation signals, including virus- or bacteria-derived stimuli that trigger toll-like receptors (TLRs), host cell-derived inflammatory mediators (interferon [IFN]-$\gamma$, tumor necrosis factor [TNF]-$\alpha$, interleukin [IL]-1, prostaglandin E2 [PGE2], tissue growth factors, among others), and T cell co-stimulatory molecules (CD40-ligand/CD154), induce DC "maturation" (Banchereau and Steinman, 1998; Steinman et al., 2003; Banchereau et al., 2004). During the early phase of DC maturation, DCs secrete high levels of inflammatory chemokines for augmentation of the inflammatory response via recruitment of additional immature DCs and cells of the innate immune system (monocytes, granulocytes, natural killer cells). Subsequently, the inflammatory migration program is gradually substituted by a LN-homing migration program characterized by substitution of receptors for inflammatory chemokines with CCR7. CCR7 is essential for efficient relocation of sensitized DCs from peripheral tissues to draining LNs in response to the two CCR7-selective chemokines ELC/CCL19 and SLC/CCL21 present on lymphatic vessels and in the T cell area of spleen, LNs and PPs. Thus, CCR7 expression marks mature or maturing DCs. In addition to LN-homing properties, mature DCs feature stable cell surface expression of MHC-I/II-peptide complexes in large numbers as well as diverse co-stimulatory molecules that are required for proper stimulation of naïve (antigen-inexperienced) $\alpha\beta$ T cells (Banchereau and Steinman, 1998; Steinman et al., 2003; Banchereau et al., 2004). DCs are also referred to as "professional" APCs because they are capable of stimulating naïve $\alpha\beta$ T cells during primary immune responses. Memory (antigen-experienced) T cells have a lower activation threshold and, thus, respond to less stringent stimulatory regimens. The functional duality of DCs that distinguishes between the two states of differentiation, a) immature, antigen-processing DCs in peripheral tissues and b) relocated mature, antigen-presenting and co-stimulating DCs in the tissue-draining LNs, is a hallmark of DC physiology and is tightly linked to local inflammation, infection or tissue damage. Finally, the outcome (quality and quantity) of the adaptive immune response is largely determined by the "mode" of response initiation. DCs are known to "instruct" naïve T cells within the T cell area of LNs and PPs about the type of immune response required for pathogen elimination (Banchereau and Steinman, 1998; Steinman et al., 2003; Banchereau et al., 2004). Accordingly, the inflammatory environment in the tissue directly influences DC maturation and, due to DC relocation, also determines T cell differentiation within draining LNs. Distinct effector fates of naïve T cell differentiation include specialized subsets of T helper cells (IFN-$\gamma$/TNF-$\alpha$-producing type 1 T helper [Th1] cells, IL-4/IL-5/IL-13-producing Th2 cells, among others), regulatory T cells and cytolytic T cells (CTLs). Effector T cells home to sites of inflammation, rapidly mount effector functions (cytokine secretion, lysis/killing of infected/tumor cells) and have a limited life-span. By contrast, memory T cells are the long-lived product of primary immunization and mount superior immune responses against recall antigens.

Immunity to many pathogens and tumors involves major histocompatibility complex class I (MHC I) restricted, cytotoxic $CD8^+$ $\alpha\beta$ T cells, which kill affected leukocytes and non-hematopoietic tissue cells (Doherty et al., 2000; Yewdell et al., 2005). Microbes and tumors frequently interfere with antigen processing or presentation and thus inhibit appropriate antigen-presenting cell (APC) function (Alcami, 2003); also, many microbes do not infect APCs. However, dendritic cells (DCs), the prototype professional APCs (4), can take up exogenous material derived from infected cells and tumors and direct these to intracellular compartments with access to the MHC I pathway, a process known as antigen "cross-presentation" (Yewdell et al., 2005; Cresswell et al., 2005; Rock et al., 2005; Villadangos et al., 2007). Such DCs can trigger expansion and differentiation of microbe/tumor-specific $CD8^+$ $\alpha\beta$ T cells. Antigen cross-presentation is conventionally thought to be restricted to DCs, such as interstitial DCs and $CD8^+$ DCs in the spleen of mice (den Haan et al., 2000; Stoitzner et al, 2006: Dudziak et al., 2007).

Dendritic Cells in Immunotherapy

DCs are "nature's adjuvant", i.e. constitute the most expert cellular system for induction of protective immune responses, and, therefore, are being developed for use in human immunotherapy (Fong and Engleman, 2000; Steinman et al., 2003; Schuler et al., 2003; Figdor et al., 2004). Potential applications include cancer therapy, vaccination against pathogens (such as human immunodeficiency virus [HIV]-1 and hepatitis C virus) and treatment of autoimmune diseases. Current DC therapy protocols include:
  1. Isolation and purification of DC precursors from patients' blood (bone marrow-derived $CD34^+$ hematopoietic precursors or peripheral blood $CD14^+$ or $CD11c^+$ cells).
  2. Generation of DCs during in vitro cell culture.
  3. In vitro antigen loading for peptide-presentation by mature DCs.

4. Treatment of patients with single or repeated injections of peptide-presenting DCs.

Currently, the application of DCs in immunotherapy faces several problems (Fong and Engleman, 2000; Steinman et al., 2003; Schuler et al., 2003: Figdor et al., 2004). In brief, DC precursors are scarce in peripheral blood and do not proliferate during in vitro culture, necessitating repeated manipulation with large blood samples from patients. DCs are functionally heterogeneous and may induce opposing or unwanted effects, e.g. immune suppression instead of effector T cell generation. Also, DCs are functionally instable and go through a preset sequence of irreversible differentiation steps ending in compromised ("exhausted") immune functions. This causes great difficulties in generating functionally homogeneous DC preparations by in vitro manipulations. Finally, the generation of peptide-presenting DCs for use in immunotherapy is technically demanding, time consuming and costly.

SUMMARY OF THE INVENTION

The present invention describes the simple isolation and in vitro preparation of antigen-presenting human γδ T cells and their use as efficient antigen-presenting cells (APCs) in immunotherapy. Similar to dendritic cells (DCs) in potency and efficacy, human γδ T cells process antigens and present antigenic peptides to αβ T cells and induce antigen-specific responses (proliferation and differentiation) in naïve αβ T cells. γδ T cells are relative frequent in peripheral blood (2-10% of CD3$^+$ T cells), are easily purified from peripheral blood by diverse simple techniques, acquire "maturation" status (expression of MHC-II, and essential adhesion and co-stimulatory molecules) within 1 day of in vitro culture under simple stimulatory conditions, maintain efficient antigen-presenting functions over 7 days or more of in vitro culture and induce strong primary and secondary T helper cell responses. Furthermore, γδ T cells are readily expanded during in vitro culture for storage and later use.

The invention relates to a method for the preparation of efficient antigen-presenting human γδ T cells comprising selecting γδ T cells out of human peripheral blood mononuclear cells, treating the selected cells with a stimulus for induction of antigen-presenting functions, and applying the antigen to these cells (either before, during or after induction of antigen-presenting functions), to the efficient antigen-presenting human γδ T cells prepared by such a method, their use in immunotherapy and in the manufacture of a medicament for use in immunotherapy, to a method of treatment of tumors or chronic or recurrent infectious diseases with such efficient antigen-presenting human γδ T cells, to a method of vaccination against tumors or agents inducing infectious or non-infectious diseases with γδ T cell-targeting vaccines and to the use of such γδ T cell-targeting vaccines in the preparation of a medicament, to a method of identification of novel tumor or pathogen-derived antigens, and to a method of diagnosing the immune competence of patients using such efficient antigen-presenting human γδ T cells.

In particular, the present disclosure provides a method for cross-presentation of antigen to a CD8$^+$ αβ T cell, comprising first obtaining an enriched γδ T cell population from a population of human peripheral blood mononuclear cells. The population of human peripheral blood mononuclear cells may be fractionated or unfractionated. Next is the step of obtaining a stimulated γδ T cell population by exposing the enriched γδ T cell population to a stimulus effective for inducing an antigen-presenting function. The stimulated γδ T cell population is then exposed to a tumor- or microbial organism-derived antigen for uptake, processing, and presentation, to obtain an antigen-presenting γδ T cell population. The antigen-presenting γδ T cell population may then be exposed to a human blood cell population containing a population of CD8$^+$ αβ T cells to the antigen-presenting γδ T cell population. Suitable antigens may be derived from tumor cell or microbial organisms such as viruses, bacteria, yeasts, parasites, and the like, or from cells infected with such organisms.

Still further, the present disclosure provides a method for treatment of a tumor or a chronic or recurrent infectious disease, comprising delivering an antigen-presenting autologous γδ T cell population prepared as set forth above into a patient requiring such treatment. Suitable delivery routes include without limitation intradermal, subcutaneous, intramuscular, intravenous, mucosal, and submucosal delivery. The antigen-presenting autologous γδ T cell population may cross-present antigen derived from a tumor cell or from chronic or recurrent infectious disease-causing microbial organisms to a CD8$^+$ αβ T cell of the patient.

Still yet further, a method is described for preparing a peptide-specific effector T cell, comprising obtaining an enriched γδ T cell population from a population of human peripheral blood mononuclear cells and exposing the enriched γδ T cell population to a stimulus effective for inducing an antigen-presenting function to obtain a stimulated γδ T cell population. Next, the stimulated γδ T cell population is exposed to a tumor- or microbial organism-derived soluble peptide antigen for uptake, processing, and presentation, to obtain an antigen-presenting γδ T cell population. Then, CD8$^+$ αβ T cells are exposed to the antigen-presenting γδ T cell population to provide a peptide-specific effector T cell.

35- and M1p58-66-tetramer positive responder cells were determined at 10 d of culture. Data are representative of 2-4 experiments.

Figure 22:
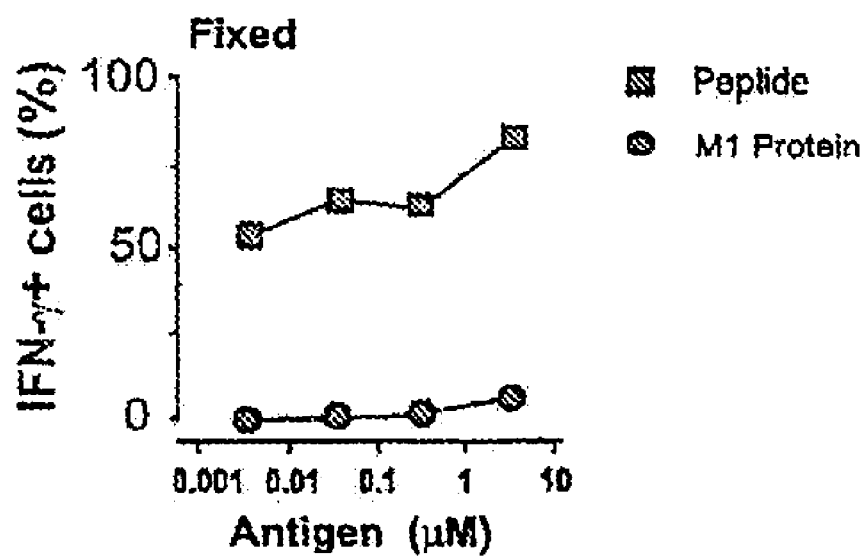
Figure 22:
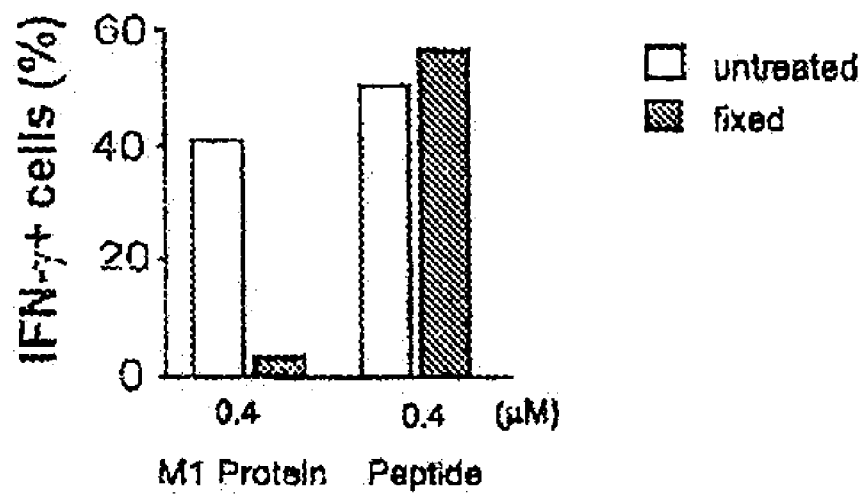

FIG. 22. Vγ9Vδ2$^+$ T cells express highly active immunoproteasome. (A) Proteins in lysates of freshly isolated (resting) Vγ9Vδ2$^+$ T cells or γδ T-APCs and of monocyte-derived DCs (iDCs) and feeder B cells (EBV-B) were separated by SDS-PAGE and analysed by Western blot. α5, protease subunit present in both standard and immunoproteasome; β1l (LMP2), immunoproteasome-specific subunit; Actin, protein loading control. (B) Purified proteasome from γδ T-APCs, monocyte-derived immature DCs (iDCs) and human embryonic epithelial cells (HEK293) were incubated at 37° C. for 16 h with the peptide substrate Melan-A$_{15-40}$ and the peptide products were identified by mass spectroscopy. The standard proteasome converts Melan-A$_{15-40}$ into Melan-A$_{15-35}$ (highlighted with gray bars), which is readily detected in the control digestion with proteasome from HEK293.

Figure 1A:
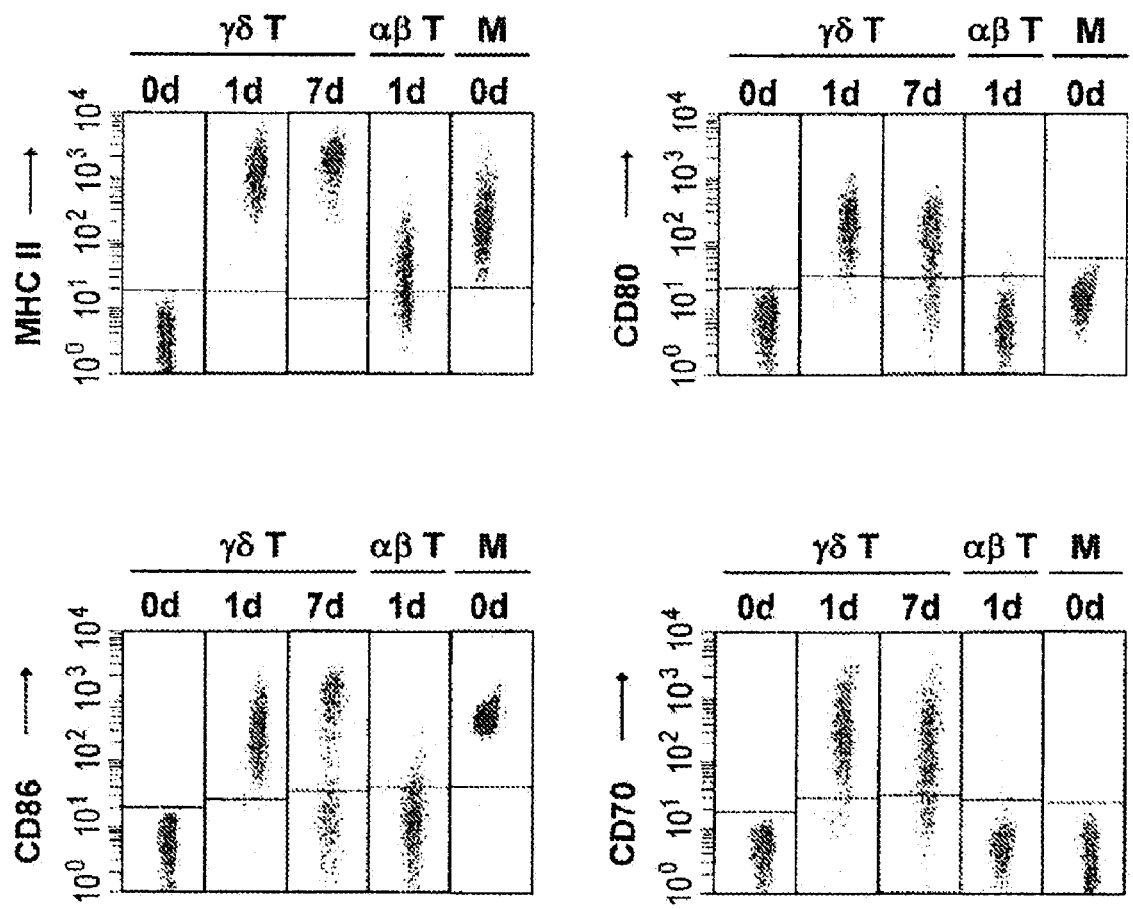
FIGS. 1 (1A and 1B). Stimulated γδ T cells exhibit numerous antigen-presentation, co-stimulation and adhesion molecules. Examination of cell surface molecules by flow cytometry is performed with γδ T cells (γδ T), either freshly isolated from peripheral blood or after stimulation with IPP and in vitro culture for 1 or 7 days, or with αβ T cells (αβ T) after 1 day stimulation with anti-CD3/CD28, or with freshly isolated peripheral blood monocytes (M). The numbers above the individual dot-blots refer to the time of in vitro culture; (0d) freshly isolated, (1d) 1 or (7d) 7 days. Positivity is defined by staining with isotype-matched control antibodies, and horizontal lines represent the gates for 99% background stainings.
Figure 1B:
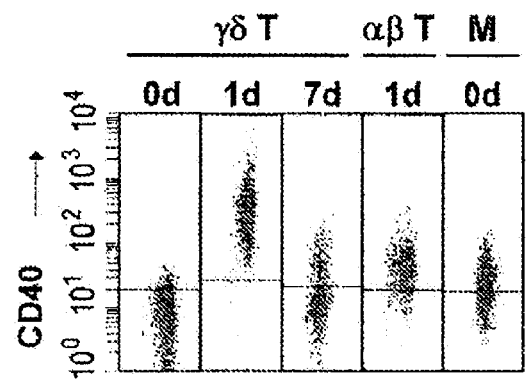
Figure 1B:
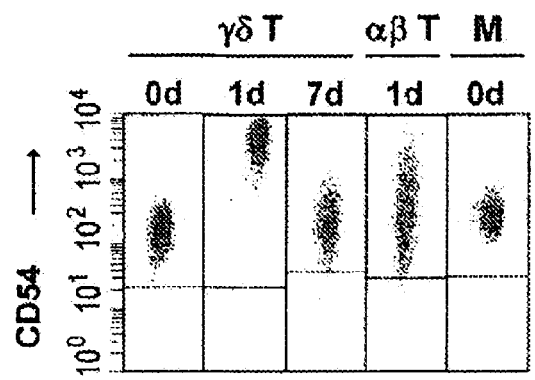
Figure 1B:
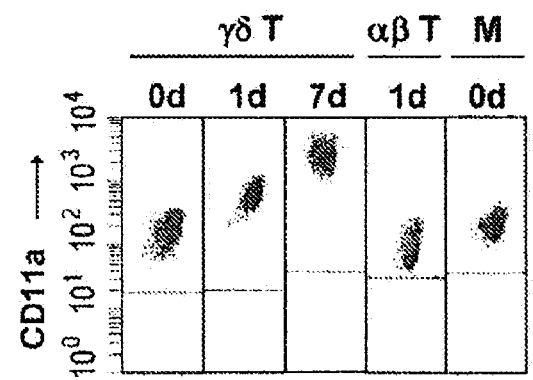
Figure 1B:
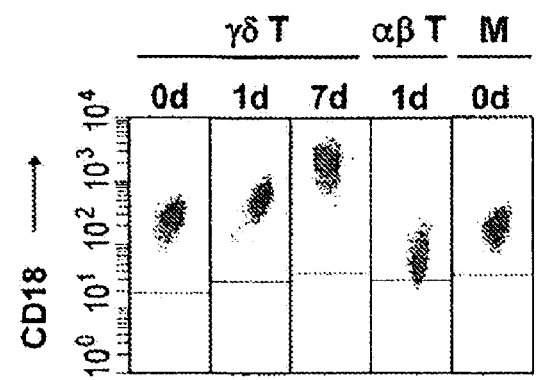
Figure 23:
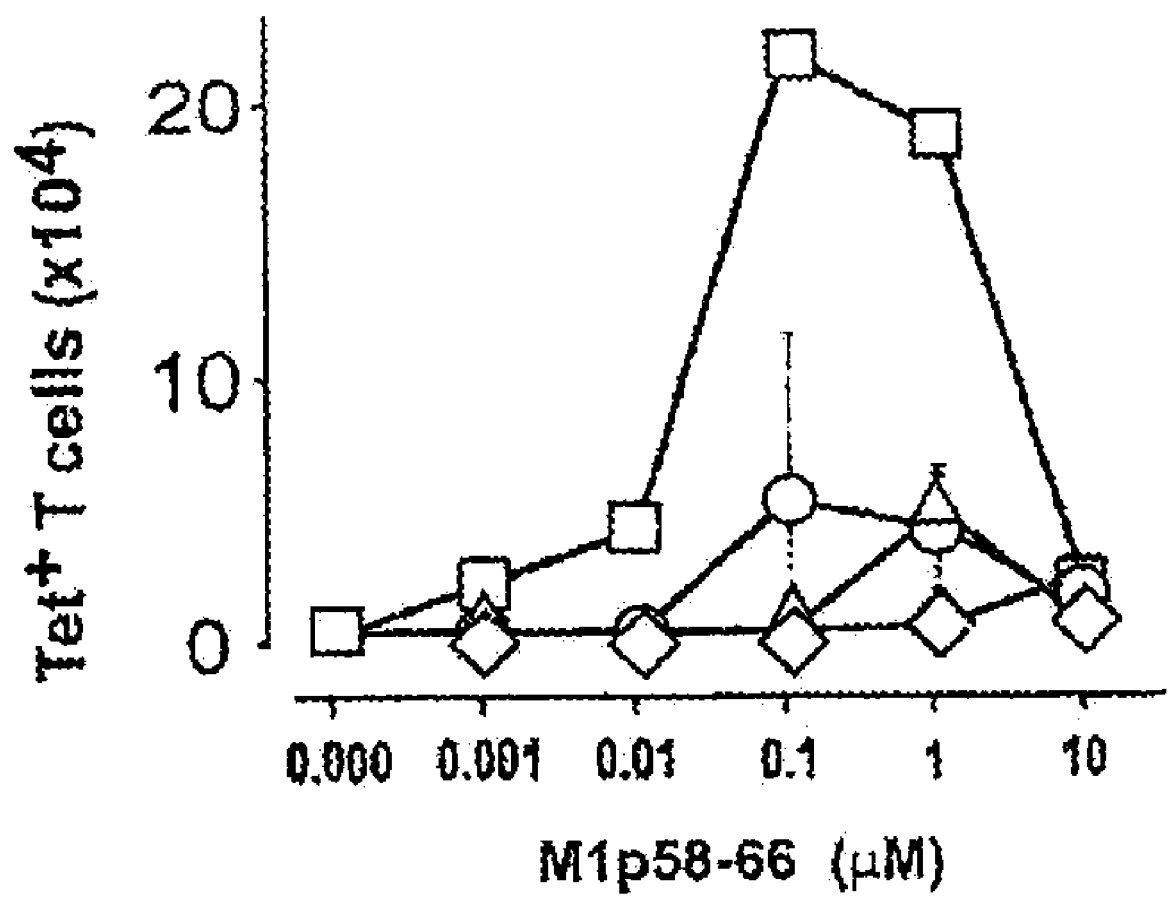

FIG. 23. Cross-presenting γδ T-APCs induce robust primary CD8$^+$ αβ T cell responses. (A) Cross-presenting γδ T-APCs induce proliferation in single-specific, naïve CD8$^+$ αβ T cells. γδ T cells and DCs, treated with 4 μM M1 (see FIG. 1c), were cultured with sorted naïve CD8$^+$ αβ T cells (APC/responder cell ratio of 1:20) for 10 d (cycle 1), or were re-stimulated with M1 cross-presenting APCs and cultured for another 10 d (cycle 2). Responder cells were identified by M1p58-66-tetramer staining. In the selected experiment (donor 1 blood cells), responses with DCs were below detection. Representative for experiments with cells form 3 different donors. (B) Naïve CD8$^+$ αβ T cells were cultured either in the absence of APCs (no APC) or with APCs pre-treated with Melan-A (8 μM), and cultures were examined for the presence of M1p58-66-specific or Melp26-35-specific cells. (C) M1 cross-presenting γδ T-APCs induce cytotoxic effector T cell generation. M1 cross-presenting γδ T-APCs and DCs (left and right panel, respectively) were used as APCs, and naïve CD8$^+$ αβ T cell-derived responder cells were cloned by limited dilution culture. $^{51}$Cr-labeled target cells were pulsed with M1p58-66 or Melp26-35 at indicated concentrations or were unpulsed and mixed at a 1:1 ratio with responder clones. One representative high-affinity and low-affinity responder clone are shown for each cytotoxic T cell cloning experiment; data in left and right panels are representative of the analysis of 13 and 8 separate M1p58-66-tetramer$^+$ T cell clones.

Figure 24:
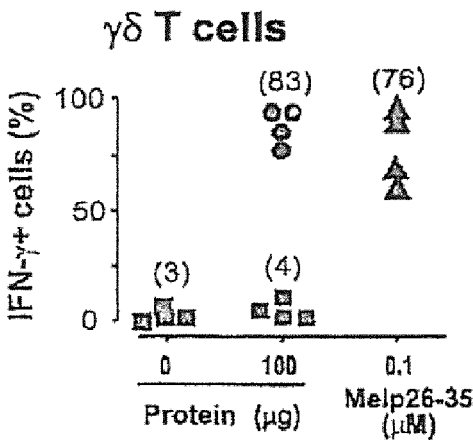
Figure 24:
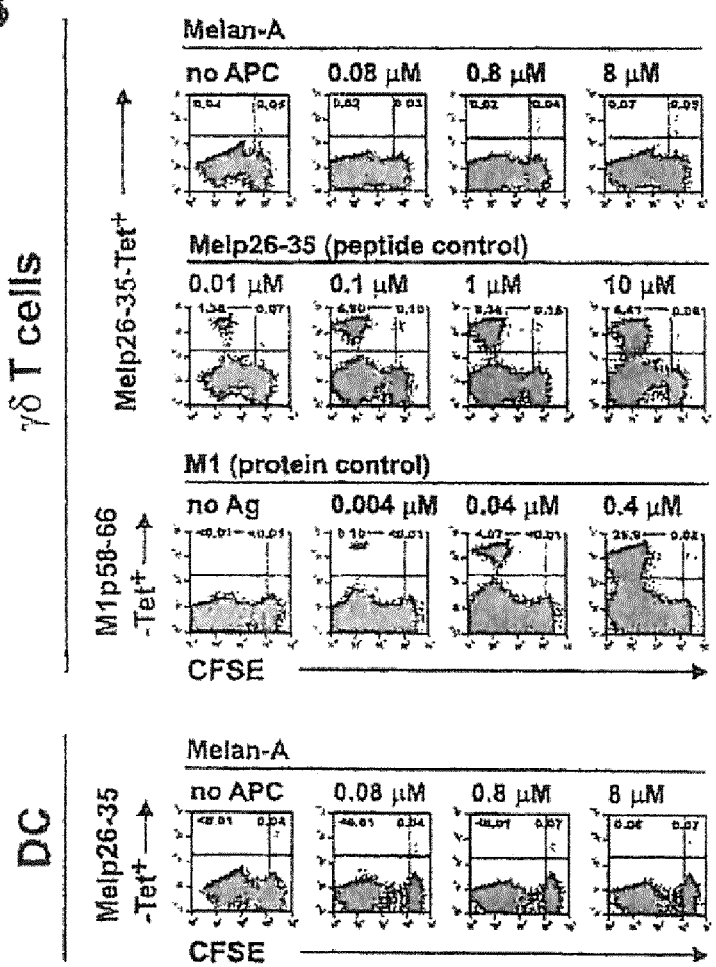

FIG. 24. M1 protein preparation does not contain M1p58-66 degradation peptide. In order to test if M1 protein preparations contained M1p58-66 as contaminant, γδ T-APCs were paraformaldehyde fixed (1%, 10 min, then quenched with 100 mM glycine) and pulsed with M1 protein or synthetic M1p58-66 at the indicated concentration. As control, untreated (non-fixed) γδ T-APCs were used to cross-present M1 or for pulsing with M1p58-66 at 0.4 μM. These APCs were then co-cultured with the HLA-A2-restricted, M1p58-66-specific CD8$^+$ αβ T cell clone FLUMA55 (APC/responder cell ratio of 1:1). The IFN-γ production in FLUMA55 (% intracellular IFN-γ$^+$ cells) was determined after 6 h. Data from 2 independent experiments are shown.

Figure 25:
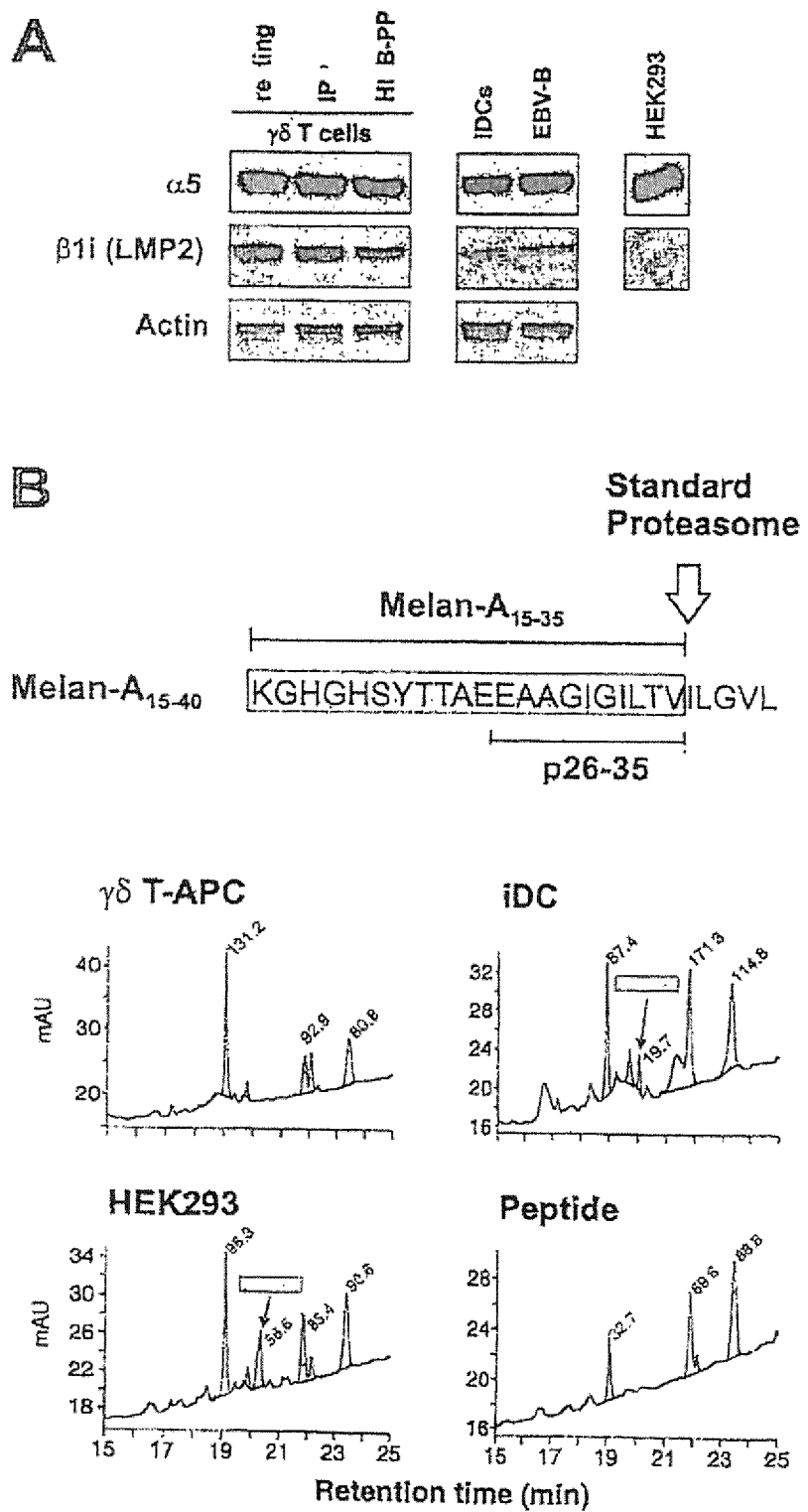

FIG. 25. γδ T-APCs are highly efficient in presenting M1p58-66 peptide to bulk CD8$^+$ αβ T cells. APCs, including γδ T-APCs, shear stress/LPS-DCs, monocytes and B cells, were pulsed with M1p58-66 at indicated concentrations, and co-cultured with bulk CD8$^+$ αβ T cells (containing naïve and memory subsets) at a APC/responder cell ratio of 1:20 (or 1:50 for B cells). B cells corresponded to those used as feeder cells during IPP-induced Vγ9Vδ2$^+$ T cell activation. M1p58-66-Tet$^+$ responder cells were enumerated after 10 d of culture by flow cytometry. Data are representative of 24 experiments.

Figure 26:
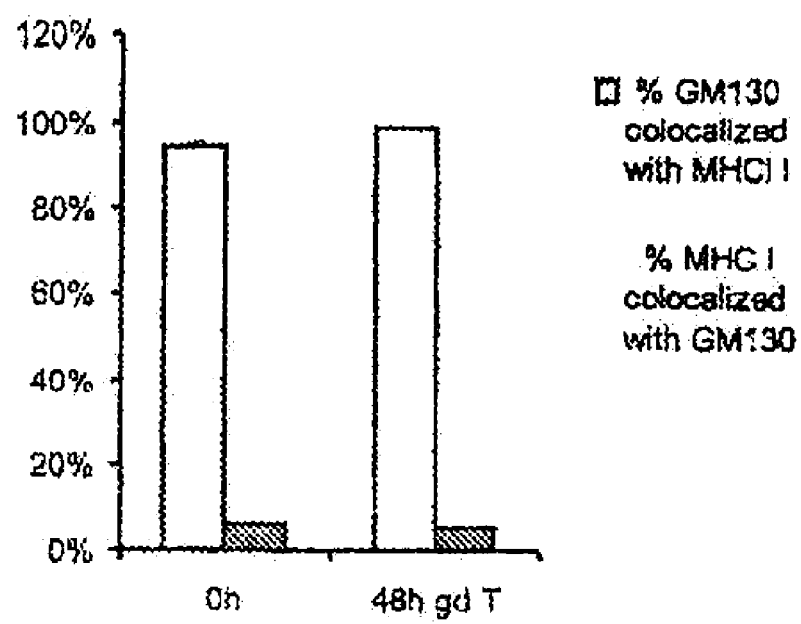
Figure 26:
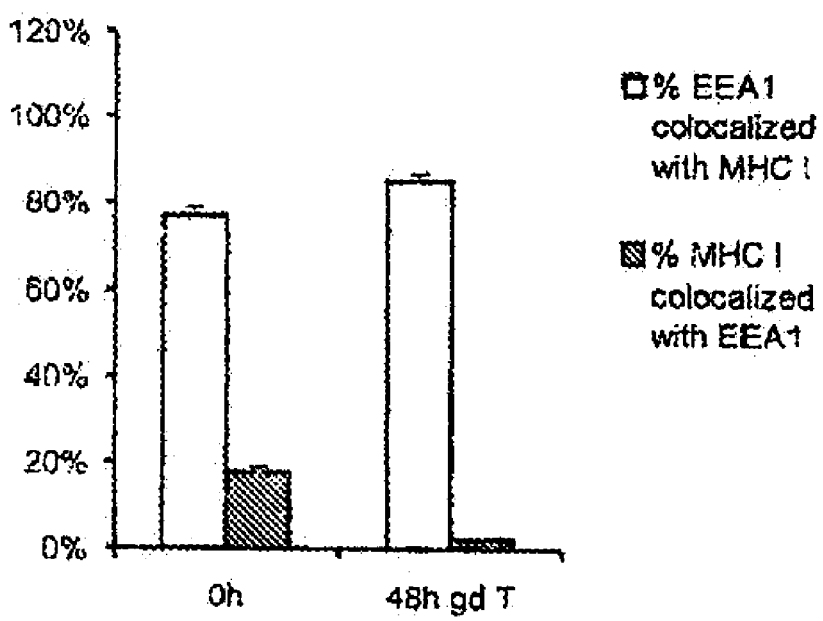

FIG. 26. Presence of MHC I in trans-Golgi during activation of Vγ9Vδ2$^+$ T cells. Cellular distribution of MHC I during activation of Vγ9Vδ2$^+$ T cells. Purified γδ T cells were cultured for 48 h in the presence of feeder B cells with IPP and then analyzed by confocal immunofluorescence microscopy as described in FIG. 3b. PBMCs were used as control for unstimulated γδ T cells (0 h). Graphs show the extent (%) of co-localization of GM130 staining with MHC I. Calculation was performed in 3D-restored, deconvolved images of confocal z-stacks by the co-localization analysis software Imaris 5.5 (Bitplane, Zurich, Switzerland).
94-99% of GM130 fluorescence co-localized with MHC I fluorescence, as calculated from 10 cells per time point. Conversely, only approx. 5% of MHC I fluorescence co-localized with the Golgi network.

Figure 27:
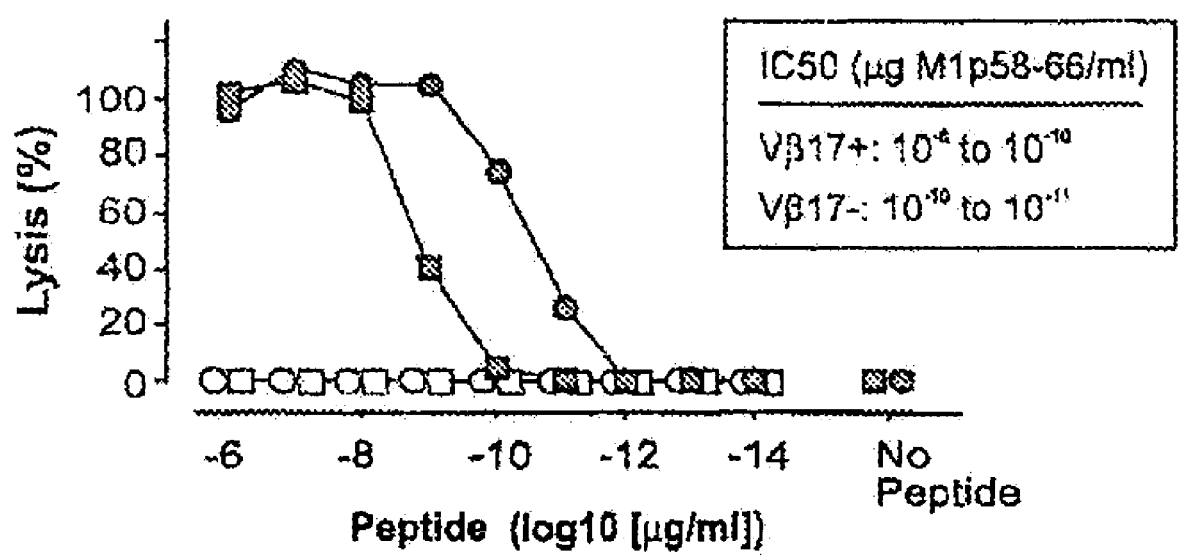

FIG. 27. The majority of naïve, M1p58-66-specific CD8$^+$ αβ T cells develop into effector cells that lack lymph node homing properties. Stimulation of naïve, M1p58-66-specific CD8$^+$ αβ T cells with M1 cross-presenting γδ T-APCs was performed as described in FIG. 23A. After in vitro culture, CD45RO$^+$M1p58-66-tetramer$^+$ and CD45RO$^+$M1p58-66-tetramer$^-$ responder cells were analyzed for expression of the lymph node homing receptors CCR7 and CD62L (L-selectin). CCR7 and CD62L are characteristic of naïve T cells and central-memory T cells, which continuously screen APCs in secondary lymphoid tissues for the presence of their cognate antigen. Most of M1p58-66-specific responder cells have acquired effector-memory cell characteristics, as shown by reduction of CCR7 and CD62L staining. Among M1p58-66-unrelated responder cells 50% or more cells still expressed CCR7 and CD62L. Data from two experiments (donor 1 and 4) are combined.

DETAILED DESCRIPTION OF THE INVENTION

The flow diagram of the Scheme summarizes the method of invention for the preparation of efficient antigen-presenting human γδ T cells (Vγ2Vδ2$^+$ γδ T cells, hereafter referred to as "γδ T cells") by isolation and in vitro treatment of human peripheral blood γδ T cells. Although protocols for isolation and in vitro proliferation of γδ T cells are known as such, the particular combination of stimulation and antigen application or peptide loading has not been described. Starting material is human peripheral blood that is processed by differential centrifugation or immunoabsorption to yield expanded or freshly isolated γδ T cells, respectively, at high purity. Short-term (e.g. 24 hours) stimulation in combination with antigen application or peptide loading results in γδ T cells with efficient antigen-presenting function for use in immunotherapy.

γδ T cells are readily expanded during culture of peripheral blood lymphocytes (PBLs) in the presence of isopentenyl pyrophosphate (IPP) or other small molecular weight non-peptide compounds with selectivity for γδ T cells as listed hereinbelow (Morita et al., 2000; Eberl et al., 2003). IPP or other small molecular weight non-peptide compounds with selectivity for γδ T cells are also used to induce antigen-presenting functions in selected γδ T cells as described hereinbelow. After 10-21 days in culture the vast majority of live, expanded cells are (Vγ2Vδ2$^+$) γδ T cells, which are separated from dead cells by Ficoll-Paque centrifugation and used immediately for antigen-presenting cell (APC) generation or stored in liquid nitrogen. Alternatively, as described in "Examples", γδ T cells are directly isolated from peripheral blood mononuclear cells (PBMCs) by means of positive selection.

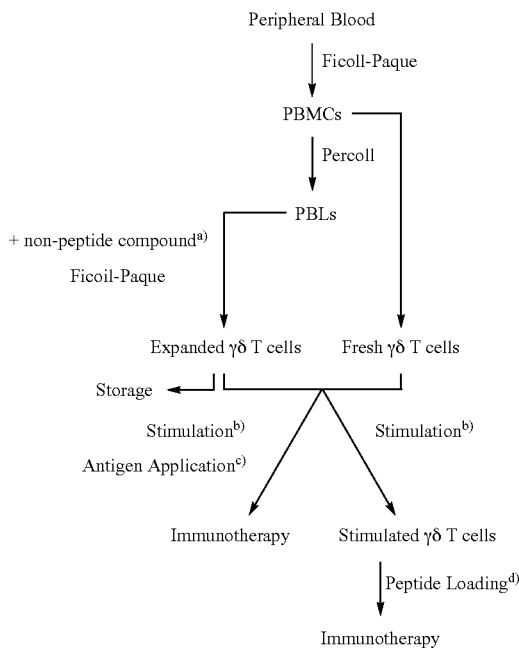

Scheme: Preparation of efficient antigen-presenting human γδ T cells b) Isolated fresh or expanded γδ T cells are stimulated for a short period (e.g. 12 to 96 hours) with (Vγ2Vδ2+) γδ T cell-selective compounds or phytohemagglutinin (PHA) or other stimuli as listed hereinbelow for Induction of antigen-uptake, of presentation function and of expression of co-stimulatory molecules.

c) γδ T cells are treated before; during or after stimulation (b) with antigens resulting in antigen-presenting γδ T cells. This antigen application includes a variety of independent approaches, such as (among others) addition of complex extracts or defined proteins from tumors, microbes or viral-infected cells or DNA/RNA encoding such pathogen-derived proteins, either in the form of purified nucleic material or packaged in expression vectors or attenuated viruses for transfection/transduction of γδ T cells and endogenous expression and processing of microbe-, pathogen- or tumor cell-derived antigens.

d) Instead of adding antigen (in the form of protein or DNA/RNA) to the γδ T cells during the short-term stimulation procedure (combinations of b and c), these steps may be performed sequentially. Stimulated γδ T cells are then "loaded" for a short period of time with defined peptide antigens that do not require intracellular proteolytic processing.

In addition to IPP, alternative small molecular weight non-peptide antigens with selectivity for (Vγ2Vδ2+) γδ T cells considered in step (a) are (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates. IPP is preferably applied as presented by B cells or substitutes.

Positive selection is, for example, performed by adding antibodies to human Vγ2Vδ2-TCRs to human peripheral blood mononuclear cells, e.g. 1-3 hours incubation, followed by magnetic cell sorting. Alternatively, positive selection may be performed by adding antibodies to human VγVδ-TCRs to human peripheral blood mononuclear cells (pan-γδT cell selection) followed by magnetic cell sorting.

(Vγ2Vδ2+) γδ T cell-selective compounds useful as stimuli for induction of antigen-presenting functions in Step (b) are IPP and other non-peptide compounds as listed above for step (a), e.g. 4-hydroxy-3-methyl-but-2-enyl pyrophosphate or other related microbial metabolites. Alternatively, PHA or other substitutes are useful as stimuli for induction of antigen-uptake, of presentation function and of expression of co-stimulatory molecules.

Stimulated cells may, if desirable, be irradiated in order to inhibit γδ T cell proliferation.

Examples of antigens applied as proteins in step (c) and/or (d) are those currently used in immunotherapy protocols employing DCs as antigen-presenting cells and are related to the therapeutic targets, e.g. tumor cells, infectious agents (microbes including viruses, bacteria, yeasts, and parasites), and pathogen-associated toxins. Such antigens include (but are not limited to) tumor-associated antigens (tumor-specific metabolic, structural and cell surface proteins, and the like); virus-associated antigens (virus-encoded envelope, structural, metabolic and enzymatic proteins, e.g. HIV gp120 proteins of different viral clades, HIV Tat, HIV proteases, e.g. envelope, structural, metabolic and enzymatic proteins derived from hepatitis viruses, influenza viruses, human cytomegalovirus, polio viruses, rabies viruses, herpes viruses, among others); bacteria-associated antigens (bacteria-encoded cell wall, structural, metabolic and enzymatic proteins, and the like, e.g. those derived from *Mycobacteria* (e.g. *M. tuberculosis, M. leprae*), *Listeria monocytogenes, Pneumococci, Staphylococci* (e.g. *S. aureus*), *Streptococci* (e.g. *S. pyogenes, S. pneumoniae*), *Vibrio cholerae, Clostridium tetani*, among others); yeast and fungi-associated antigens (yeast/fungi-encoded cell wall, structural, metabolic and enzymatic proteins, and the like, e.g. those derived from *Candida albicans, Aspergillus fumigatus*, among others); and pathogen-derived toxins (bacteria enterotoxins, e.g. staphylococcal enterotoxins, toxic shock syndrome toxin, tetanus toxins, among others). Examples of antigens applied as proteins also include those related to bacteria causing increased resistance to antibiotic treatment and those microorganisms causing life-threatening diseases world-wide (e.g. Plasmodia (for example *P. falciparum, P. vivax, P. malariae*), *Leishmania, Trypanosoma, Entamoeba, Schistosoma, Filaria*, among others)., Antigens applied in step (c) in the form of RNA/DNA include those currently used in blood and tissue cell transfection protocols and include (but are not limited to) those encoding proteins from tumor cells, infectious agents (microbes including viruses, bacteria, yeasts, and parasites), and pathogen-associated toxins, as listed above.

"Efficient" as used in "efficient antigen-presenting human γδ T cells" means that the antigen-presenting functions of such cells are comparable to the corresponding antigen-presenting functions of DCs. "Efficient" is e.g. at least 10% as effective as with DCs under comparable conditions, the difference being a result of different cell morphology, including cell shape and surface area.

Short-term stimulated γδ T cells uniformly express the chemokine receptor CCR7, which is a prerequisite for homing of APCs to lymph nodes and Peyer's patches and, consequently, is a critical factor for initiation of adaptive immune responses. Resting peripheral blood γδ T cells do not express MHC-II molecules and, therefore, are not capable of presenting peptide antigens in a tolerogenic fashion. This issue of "safety" puts γδ T cells apart from other APCs, such as DCs and B cells, with known tolerance induction properties. Applications of antigen-presenting γδ T cells include, among others, the induction and/or improvement of immune responses against tumors in the treatment of tumor patients and against microbes and viruses in the treatment of patients with chronic infections or with inappropriate immune competence. In addition, antigen-presenting γδ T cells can be used for identification of novel tumor and otherwise pathogen-derived antigens with strong immunogenic properties for potential application in immunotherapy. Eventually, the application of γδ T cells to monitor the adaptive immune competence (status of immune competence) of immune-suppressed individuals (among others) is described.

The invention is now described in more detail with reference to the accompanying figures, which give ample proof of the efficiency of the method of the invention.

FIG. 1 describes the expression of cell surface molecules on γδ T cells, immediately after isolation from peripheral blood or after stimulation and culture for 1 or 7 days. For comparison, the same cell surface molecules are also examined on 1 day stimulated αβ T cells and freshly isolated monocytes. The cell surface molecules shown in FIG. 1 include MHC-II; the co-stimulatory molecules CD80 and CD86, the two selective ligands for the receptor CD28 present on naïve and memory T cells: CD70, the ligand for CD27; CD40, the receptor for CD154/CD40-ligand as well as the adhesion molecules CD54/ICAM-1, CD11a/α-integrin, and CD18/β2-integrin, which are involved in cell-to-cell contact. These data demonstrate that freshly isolated γδ T cells have moderate levels of adhesion molecules but lack MHC-II and co-stimulatory molecules that are essential for the activation and differentiation of naïve T cells. By contrast, short-term (1 day) stimulation of γδ T cells results in very high levels of expression of MHC-11 and co-stimulatory molecules and further enhance expression of adhesion molecules. Of note, and with the exception of CD40 and CD54, the levels of these cell surface molecules are maintained or further enhanced during culture of γδ T cells for 7 days. In clear contrast, the same series of molecules (with the exception of CD86 on monocytes) are moderately expressed or absent on αβ T cells and monocytes.

The numbers in Table 1 summarize the results from an extensive investigation of the expression of cell surface molecules on γδ T cells and, for comparison, on αβ T cells, monocytes and mature DCs. The list includes the examples shown in FIG. 1 as well as additional cell surface molecules. The numbers indicate the average expression levels, expressed as the mean of the mean fluorescence-intensity (MFI), and the corresponding standard deviations (SD). Note the striking positivity of MHC-II (HLA-DR), co-stimulatory and adhesion molecules on activated γδ T cells that resembles mature DCs but exceeds by far the levels seen in activated αβ T cells and monocytes.

Figure 2:
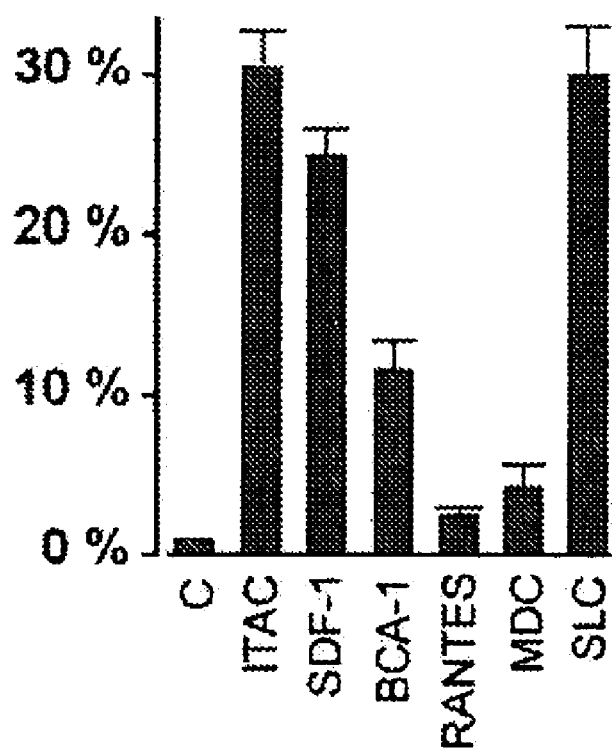
FIG. 2. Stimulated γδ T cells express functional CCR7 and respond to the LN chemokine SLC/CCL21. The data are taken from Brandes et al., 2003. A) Chemotaxis responses are examined in γδ T cells after stimulation for 36 hours with IPP, and expressed as the fraction of cells (%), i.e. % of total input cells, that have migrated in response to the indicated chemokines. C=Control (blank). B) CCR7 expression is determined by flow cytometry, n=cell counts. Solid and broken lines refer to CCR7 expression on IPP-stimulated (see chemotaxis) and resting peripheral blood γδ T cells, respectively; filled histogram depicts control staining with isotype antibody.
Figure 2:
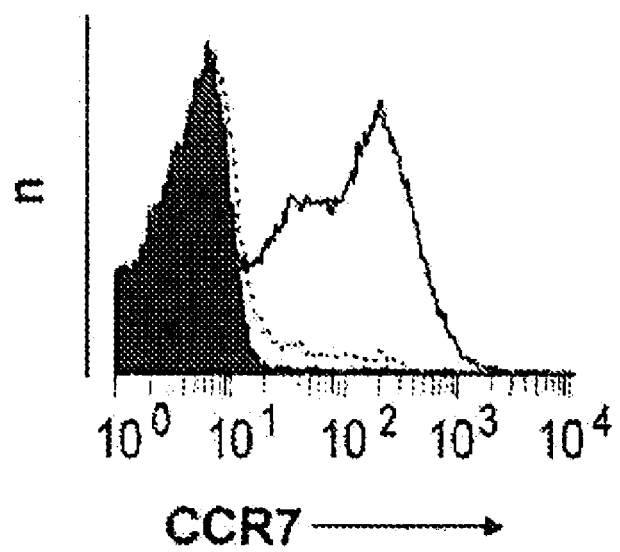

FIG. 2 and Table 2 correspond to previous results published by Brandes et al., 2003, and are included here to describe additional features of activated human γδ T cells that are pertinent to this invention. Table 2 lists the expression levels of chemokine receptors that differ clearly between freshly isolated peripheral blood γδ T cells and stimulated γδ T cells. γδ T cells in peripheral blood express chemokine receptors and adhesion molecules (shown in FIG. 1) for rapid recruitment to sites of inflammation and infection whereas short-term activation of γδ T cells partially inhibits these inflammatory migration properties (i.e. downmodulation of CCR2 and CCR5) and instead rapidly induces CCR7 expression for efficient homing to T cell areas of spleen, LNs and PPs.

TABLE 1

Expression levels of cell surface molecules on human γδ T cells.

| | fresh γδ T cells MFI ± SD (n)[a] | 1 day γδ T cells MFI ± SD (n) | 7 days γδ T cells MFI ± SD (n) | 1 day γδ T cells MFI ± SD (n) | fresh monocytes MFI ± SD (n) | 8 h LPS DC MFI ± SD (n) |
|---|---|---|---|---|---|---|
| HLA-DR | 8 ± 13 (4) | 1738 ± 229 (4) | 2426 ± 1416 (4) | 368 ± 200 (8) | 743 ± 298 (4) | 1873 ± 142 (3) |
| CD80 | 0 ± 0 (3) | 157 ± 74 (3) | 115 ± 30 (4) | 3 ± 22 (8) | 2 ± 2 (6) | 109 ± 90 (3) |
| CD86 | 2 ± 1 (4) | 499 ± 249 (4) | 412 ± 256 (6) | 89 ± 89 (12) | 333 ± 130 (5) | 299 ± 325 (2) |
| CD70 | 0 ± 0 (4) | 293 ± 191 (3) | 422 ± 229 (3) | 11 ± 5 (6) | 0 ± 0 (4) | 0 ± 0 (2) |
| CD54 | 179 ± 44 (3) | 3589 ± 646 (3) | 511 ± 116 (3) | 949 ± 529 (6) | 602 ± 194 (3) | 1272 ± 605 (2) |
| CD11a | 274 ± 90 (3) | 651 ± 86 (2) | 2663 ± 919 (2) | 154 ± 8 (2) | 411 ± 179 (4) | 4 (1) |
| CD18 | 233 ± 60 (3) | 547 ± 18 (2) | 1174 + 420 (2) | 129 ± 11 (2) | 283 ± 34 (4) | 5 (1) |
| CD40 | 10 ± 8 (3) | 684 ± 41 (2) | 46 ± 7 (3) | 108 ± 13 (4) | 69 ± 33 (3) | 493 ± 179 (2) |
| CD11b | 55 ± 11 (5) | 141 ± 63 (6) | 117 ± 182 (4) | 11 ± 6 (8) | n.d.[b] | 325 ± 118 (2) |
| CD11c | 8 ± 2 (2) | 100 ± 82 (3) | 168 ± 42 (4) | 46 (1) | n.d. | 453 ± 141 (2) |
| CD50 | 381 (1) | 347 ± 88 (2) | 347 ± 88 (2) | n.d. | n.d. | 30 ± 18 (2) |
| CD83 | 0 ± 0 (2) | 85 ± 79 (2) | 4 ± 1 (2) | n.d. | n.d. | 33 ± 22 (2) |

[a] Cells are stimulated and examined by flow cytometry for cell surface expression of indicated molecules as described in "Examples". MFI = mean fluorescence intensity; SD = standard deviation; (n) indicates the number of independent experiments.
[b] n.d. stands for not determined.

TABLE 2

Expression of chemokine receptors in human γδ T cells.

| | Fresh γδ T cells % of positivity[a] mean ± S.D. (n) | Activated γδ T cells % of positivity mean ± S.D. (n) |
|---|---|---|
| CXCR3 | 66.5 ± 8.2 (10) | 65.9 ± 18.9 (9) |
| CXCR4 | 53.1 ± 13.8 (7) | 57.2 ± 21.6 (6) |
| CXCR5 | 2.3 ± 1.8 (7) | 2.0 ± 2.9 (5) |
| CCR1 | 20.6 ± 10.7 (5) | 24.5 ± 16.9 (4) |
| CCR2 | 23.0 ± 7.2 (9) | 14.1 ± 5.3 (7) |
| CCR4 | 13.3 ± 10.2 (12) | 29.9 ± 10.8 (12) |
| CCR5 | 61.2 ± 10.4 (12) | 2.5 ± 5.4 (9) |
| CCR6 | 20.1 ± 11.1 (6) | 15.2 ± 14.7 (4) |
| CCR7 | 18.9 ± 9.7 (23) | 77.6 ± 14.7 (14) |

[a] The data are taken from Brandes et al., Blood (2003)

FIG. 2 illustrates the migration properties of short-term activated γδ T cells, as assessed by in vitro chemotaxis analysis (Brandes et al., 2003). The data clearly demonstrate the responsiveness toward the CCR7 ligand SLC/CCL21 and the strongly reduced responsiveness toward the CCR5 (and CCR1, CCR3) ligand RANTES/CCL5 in activated γδ T cells. The data further demonstrate that changes in the level of cell surface chemokine receptors are directly mirrored in migration responses to the corresponding chemokines.

Collectively, the results summarized in FIGS. 1-2 and Tables 1-2 underscore the fact that stimulated but not resting (freshly isolated) γδ T cells from peripheral blood express many essential factors, including adhesion and co-stimulatory molecules, and chemokine receptors, required for LN-homing and stimulation of naïve T cells. The activation-induced modulation of these migration- and APC-related parameters compares well with the activation-induced changes occurring in DCs (Banchereau and Steinman, 1998; Steinman et al., 2003; Banchereau et al., 2004). Furthermore, these data imply that stimulated human γδ T cells act as potent APCs comparable to DCs.

Figure 3:
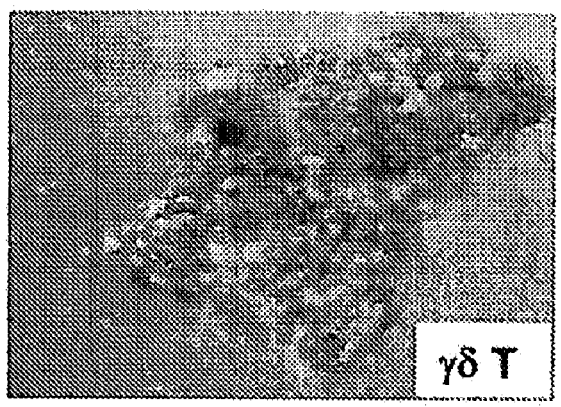
FIG. 3. Rapid and extensive aggregate formation between stimulated γδ T cells and naïve αβ T cells. 1 day stimulated γδ T cells are cultured together with autologous, naïve CD4$^+$ αβ T cells at the ratio of 1:5 for 3 hours (γδ T, 2 examples). As positive and negative control, mature monocyte-derived DCs (DC) and 1 day stimulated αβ T cells (αβ T), respectively, are mixed with autologous naïve αβ T cells. All cells are isolated from the same donor to exclude antigenic interactions. Naïve CD4$^+$ αβ T cells are loaded with CFSE for identification by fluorescence microscopy. The phase-contrast and fluorescence images of live cells are taken with a Zeiss-Axiovert 35 inverted microscope and images are combined in overlays.
Figure 3:
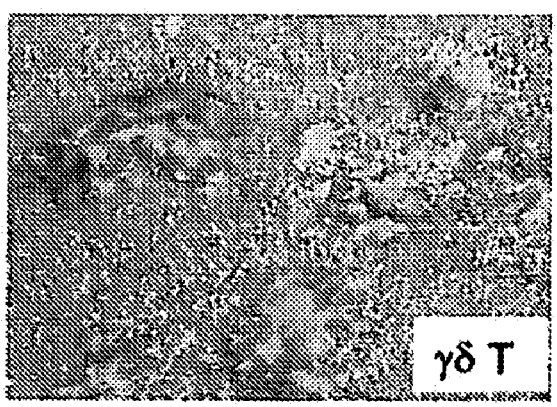
Figure 3:
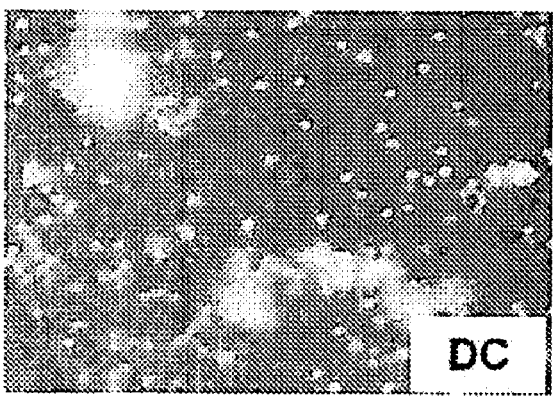
Figure 3:
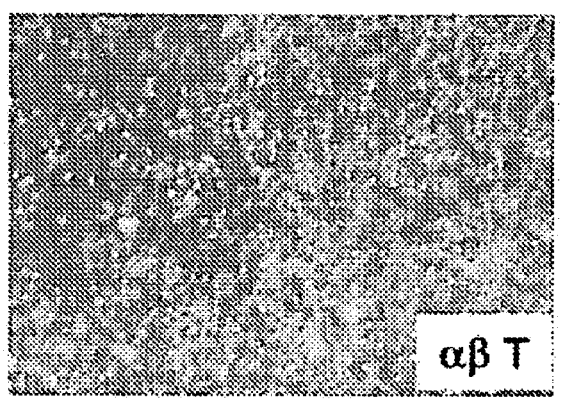

Rapid, extensive and antigen-independent cell cluster formation is characteristic for DC-T cell interactions and is a prerequisite for antigen-dependent stimulation and differentiation of naïve T cells. FIG. 3 documents that stimulated γδ T cells also induce tremendous cell clustering with naïve (resting) $CD4^+$ T cells within 3 hours of culturing. Of note, these clusters form in the absence of antigen, suggesting that adhesion and co-stimulatory molecules are responsible for this effect. The γδ T cell-mediated cluster formation is at least as robust as the one observed with mature DCs. By contrast, 1 day activated αβ T cells or freshly isolated monocytes (not shown) are much less efficient, which agrees with the reduced levels of adhesion and co-stimulatory molecules on these cells. These data provide further evidence that short-term activated γδ T cells have potent APC function.

Figure 4:
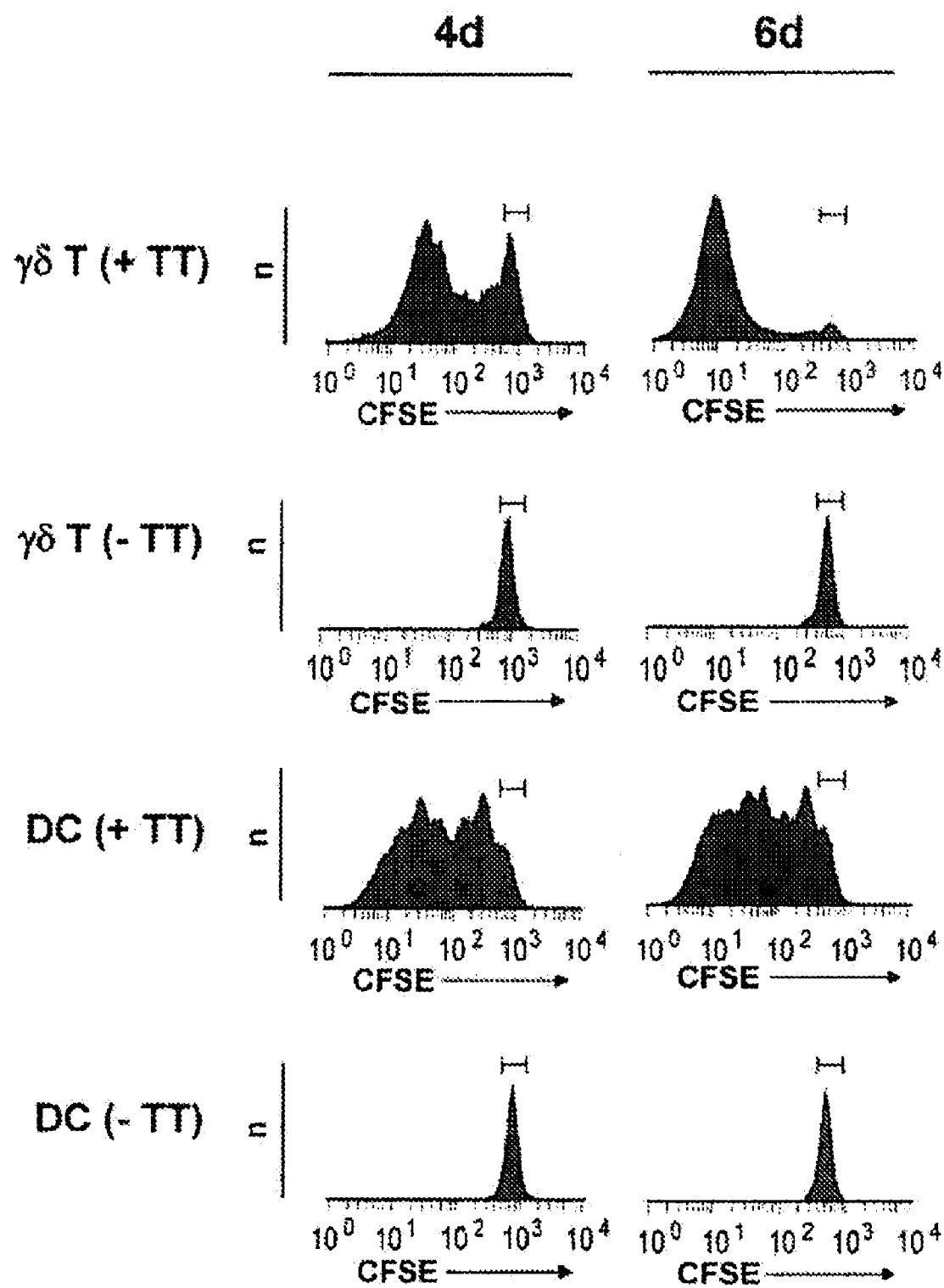
FIG. 4. Stimulated γδ T cells induce potent TT-specific proliferation responses in resting CD4+ αβ T cells. γδ T cells are stimulated for 1 day in the presence of 20 µg/ml TT, washed and then added to CFSE-labeled TT-specific αβ T cells at a ratio of 1:2. After 4 (4d) and 6 (6d) days of culture, the CFSE signals in CD4+ cells are examined by flow cytometry [γδT(+TT)]. As a positive control, monocyte-derived DCs are matured in the presence of 20 µg/ml TT [DC(+TT)] and used to stimulate αβ T cells at a ratio 1:10 under the same conditions as TT-presenting γδ T cells. As negative control, αβ T cells are co-cultured with γδ T cells [γδT(−TT)] and DCs [DC(−TT)], which are stimulated and matured, respectively, in the absence of TT. The horizontal bars above histograms indicate the positions of, CFSE signals in undivided (non-responsive) cells; n=cell counts.

Activated γδ T cells are able to take up, process and present antigen for triggering responses in antigen-specific $CD4^+$ αβ T cell lines. FIG. 4 shows proliferation of tetanus toxoid (TT)-specific $CD4^+$ αβ T cells in response to short-term stimulated, TT-presenting γδ T cells or, as control, TT-presenting DCs. The TT-specific $CD4^+$ αβ T cell line is derived from the same donor who provided the γδ T cells. Resting TT-specific $CD4^+$ αβ T cells are loaded with CFSE and proliferation of responder cells is determined by measuring the reduction of the CFSE signals in cultured cells by means of flow cytometry (see "Examples"). During cell division the CFSE content is distributed onto the two daughter cells such that each round of cell division is characterized by 50% reduction in CFSE signals. This type of analysis allows the determination of a) the fractions of non-responding versus proliferating cells (input/maximal versus reduced CFSE signals), b) the cellular subsets with distinct rounds of cell division, and c) the fraction of cells at the beginning of the experiment that has responded to the APCs. This information cannot be obtained by performing the $^3$H-thymidin-incorporation assay, which is an alternative method for the determination of cell proliferation. FIG. 4 shows that γδ T cells are capable of inducing proliferation in TT-specific $CD4^+$ T cells and that this response fully depends on the antigen, since γδ T cells that have been stimulated in the absence of TT are inactive. It further shows that between day 4 and day 6 of culture the $CD4^+$ T cells continue to proliferate, as evidenced by the further reduction of CFSE signals (shift to the left of fluorescence signals in FIG. 4). Of note, γδ T cells are similarly potent as mature DCs in this response, which demonstrates that short-term stimulated γδ T cells have potent antigen-presenting functions.

Figure 5:
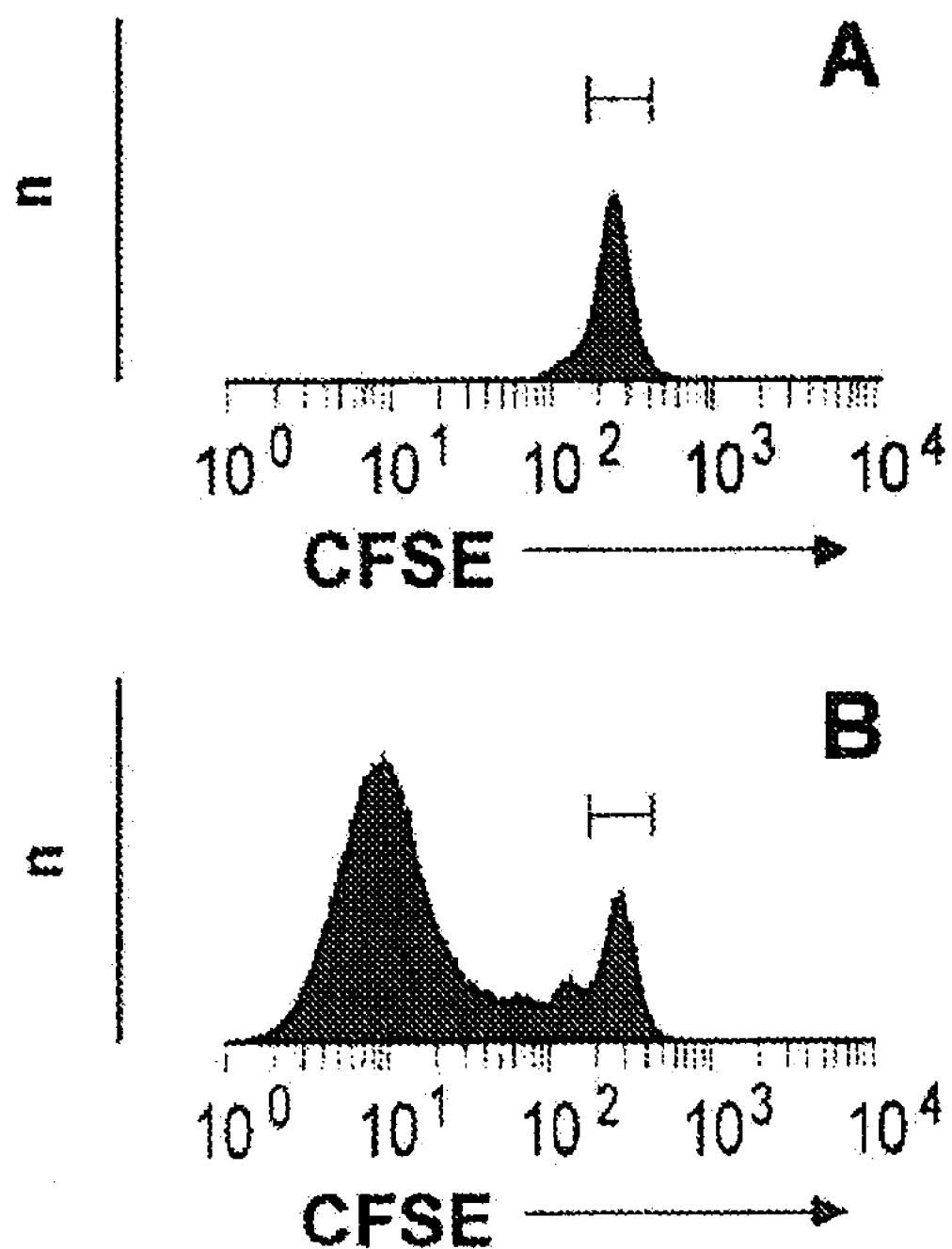
FIG. 5. Proliferation of TT-specific CD4+ αβ T cells requires contact with TT-presenting γδ T cells. Preparation of TT-presenting γδ T cells and CFSE-labeled responder cells as well as data analysis are performed exactly as described in FIG. 4. In a two-chamber tissue culture system, TT-presenting γδ T cells and TT-specific responder (CD4+ apt T) cells are added to the lower chamber (B), and responder cells alone are added to the upper chamber (A). The two chambers are separated by a porous membrane allowing the free exchange of soluble proteins but not intact cells. Horizontal bars above histograms indicate the gates for undivided CFSE-labeled cells.

FIG. 5 illustrates the fact that the TT-specific proliferation responses require cell contact between TT-presenting γδ T cells and responding TT-specific $CD4^+$ αβ T cells (responder cells). The responder cells that are separated by a porous membrane from co-cultures containing TT-presenting γδ T cells and responder cells do not proliferate. The porous membranes prevent the exchange of cells but do not prevent the exchange of soluble mediators between the two culture compartments. Therefore, the results in FIG. 5 also demonstrate that cytokines and growth factors produced during the co-culture of TT-presenting γδ T cells and responder cells have no effect on the proliferation of responder cells that are cultured separately.

Figure 6:
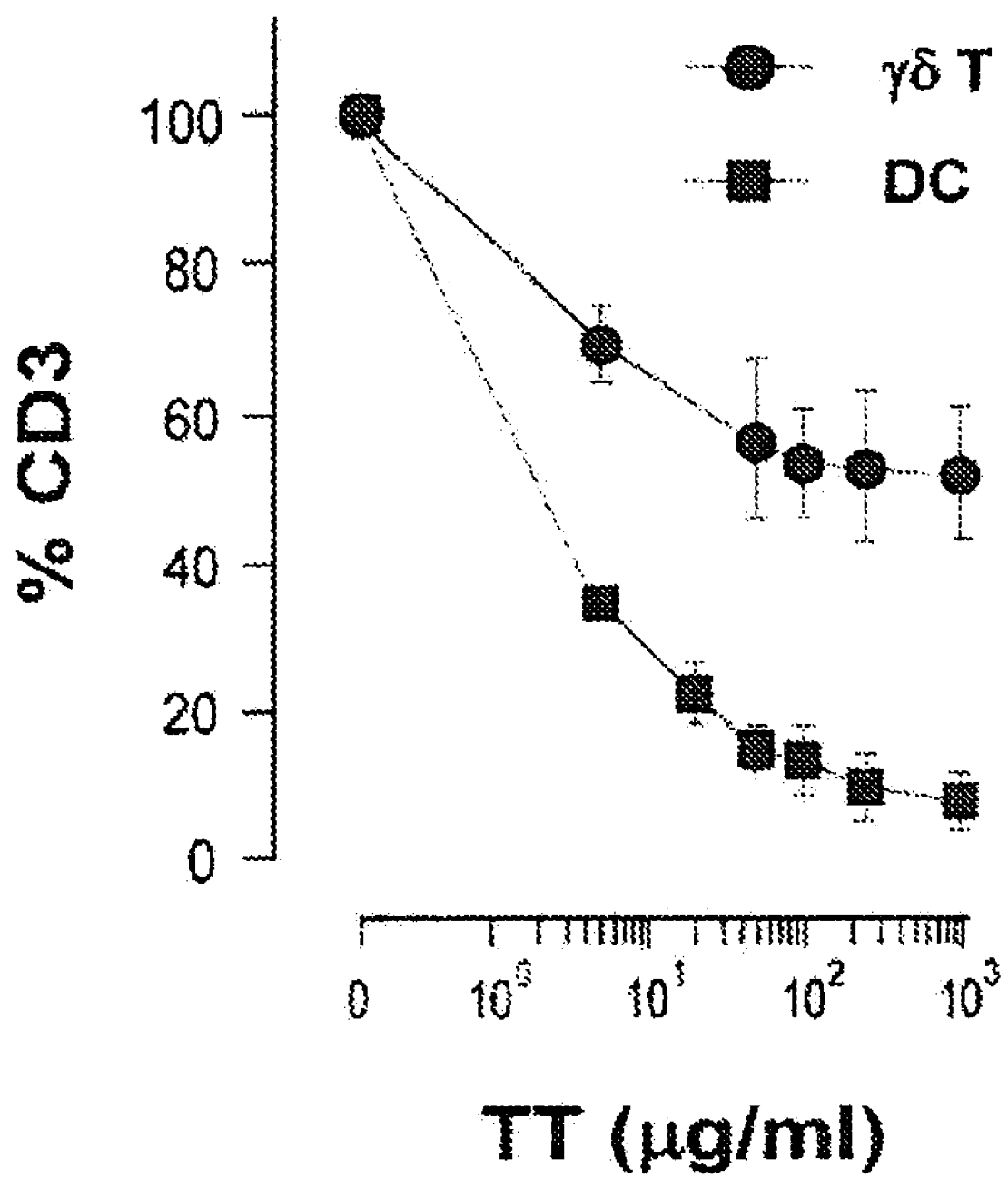
FIG. 6. TT-presenting γδ T cells induce TCR down-modulation in TT-specific CD4+ αβ T cells. γδ T cells and DCs are stimulated and matured, respectively, in the presence of increasing concentrations of TT, ranging from 0 (no TT added) to 1'000 µg/ml and then cultured with resting TT-specific CD4+ αβ T cells at a APC:responder cell ratio of 1:2. After 18 hours, the level of CD3 expression on αβ T cells is determined by flow cytometry and shown in % of mean fluorescence intensity (MFI) compared to cells without TT added. Preparation of TT-presenting γδ T cells and responder cells as well as data analysis are performed exactly as described in FIG. 4.

TCR triggering is accompanied by TCR internalization, resulting in the downmodulation of cell surface TCR and accessory molecules, such as CD3. FIG. 6 documents that TT-presenting γδ T cells induce TCR downmodulation in TT-specific responder cells (see FIG. 4), as assessed by loss of cell surface CD3. Consequently, γδT cells have the capacity to take up and process TT and to present TT-derived peptides in the form of MHC-II-peptide complexes to TT-specific responder cells in a manner sufficient for TCR engagement. Since activated but not resting peripheral blood γδ T cells express cell surface MHC-II molecules, the antigen-presentation function is closely associated with γδ T cell activation; FIG. 6 also shows that TCR downmodulation is a function of the density of TT-peptides on stimulated γδ T cells, which is controlled by varying the amount of TT added during γδ T cell stimulation. Obviously, the more TT-derived MHC-II-peptide complexes are present on stimulated γδ T cells the more TCRs on responder cells become engaged and downmodulated. The different potency in TCR downmodulation between γδ T cells and DCs is likely due to striking differences in cell morphology, since the cell surface area in mature, antigen-presenting DCs is >10-fold larger than in stimulated γδ T cells (Miller et al., 2004).

Figure 7:
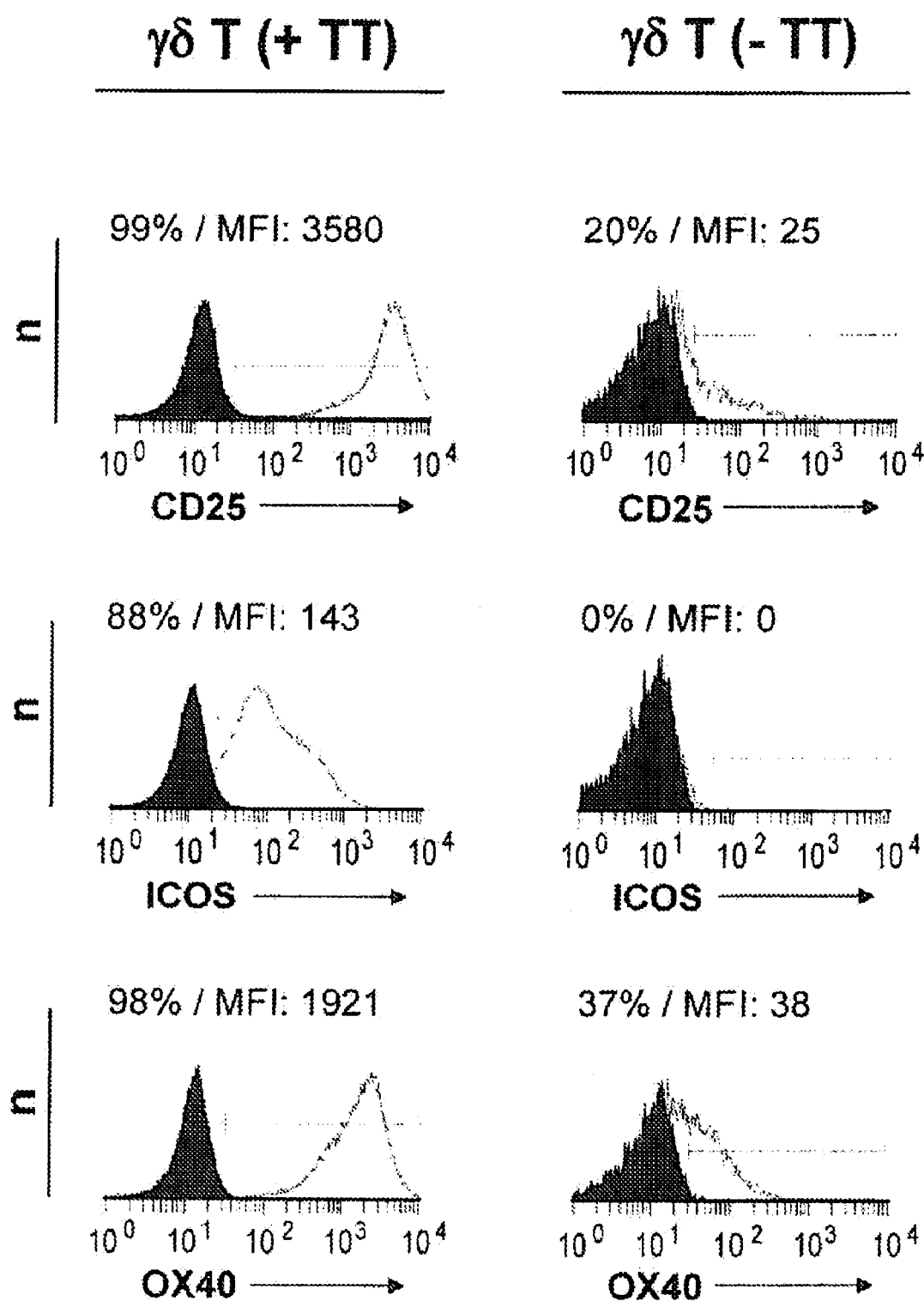
FIG. 7. TT-presenting γδ T cells induce the expression of activation markers on TT-specific CD4+ αβ T cells. The level of the activation markers CD25, ICOS and OX40 on TT-specific CD4+ αβ T cells (responder cells) is determined by flow cytometry after culture for 5 days with γδ T cells that are stimulated in the presence (+TT) or absence (−TT) of 10 µg/ml TT (see FIG. 4). Open and filled histograms show the fluorescence stainings with specific and control isotype antibodies, respectively; n=cell counts. Horizontal bars represent the gates for marker-positive cells, and the numbers above the histograms indicate the degree of positivity, expressed as percent positive cells (%) and mean fluorescence intensity (MFI).

In addition to proliferation, TT-presenting γδ T cells induce the expression of activation markers in TT-specific $CD4^+$ αβ T cells. FIG. 7 shows the upregulation on the cell surface of responder cells of T cell activations markers, including CD25, ICOS and CD134/OX40, which are de novo expressed or enhanced in response to TCR triggering. As in induction of T cell proliferation, high-level expression of these activation markers fully depend on TT-peptide presentation by short-term stimulated γδ T cells, since these activation markers are not induced with γδ T cells, which are stimulated in the absence of TT.

Figure 8:
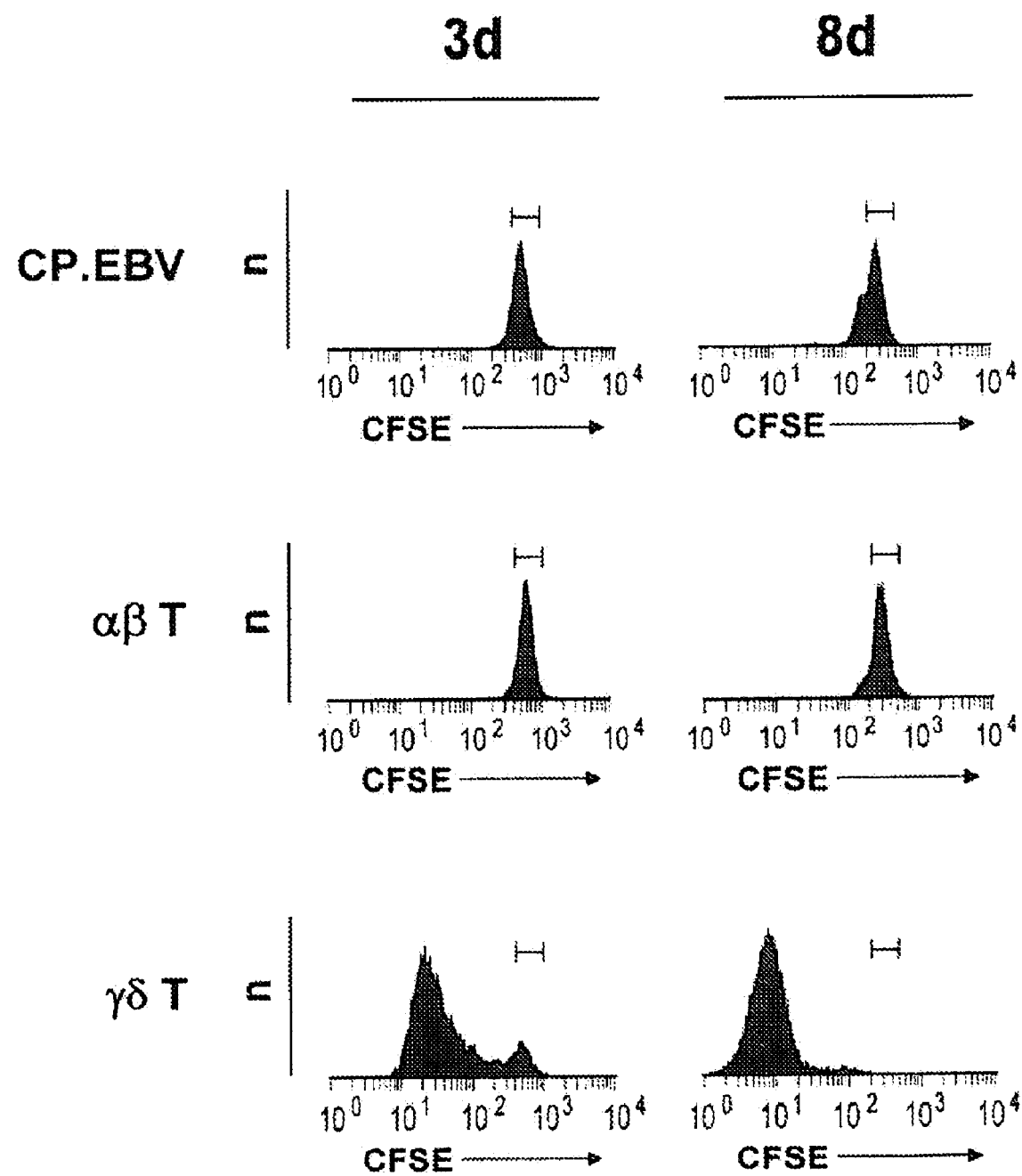
FIG. 8. Heterologous EBV-B cells and TT-specific CD4+ αβ T cells do not functionally present TT to TT-specific responder cells. CP.EBV cells, responder cells (TT-specific CD4+ αβ T cells) and γδ T cells (as positive control) are cultured for 1 day in the presence of 20 µg/ml TT, washed, irradiated and then added to TT-specific CD4+ αβ T cells at a ratio of 1:2. After 3 (3d) and 8 (8d) days of culture, the CFSE signals in CD4+ cells are examined by flow cytometry. CP.EBV and responder cell preparation, CFSE-labeling and flow cytometry are described in "Examples".

FIG. 8 shows that heterologous Epstein Barr Virus (EBV)-immortalized B cells and autologous responder cells lack TT-presenting function. One protocol for stimulation of γδ T cells includes the use of irradiated, IPP-presenting cells that are either autologous B cells or, for convenience of in vitro experimentation, EBV-B cell lines, i.e. the heterologous CP.EBV line. FIG. 8 demonstrates that TT-treated CP.EBV cells fail to induce the proliferation of TT-specific $CD4^+$ αβ T cells, indicating that CP.EBV material did not contribute to the strong proliferative responses obtained with TT-peptide presenting γδ T cells. Also, FIG. 8 illustrates the poor TT-presenting function of the αβ T cell line on its own.

Figure 9:
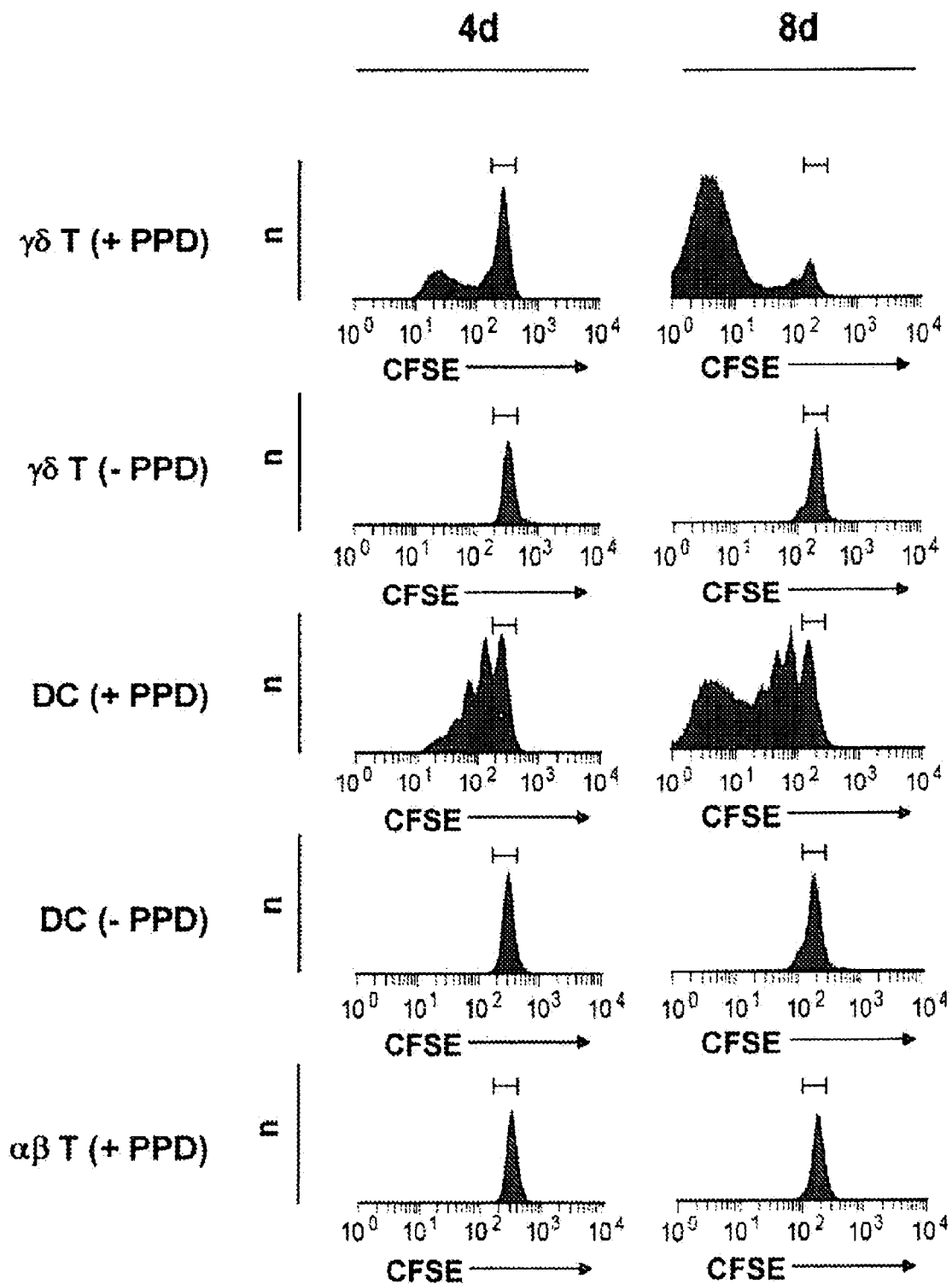
FIG. 9. Stimulated γδ T cells are also efficient in processing and presenting complex protein antigens (PPD). γδ T cells and DCs are stimulated/matured in the presence (+PPD) or absence (−PPD) of 20 µg/ml PPD and analyzed for induction of proliferation in resting autologous PPD-specific CD4+ αβ T cells. As additional negative control, PPD-specific CD4+ αβ T cells are cultured in the absence of γδ T cells or DCs but in the presence of 20 µg/ml PPD. The experimental set-up is identical to the one used in FIG. 4. γδ T cells and DC preparation, CFSE-labeling of PPD-specific CD4+ αβ T cells and flow cytometry are described in "Examples".

Similar effects as those shown in FIGS. 4-8 with TT are obtained with the complex/undefined antigen *Mycobacterium tuberculosis* purified protein derivative (PPD). FIG. 9 shows the proliferation responses of PPD-specific $CD4^+$ αβ T cells after 4 days or 8 days of culture following stimulation with PPD-peptide presenting γδ T cells or, alternatively, PPD-peptide presenting DCs as APCs. Again, the experiments are performed under autologous conditions, i.e. the APCs, (γδ T cells and DCs) and responder cells (PPD-specific $CD4^+$ at T cell line) are derived from the same donor. As documented for TT, the proliferation responses are PPD-specific and do not differ substantially between γδ T cells and DCs. Also, the αβ T cell line itself fails to induce proliferation in PPD-specific responder cells. At equal concentrations of antigen γδ T cells and DCs induce more vigorous responses with TT as compared to PPD, which is due to the differences in the complexity between TT ($M_r$ [TT]: 150 kDa) and PPD ($M_r$ [PPD]: ≧10,000 kDa). Complex antigens, such as PPD or whole microorganisms, are highly diverse in the repertoire of antigenic peptides with the consequence that individual APCs present discrete MHC-peptide complexes at low levels. In agreement, TCR downmodulation is much less evident in cloned, PPD-specific CD4$^+$ T cells during co-culture with PPD-presenting APCs than what is observed in the TT-system (FIG. 6).

Collectively, the experiments with TT-specific and PPD-specific responder cells document the finding of the present invention that stimulated (but not resting) γδ T cells derived from human peripheral blood have potent antigen uptake, antigen presentation and T cell stimulation functions. The potency and efficacy of these γδ T cells functions are remarkable and equal those obtained with DCs.

The characteristic of efficient APCs, such as DCs, is their ability to induce primary adaptive immune responses that involve the stimulation of naïve (antigen-inexperienced) T cells and their differentiation into antigen-specific effector T cells with the capacity to produce cytokines or to kill target cells (Banchereau and Steinman, 1998; Steinman et al., 2003; Banchereau et al., 2004). Fully differentiated memory T cells have reduced thresholds of activation, and TCR triggering in the absence of co-stimulation is sufficient to initiate effector functions. The experimental results shown in the following figures prove that stimulated γδ T cells also have efficient antigen-presenting functions comparable to those of DCs. Therefore, instead of antigen-experienced CD4$^+$ αβ T cell lines (FIG. 4-9), autologous freshly isolated naïve CD4$^+$ αβ T cells are used as potential responder cells.

Figure 10:
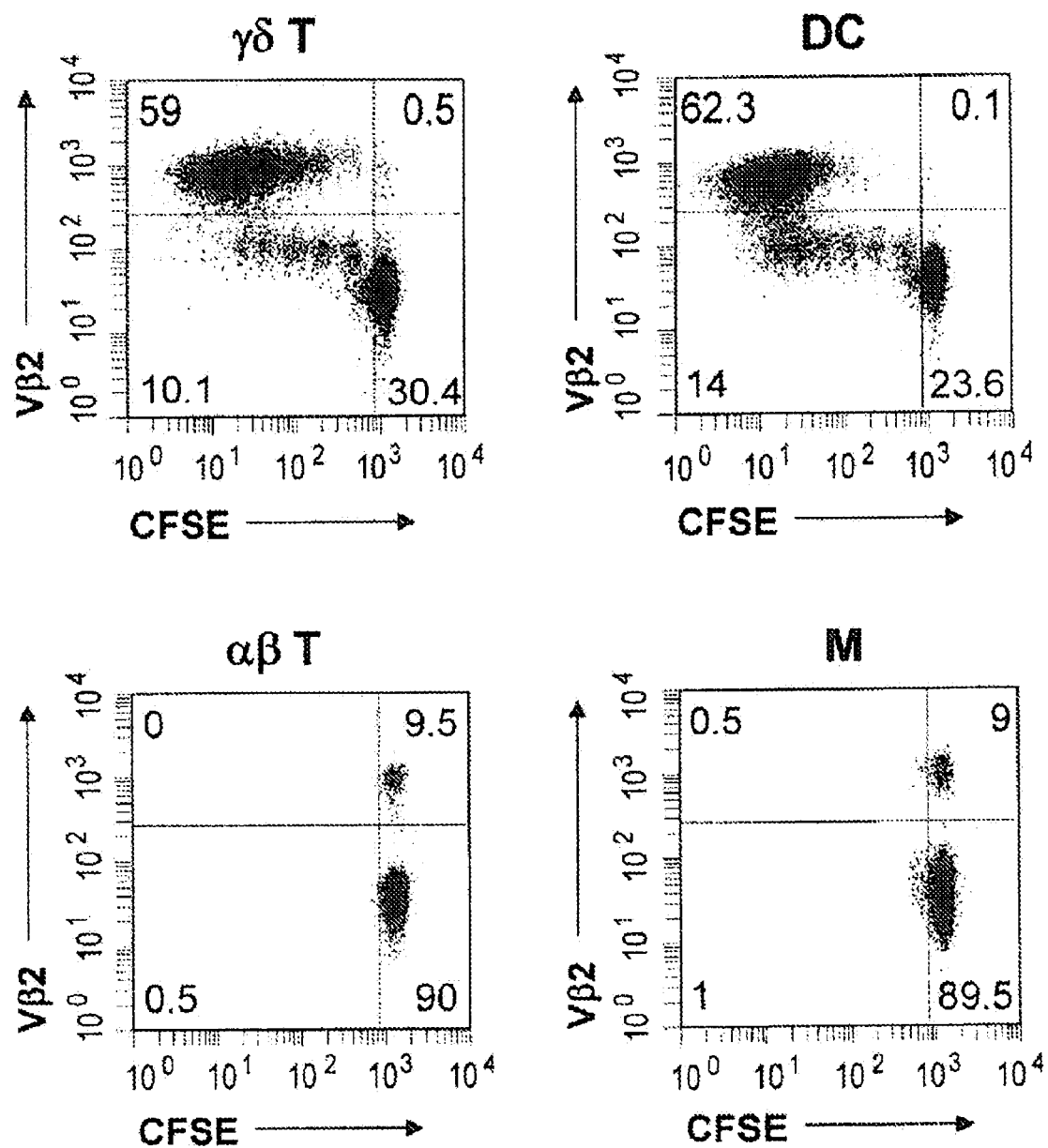
FIG. 10. TSST-1-loaded γδ T cells induce proliferation in autologous naïve CD4+ αβ T cells. Stimulated γδ T cells (γδ T), stimulated CD4+ αβ T cells (αβ T), mature DCs (DC) and freshly isolated blood monocytes (M) are loaded with 10 ng/ml TSST-1 and mixed with freshly isolated, CFSE-labeled naïve CD4+ αβ T cells at a ratio of 1:5. After 4 days of culture the proliferation responses in Vβ2+-αβ T cells (Vβ2) are determined by flow cytometry. Vertical and horizontal lines in the dot-blots define the gates for Vβ2+-αβ T cells and divided cells; the left-upper and left-lower quadrants show divided Vβ2+-cells and divided Vβ2$^{neg}$-cells, respectively, and the right-upper and right-lower quadrants show undivided Vβ2+-cells and undivided Vβ2$^{neg}$-cells; the numbers refer to the percent of total cells present within the individual quadrants. Cell preparation, TSST-1-loading and flow cytometry are performed according to "Examples".

FIG. 10 shows the extent of proliferation in CFSE-labeled, naïve CD4$^+$ αβ T cells in response to toxic shock syndrome toxin (TSST-1)-loaded, short-term stimulated γδ T cells and TSST-1-loaded mature DCs, as opposed to TSST-1-loaded stimulated αβ T cells or TSST-1-loaded freshly isolated monocytes. TSST-1 binds to MHC-11 molecules on APCs and is selective for αβ-TCRs containing the Vβ2-chain. 4-10% of peripheral blood CD3$^+$ T cells are Vβ2$^+$ and respond with high affinity to TSST-1-presenting APCs. As demonstrated in FIG. 10, TSST-1-loaded γδ T cells are expert APCs in induction of proliferation in naïve Vβ2$^+$-T cells, as evidenced by the reduction of CFSE signals, and this response is much more prominent in naïve CD4$^+$ αβ T cells bearing Vβ2$^+$-TCRs than those bearing Vβ2$^{neg}$-TCRs. Eventually, after completion of cell expansion most of the resulting memory T cells express Vβ2$^+$-TCRs (see also Table 3). Importantly, the proliferation responses equal the ones obtained with TSST-1-loaded DCs. Under these conditions, TSST-1-loaded αβ T cells or monocytes are completely inactive, indicating that the level of TSST-1-presentation and/or co-stimulation in these cells is not sufficient to induce efficient primary T cell responses.

TABLE 3

αβ T cell expansion and Th cell differentiation during long-term culture (21 days)

| APCs [a] | Ratio | Antigen [b] | ng/ml | Vβ2$^+$ (%) [c] | Th0 (%) [d] | Th1 (%) | Th2 (%) |
|---|---|---|---|---|---|---|---|
| γδ T | 1:5 | TSST-1 | 10 | 32 | 18 | 25 | 16 |
| γδ T | 1:1 | TSST-1 | 10 | 70 | 2 | 73 | 1 |
| γδ T | 1:5 | TSST-1 | 100 | 99 | 9 | 46 | 6 |
| γδ T | 1:5 | TSST-1 | 1000 | 93 | 13 | 50 | 5 |
| DC | 1:5 | TSST-1 | 10 | 80 | 6 | 84 | <1 |
| DC | 1:5 | TSST-1 | 100 | 83 | 2 | 86 | <1 |
| DC | 1:5 | TSST-1 | 1000 | 67 | 1 | 82 | <1 |
| — | | PHA | 1000 | 9 | n.d. [e] | n.d. | n.d. |

Figure 13A:
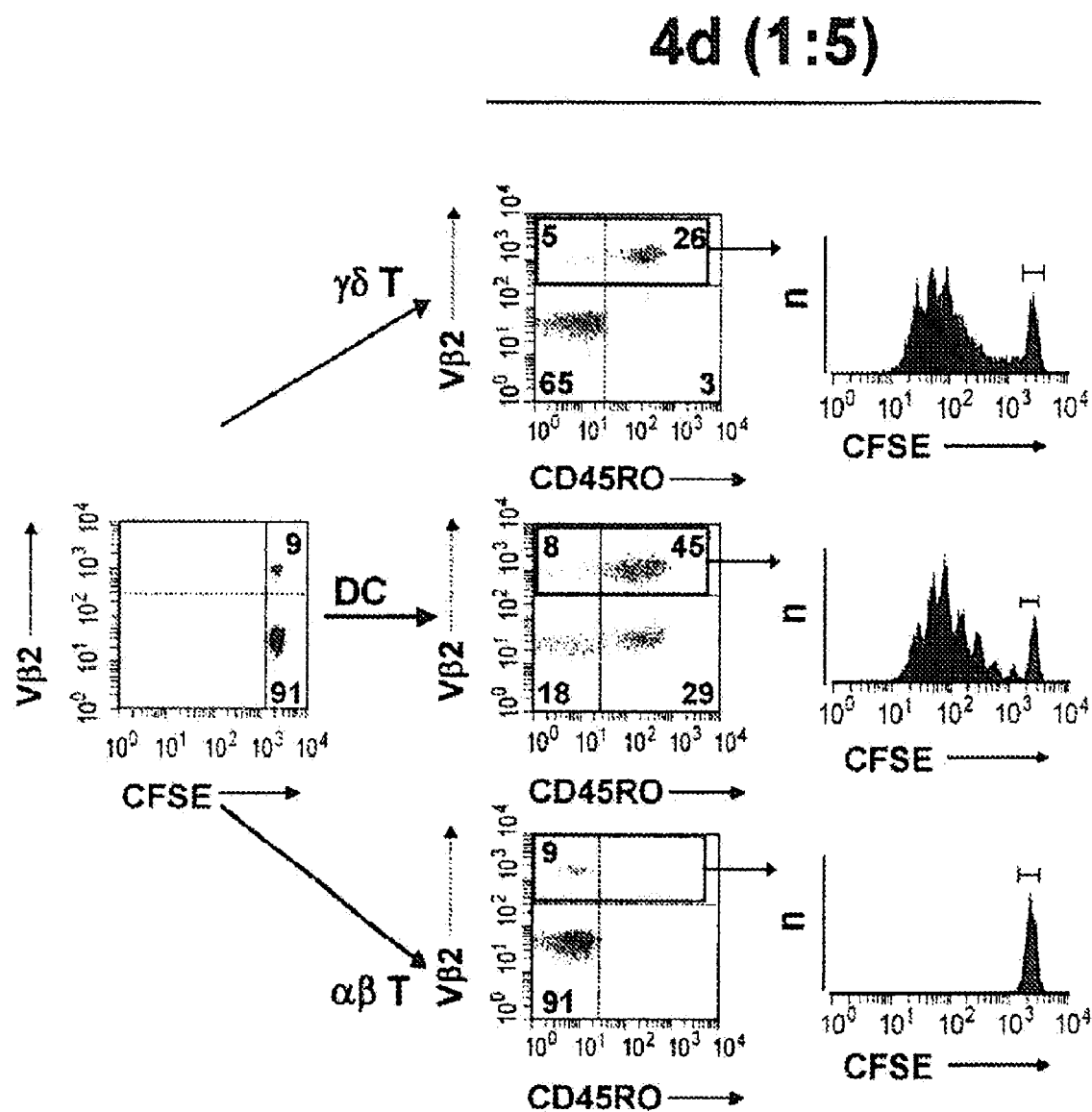
FIGS. 13 (13A and 13B). TSST-1-loaded γδ T cells induce T helper cell differentiation in naïve CD4+ αβ T cells. Stimulated γδ T cells, αβ T cells or mature DCs loaded with 10 ng/ml TSST-1 are mixed with naïve CD4+ αβ T cells, and Vβ2+ responder cell proliferation is examined as described in FIG. 10. After 4 days of culture, expression of the memory marker CD45RO and the extent of cell division are determined by flow cytometry in Vβ2+ responder cells. After 21 days of culture, when the cells return to a resting, non-proliferating state, cells are stimulated by PMA/ionomycin and examined by flow cytometry for the production of the intracellular cytokines IL-4 and IFN-γ (FIG. 13 B). The numbers in the left-upper, right-upper and right-lower quadrants define the fraction (percent of total cells) of Th2, Th0 and Th1 cells generated, respectively, and the numbers above the individual dot-blots refer to the ratio of APCs to responder cells at the beginning of the cell cultures. Cell preparation, TSST-1-loading and determination of cytokine production are described in "Examples".
Figure 13B:
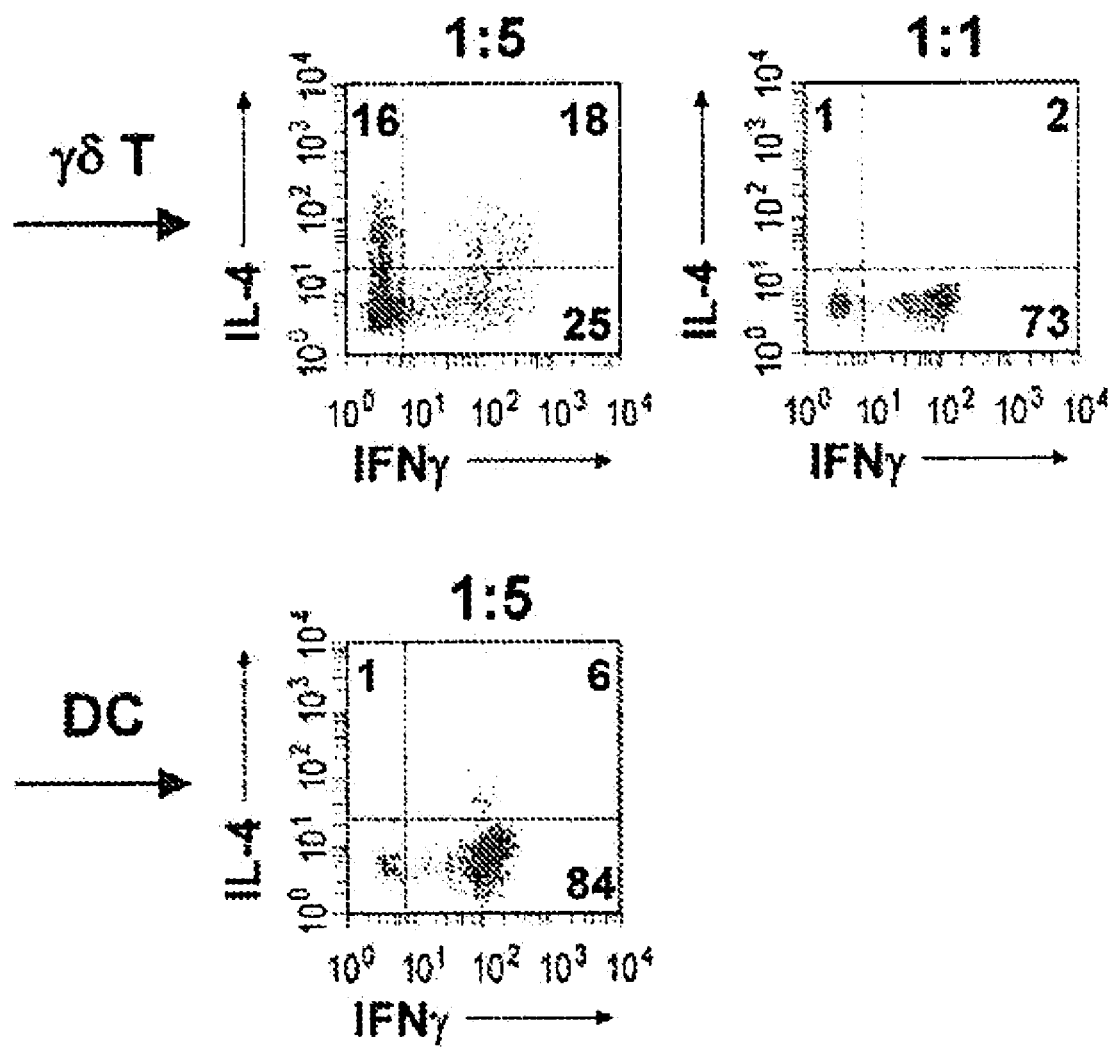

[a] APCs are either 1 day stimulated γδ T cells or mature DCs that are loaded with TSST-1 and added to naïve CD4$^+$ αβ T cells at the ratio of 1:5 or 1:1.
[b] TSST-1 is the antigen used to load the APCs; alternatively, naïve CD4$^+$ αβ T cells are directly activated with PHA in the absence of APCs.
[c] The percent Vβ2$^+$ responder cells is determined by flow cytometry as described in FIG. 10.
[d] The fraction in percent of cytokine polarized Th cells is determined by measuring intracellular cytokines as described in FIG. 13.
[e] Data not determined.

Figure 11:
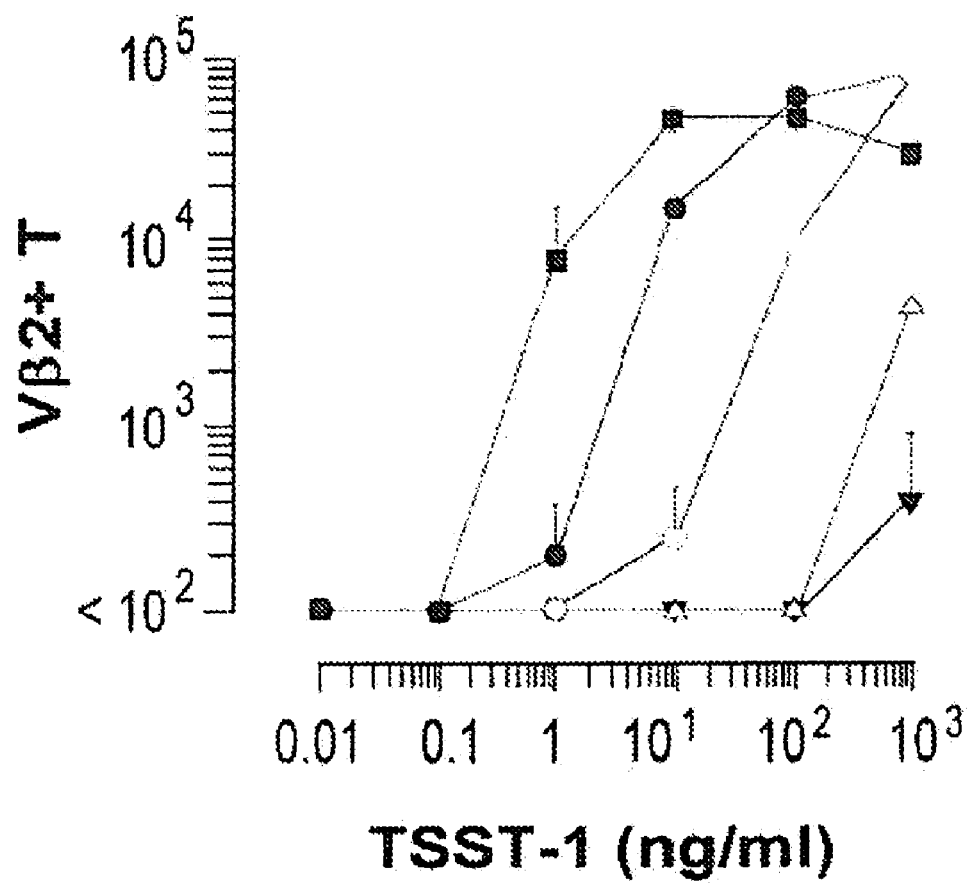
FIG. 11. TSST-1-loaded γδ T cells demonstrate potent APC functions (titration of TSST-1). Stimulated γδ T (γδ T) and αβ T cells (αβ T), dendritic cells (DC) and monocytes (M) are loaded with increasing concentrations of TSST-1 and mixed with CFSE-labeled naïve CD4+ αβ T cells at a ratio of 1:5. After 4 days of culture the number of divided Vβ2+-αβ T cells per culture well (Vβ2+ T) are determined by flow cytometry (see upper-left quadrants in FIG. 10). The antigen-presenting cells tested are those shown in FIG. 10 and, in addition, stimulated γδ T cells that are cultured for 7 days and then loaded with varying concentrations of TSST-1 (γδ T 7d). Each data point plus error bar represents the mean±standard deviation (SD) of duplicate values from 2 separate experiments and data are representative of 3 independent experiments. Cell preparation, TSST-1-loading and flow cytometry are performed according to "Examples".

In addition to co-stimulatory molecules, the parameters that largely determine the kinetics and extent of proliferation in naïve CD4$^+$ αβ T cells are the density of MHC-II-TSST-1 complexes on APCs and the ratio between APCs and responder cells. FIG. 11 shows the proliferation of Vβ2$^+$ naïve responder cells in response to increasing concentrations of TSST-1 that are used to load the different types of APCs. Before addition to naïve CD4$^+$ αβ T cells, the APCs are washed to get rid off excess TSST-1 (see "Examples"). The list of autologous APCs includes 1 day stimulated or 7 day stimulated γδ T cells, mature DCs, freshly isolated monocytes and 1 day stimulated αβ T cells. 1 day stimulated γδ T cells induce T cell proliferation responses at TSST-1 loading concentrations as low as 1 ng/ml and are equally efficient as DCs in terms of maximal responses. The approx. 10-fold higher potency of DCs may be due to their greatly enlarged cell surface area (Miller et al., 2004), which allows more frequent or extensive contacts with responder cells (see also FIG. 6). Of note, substantial proliferation responses are still obtained with stimulated γδ T cells that are expanded during culture for 7 days before loading with TSST-1. Obviously, γδ T cells maintain APC functions over extended periods of time, which is in agreement with the observed conservation of adhesion and co-stimulatory molecules (see also FIG. 1 and Table 1). Monocytes and αβ T cells are >100-fold less potent than γδ T cells. These data demonstrate that stimulated γδ T cells have efficient antigen-presenting functions.

Figure 12:
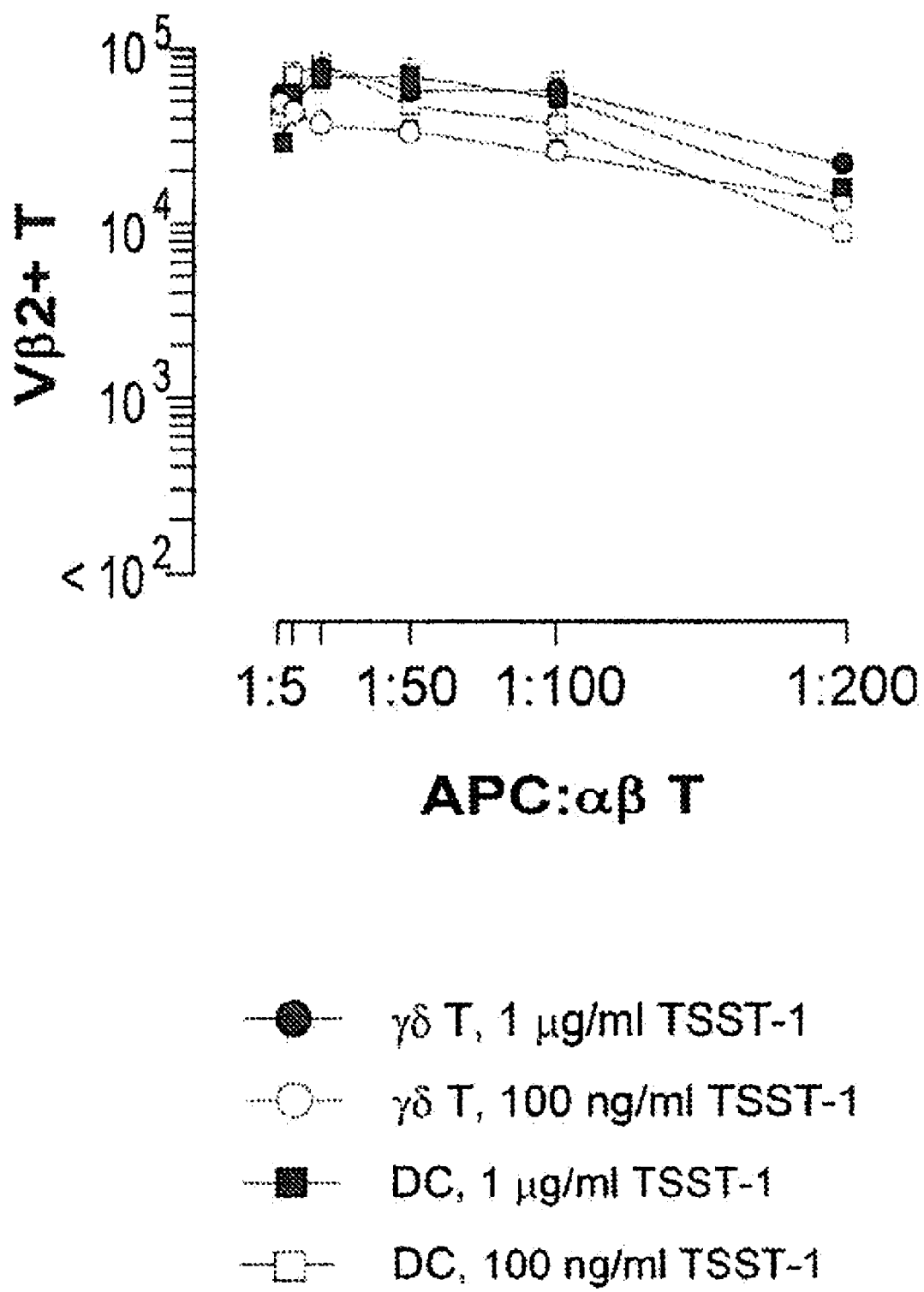
FIG. 12. TSST-1-loaded γδ T cells demonstrate potent APC functions (titration of APCs). Stimulated γδ T cells and mature DCs are loaded with either 1 µg/ml or 100 ng/ml TSST-1 and tested at various dilutions (1:5 to 1:200) of APC:αβ T cells (APC: γδ T cells or mature DCs) for induction of proliferation in naïve CD4+ αβ T cells. Cell preparation, TSST-1-loading and flow cytometry are performed according to "Examples".

In the experiment shown in FIG. 12, instead of titration of TSST-1 during APC loading, the ratio of APCs to naïve responder cells is varied between 1:5 to 1:200 while keeping the TSST-1 loading concentration at 100 ng/ml or 1 μg/ml. Proliferation responses of naïve Vβ2$^+$ CD4$^+$ αβ T cells are determined as in FIG. 11. There is no obvious difference between 1 day stimulated γδ T cells and DCs, and at highest APC dilution (1:200) the proliferation responses still range between 28-40% of maximal responses. These data further illustrate the proficiency of γδ T cells as efficient APCs.

Primary immune responses involve the differentiation of naïve CD4$^+$ T cells into polarized Th1, Th2 or Th0 cells with the capacity to produce type 1 (IFN-γ), type 2 (IL-4) or type 0 (IFN-γ+IL-4) cytokines, respectively. Naïve CD4$^+$ T cells have the capacity to differentiate into either one of these polarized Th cells. T cell polarization is determined by the co-stimulatory environment provided by APCs at the time of naïve T cell priming. Efficient APCs not only induce proliferation of naïve T cells but also support their differentiation into effector cells. FIG. 13 demonstrates that stimulated γδ T cells are fully capable of presenting TSST-1 in the proper context of co-stimulation for the generation of effector Th cells. 4 days after priming with TSST-1-loaded γδ T cells, most Vβ2+ naïve CD4+ T cells have responded by proliferation and expression of the memory marker CD45RO. After 21 days of culture the majority of cells return to a resting state, uniformly express CD45RO and consist of Vβ2+ T cells (Table 3). Importantly, the majority of cells produce cytokines typical of either Th1, Th2 or Th0 cells, and Th1 polarization is further enhanced by increasing the ratio of TSST-1-loaded γδ T cells and responder cells to 1:1. Again, the more prominent effect seen with DCs may be due to morphological criterion as discussed above (Miller et al., 2004) (see also FIGS. 6, 9). By contrast, antigen-unselective activation (phytohemagglutinin) does not result in selective expansion of Vβ2+ T cells (Table 3), and stimulated αβ T cells fail to induce CD45RO expression and proliferation of naïve CD4+ αβ T cells (FIG. 13).

Figure 14:
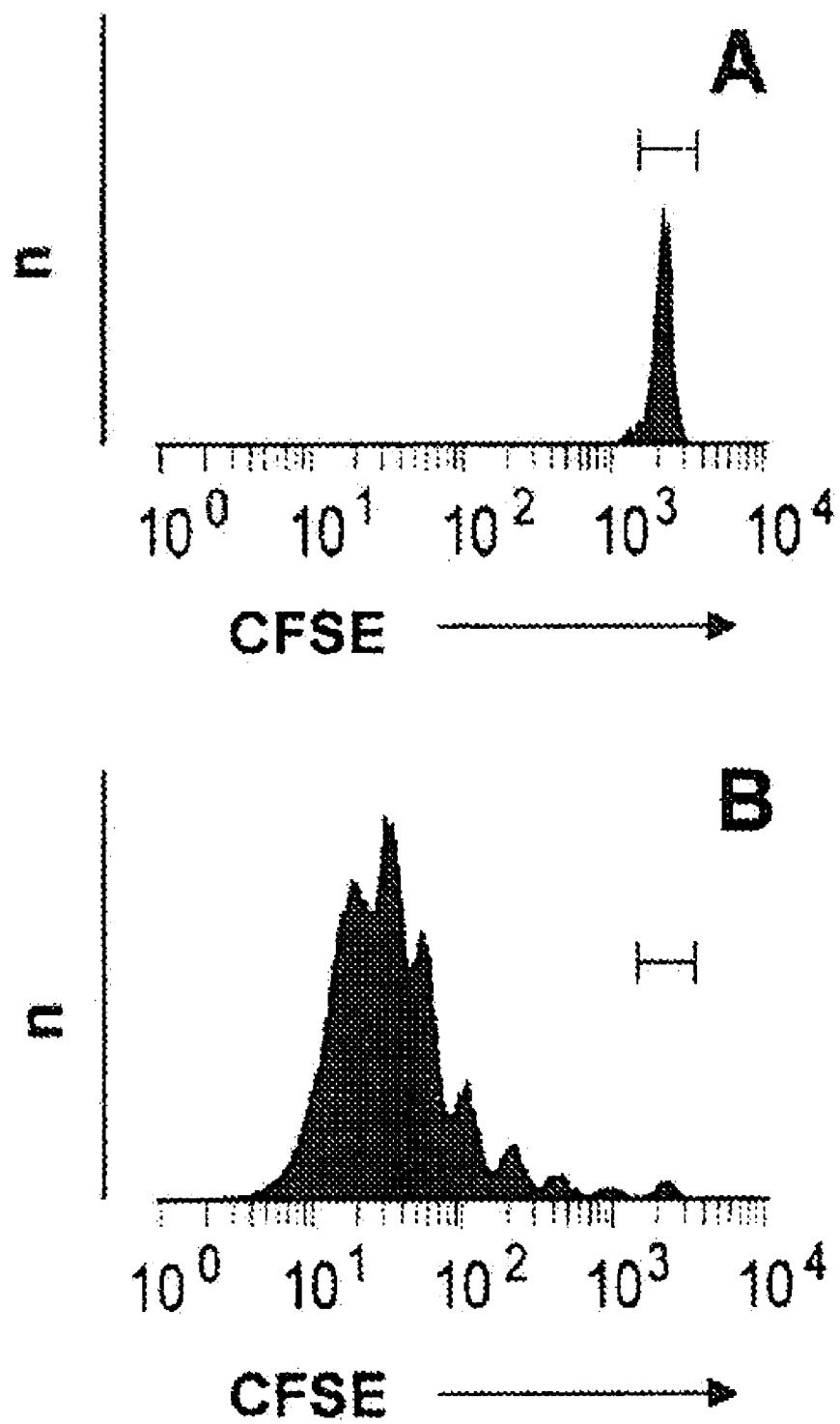
FIG. 14. Induction of proliferation in naïve CD4+ αβ T cells by TSST-1-loaded γδ T cells is cell contact-dependent. Stimulated γδ T cells are loaded with 100 ng/ml TSST-1 and CFSE-labeled naïve CD4+ αβ T cells are cultured alone (A) or together (B) with γδ T cells at an APC:responder cell ratio of 1:5. The two-chamber culture system and the CFSE flow cytometry data analysis is described in FIG. 5.

As seen with TT-specific and PPD-specific CD4+ αβ T cells (see e.g. FIG. 5), induction of responses in naïve CD4+ αβ T cells is fully dependent on cell-to-cell contact with TSST-1-loaded γδ T cells (FIG. 14). Stimulated γδ T cells induce strong antigen-specific responses in naïve CD4+ αβ T cells and support their proliferation and differentiation in a manner typical for efficient APCs.

Figure 15:
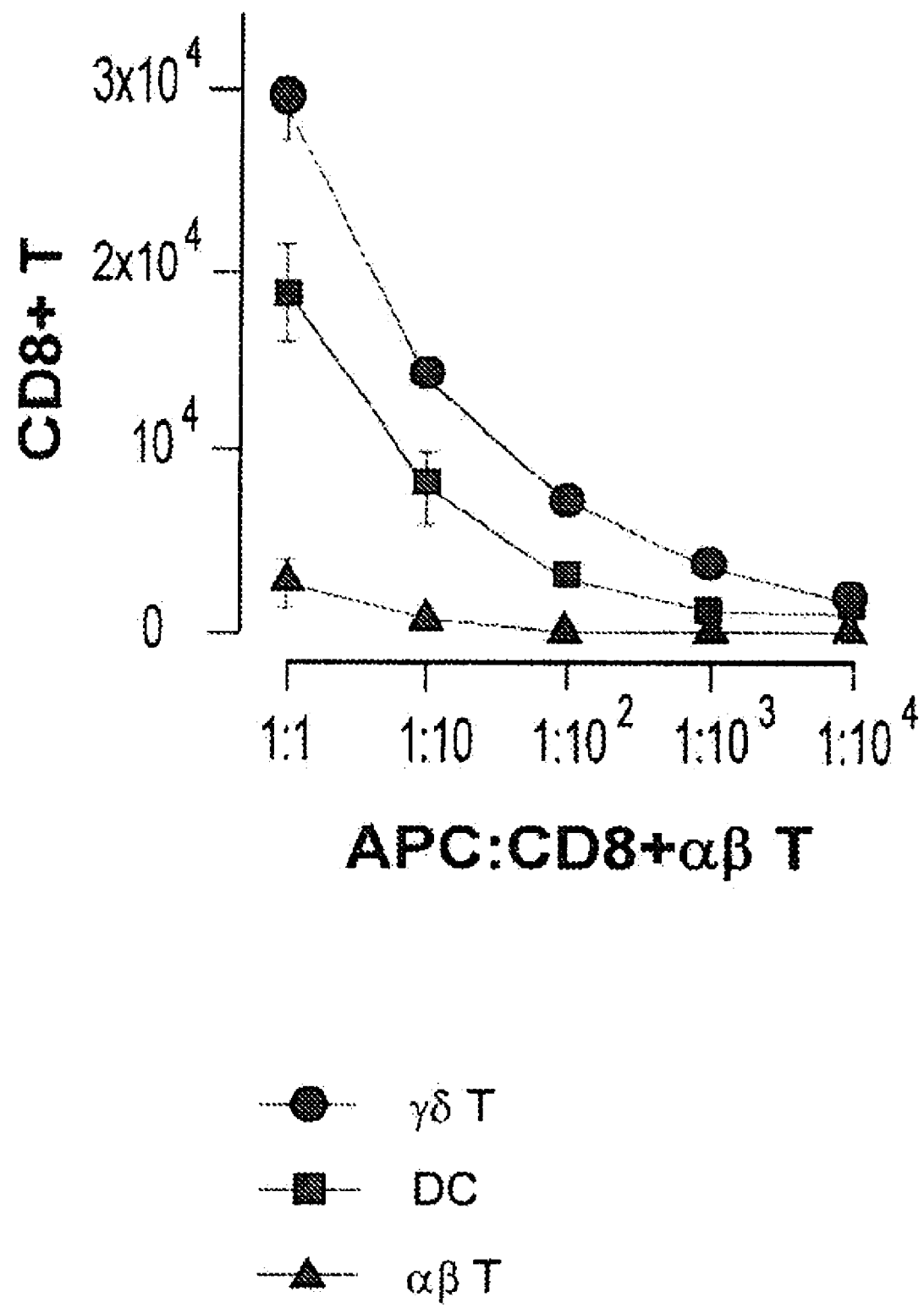
FIG. 15. γδ T cells induce primary CD8+ T cell responses. Mixed-leukocyte responses with naïve, CD8+ αβ T cells and heterologous IPP-stimulated γδ T cells (circles), LPS-matured, monocyte-derived DCs (squares) or superantigen-stimulated αβ T cells (triangles) at decreasing APC:responder cell ratios (representative of 6 experiments). Proliferation responses in CFSE-labeled CD8+ responder cells were assessed by flow cytometry data analysis as described in FIG. 5.
Figure 16A:
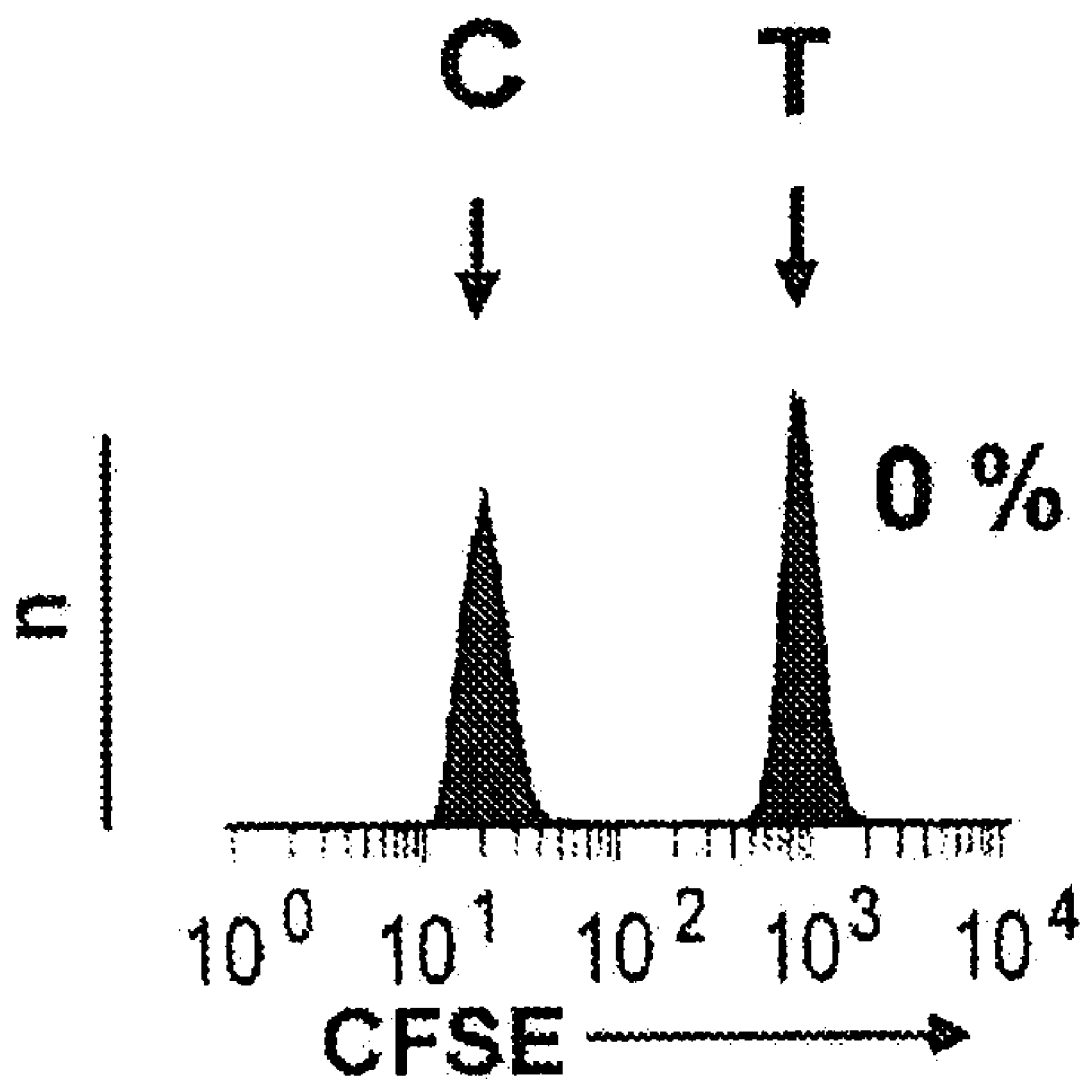
FIG. 16. γδ T cells induce differentiation of naïve CD8+ T cells into cytotoxic T cells. CD8+ T cells derived from mixed-leukocyte responses, as described in FIG. 15, were examined after 14 days of culture for cytolytic activity. The cytotoxicity assay included effector cells, i.e. CD8+ T cells derived from mixed-leukocyte responses, and CFSE-labeled target cells. The mixture of target cells contained true target cells (heterologous CD4+ T cells) and negative control target cells (autologous CD4+ T cells) at a 1:1 ratio. True and negative control target cells were labeled with different concentrations of CFSE before mixing in order to discriminate between the two target cell subsets. (A) Flow cytometric analysis of the target cell mixture in the absence of effector cells shows the negative control (C) and true target (T) cell populations. (B) After 12 h of co-culture of CD8+ T cells and target cells at ratios of 30:1, 10:1, 3:1, and 1:1, the degree of target cell lysis was assessed by measuring the decrease in number in the true target cell population (arrow). The numbers by the arrows refer to percent specific killing and relate to loss of cell counts with high CFSE fluorescence (true target cells) as compared to control cell counts with low CFSE fluorescence. Left column: CD8+ T cells were derived from mixed-leukocyte responses with IPP-stimulated γδ T cells as APCs. Right column: CD8+ T cells were derived from mixed-leukocyte responses with mature DCs as APCs.
Figure 16B:
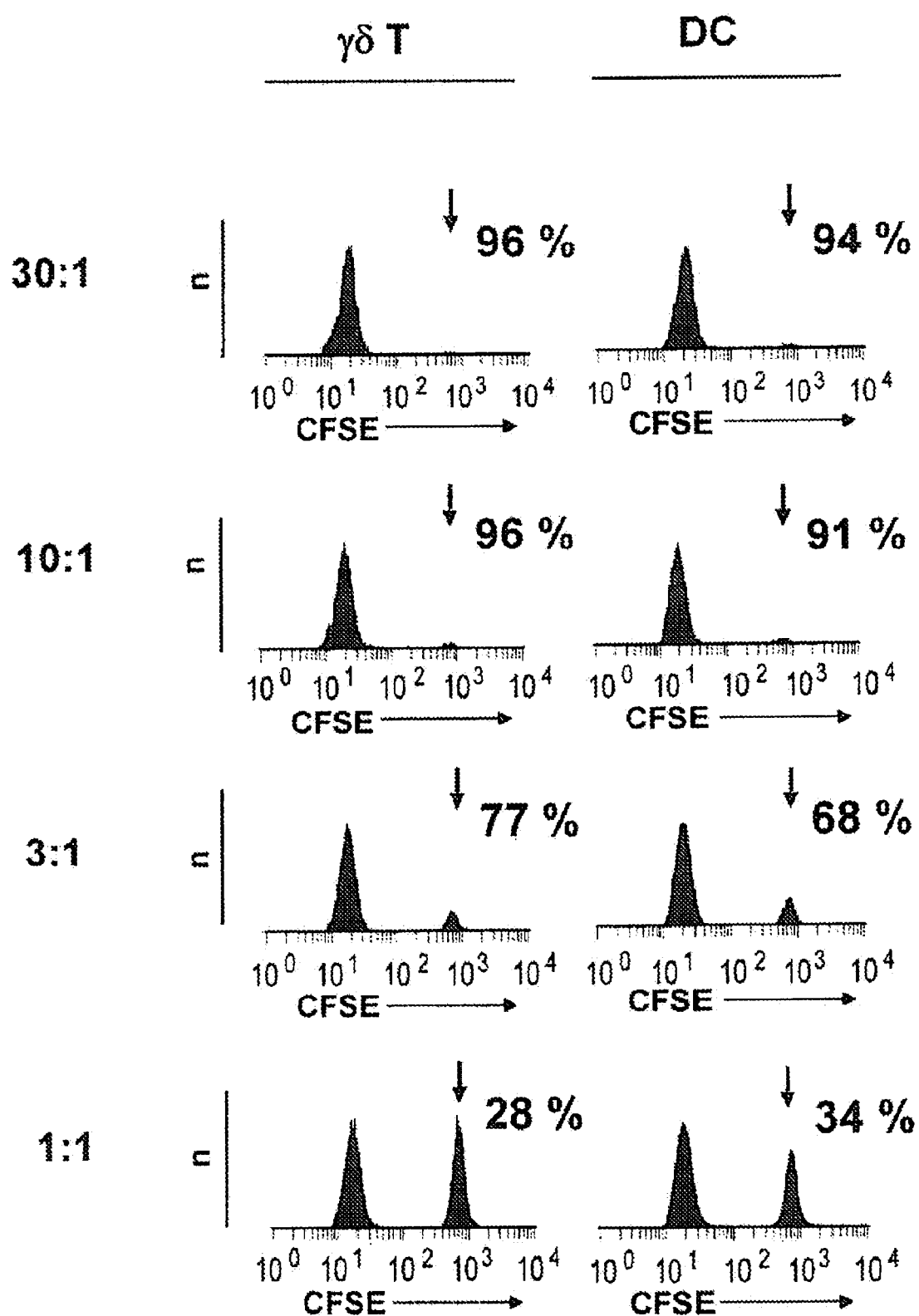
Figure 17:
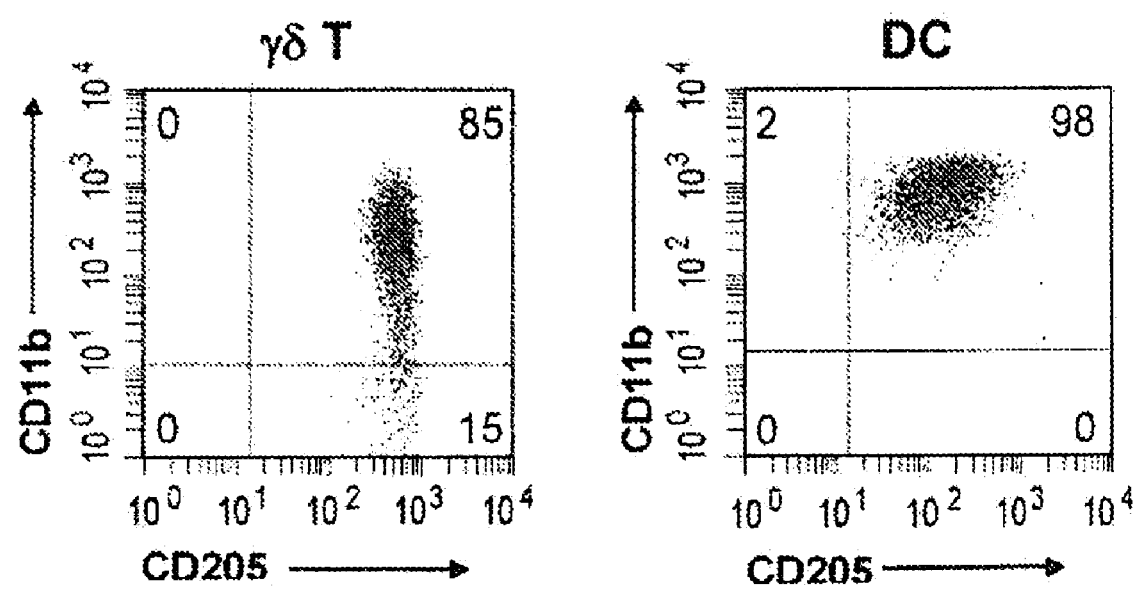
FIG. 17. γδ T cells express high levels of the endocytic cell surface proteins DEC205 (CD205) and CD11b. γδ T cells freshly isolated from peripheral blood (γδ T) and immature DCs (DC) were analyzed for CD205 and CD11b expression by flow cytometry as described in FIG. 7. Vertical and horizontal lines in the dot-blots figure define the gates for CD205 or CD11b-expressing cells, and the right-upper quadrants in the figure depict cells double-positive for CD205 and CD11b; the numbers refer to the percent of total cells present within the individual quadrants. Positivity is defined by staining with isotype-matched control antibodies, and horizontal or vertical lines represent the gates for 99% background stainings.

CD4+ T cells recognize MHC class II-peptide complexes on APCs whereas CD8+ T cells recognize MHC class I-peptide complexes on APCs. MHC class I molecules are ubiquitously expressed on blood and tissue cells; therefore, all cells in the body are potential target cells for CD8+ T cells. Of note, CD8+ T cells are crucial players in the defense against viral infections and tumors and, frequently, successful vaccination depends on the generation of antigen-selective, cytotoxic CD8+ T cells. FIG. 15 documents that Vδ2+ T cells are highly potent APCs in the induction of primary CD8+ T cell responses. Naïve, untouched CD8+ αβ T cells are used as responder cells in proliferation assays containing IPP-stimulated γδ T cells, mature DCs or superantigen-stimulated αβ T cells as APCs (all from the same donor). γδ T cells fully match or are even better as DCs in induction of CD8+ T cell proliferation, and αβ T cells are inferior APCs. FIG. 16 documents that γδ T cells induce the differentiation of cytotoxic effector T cells. The data illustrate that γδ T cells are indistinguishable from DCs in driving the differentiation of naïve CD8+ T cells into alloantigen-specific, cytotoxic T cells. Collectively, TCR-stimulated Vδ2+ T cells induce strong proinflammatory responses in both naïve CD4+ and CD8+ αβ T cells in a professional APC-like manner.

γδ T cells also express endocytic receptors, such as the C-type lectin DEC-205 (CD205) and the integrin subunit CD11b with selectivity for multiple protein and non-protein ligands. CD205 and CD11b are known to be highly expressed on DCs (Banchereau and Steinman, 1998; Steinman et al., 2003; Banchereau et al., 2004). FIG. 17 documents that γδ T cells, similar to DCs, inherently express high levels of these endocytic receptors. In analogy to novel methods of antigen-delivery to DCs, these data demonstrate that antigens, including protein vaccines for tumors and infectious agents, can also be targeted to γδ T cells for in vivo antigen processing and presentation.

These experimental details prove that the method of the invention for the preparation of efficient antigen-presenting human γδ T cells comprising selecting γδ T cells out of human peripheral blood mononuclear cells, treating the selected cells with a stimulus for induction of antigen-presenting functions, and applying the antigen to the stimulated cells provides ACPs comparable to DCs.

In particular, the invention concerns such a method for the preparation of efficient antigen-presenting human γδ T cells wherein selecting γδ T cells is performed by magnetic cell sorting with antibodies to human VγVδ-T cell receptors. Alternatively, selecting γδ T cells is performed by culturing freshly isolated peripheral blood lymphocytes in the presence of structurally defined small molecular weight non-peptide compounds that induce the selective expansion of Vγ2Vδ2+-T cell receptor chain-expressing γδ T cells, for example in the presence of IPP, e.g. as presented by B cells or substitutes.

The invention further concerns the particular method wherein the stimulus for induction of efficient antigen-presenting functions is a small molecular weight non-peptide compound or a substitute or phytohemagglutinin, and the particular method wherein the antigen is applied in the form of defined proteins, undefined protein mixtures, or crude or enriched extracts from tumor and infected cells, for example wherein the antigen applied is a pathogen- or tumor cell-derived peptide, or a pathogen-derived protein which is applied in the form of DNA or RNA encoding it under conditions allowing endogenous expression of said pathogen-derived protein, in particular in the form of purified DNA or RNA or a delivery vector containing such DNA or RNA. If the antigen is in the form of a DNA or RNA conditions are selected such that said DNA or RNA may be properly expressed. Application of an antigen may occur before, during or after γδ T cell stimulation for induction of antigen-presenting functions. If an antigen is applied as a peptide (protein fragment), its application may also be after stimulation in a separate step termed "peptide loading".

The efficient antigen-presenting human γδ T cells prepared according to the invention as described hereinbefore may be used in immunotherapy. Such use may be similar to the known use of DCs in immunotherapy, thereby overcoming the drawbacks of the use of DCs such as scarcity in peripheral blood, inability to proliferate in vitro, heterogeneity and functional instability.

In particular, the efficient antigen-presenting human γδ T cells prepared according to the invention as described hereinbefore may be used for the manufacture of a medicament (pharmaceutical composition) for use in immunotherapy.

The present invention relates also to pharmaceutical compositions that comprise the efficient antigen-presenting human γδ T cells prepared according to the invention as described hereinbefore, and that can be used especially in the treatment of the diseases mentioned hereinbefore and hereinafter. Compositions for parenteral administration, such as intravenous, intramuscular, subcutaneous, mucosal or submucosal administration, to humans are especially preferred. The compositions comprise the cells together with a pharmaceutically acceptable carrier. The dosage of the cells of the Invention depends upon the disease to be treated and upon the age, weight, and individual condition, the individual pharmacokinetic data, and the mode of administration. The pharmaceutical compositions comprise from approximately 0.01% to approximately 50% of the cells of the invention. Unit dose forms are, for example, ampoules or vials.

Preference is given to the use of isotonic aqueous suspensions. The pharmaceutical compositions may comprise excipients, for example preservatives, stabilizers, wetting agents and/or emulsifiers, solubilizers, salts for regulating osmotic pressure and/or buffers and are prepared in a manner known per se, for example by means of conventional mixing processes. The manufacture of injectable preparations is usually carried out under sterile conditions, as is the filling, for example, into ampoules or vials, and the sealing of the containers.

The invention further relates to a method of treatment of tumors or chronic or recurrent infectious diseases wherein efficient antigen-presenting human γδ T cells are injected into a patient in need thereof. In particular the method involves single or repeated applications of said γδ T cells, e.g. pharmaceutical compositions containing same, by intradermal, subcutaneous, intramuscular, intravenous, mucosal or submucosal routes.

In the method of treatment of tumors γδ T cells are used, which have been stimulated in the presence of defined tumor proteins or crude (undefined) tumor cell extracts or, alternatively, which have been obtained using treatment with recombinant RNA/DNA technologies that are routinely used for transfection or transduction of live blood or tissue cells. Preferably, if defined tumor peptides for direct loading onto cell surface MHC molecules are known, then such peptides are added to stimulated γδ T cells, incubated, washed and immediately used for therapy. It is important to emphasize that the number of γδ T cells used per administration as well as the route and frequency of γδ T cell administration depend on the efficacy in immune response induction by the individual tumor antigen used as well as the type and location of the tumor present in the individual patient. Preferred protocols are, for example, $1\text{-}20 \times 10^6$ cells/0.5-2 ml per administration with 1 to 6 follow-up administrations with the same or lower amounts of cells at two-weeks to two-months intervals.

In the method of treatment of chronic or recurrent infectious diseases γδ T cells are used which have been stimulated in the presence of defined infectious agents, preferably in attenuated form, or crude (undefined) infected cell extracts or, alternatively, which have been obtained using treatment with recombinant RNA/DNA technologies that are routinely used for transfection or transduction of live blood or tissue cells. The preferred treatment protocol corresponds to the one described above.

The Invention further relates to a method of vaccination against tumors or chronic or recurrent infectious diseases wherein efficient antigen-presenting human γδ T cells, to which non-infectious and non-tumorigenic antigens have been applied, are injected into a patient to be vaccinated. For vaccination purposes the same procedures are applied as described hereinbefore but wherein γδ T cells are used to which non-infectious and non-tumorigenic antigens have been applied. The preparation of vaccine antigen-presenting γδ T cells and administration of these cells for the vaccination of patients against tumor antigens or infectious agents follows the description of tumor immunotherapy (see above). Preferred protocols are those currently employed in DC-based vaccination treatments. The immune status of such treated patients, i.e. the quality (efficacy, kinetics, etc.) of the vaccine responses, is examined as described below.

The invention further relates to another method of (prophylactic or therapeutic) vaccination against tumors or vaccination against agents inducing infectious or non-infectious diseases, comprising the administration of γδ T cell-targeting vaccines to individuals. Preferably, such γδ T cell-targeting vaccines are hybrid compounds composed of vaccine agents and γδ T cell-targeting molecules. γδ T cell-targeting molecules are antibodies or ligands specific for endocytic receptors on γδ T cells, including but not limited to CD11b and CD205. Vaccine agents are proteins or related molecules against which an immune protection is desired.

Administration of γδ T cell-targeting vaccines entails the repeated treatment of individuals with γδ T cell-targeting vaccines by means of injections, oral administrations or any other protocol of vaccine delivery yielding optimal immune protection.

The invention further relates to a method of identification of novel tumor or pathogen-derived antigens comprising selecting γδ T cells out of human peripheral blood mononuclear cells, treating the selected cells with a stimulus for induction of efficient antigen-presenting functions, applying fractions of an undefined protein mixture, or crude or enriched extracts from tumor and infected cells, or RNA or DNA libraries derived from tumors and infectious agents, testing for in vitro activation of autologous naïve αβ T cells, and comparing the activation results of different antigen fractions.

In this method, γδ T cells are used as in vitro screening tools for the Identification of novel and improved antigens for use in therapeutic and prophylactic vaccinations. Isolating, selecting and stimulating γδ T cells are performed as described in the method of preparation of efficient antigen-presenting human γδ T cells. In the step of applying antigens, fractions of crude antigen preparations (e.g. cell extracts or undefined mixtures) or RNA/DNA libraries derived from tumors and infectious agents are used. Such prepared γδ T cells are then tested for activation of naïve αβ T cells from the same donor, i.e. autologous αβ T cells. Read-outs in these in vitro immune response assays are proliferation and cytokine production in αβ T cells, or any other simple measurement of αβ T cell activation. Culture conditions are preferably those described above for αβ T cell responses to TSST-1-presenting γδ T cells in FIGS. 10-14 and the "Examples". When comparing activation results from different antigen fractions, improved αβ T cell responses indicate that the antigen sources are "enriched" in terms of immunogenicity. Corresponding "enriched" fractions are further processed, and the whole cycle of experimental steps repeated with the further fractionated antigens. Eventually, repeated fractionation of "enriched" antigen sources (protein or DNA library fractionation) leads to single proteins with maximal immunostimulatory functions. Such novel proteins may be further manipulated by proteolytic cleavage, and cleavage mixtures analyzed accordingly for the generation of (small) immunogenic peptides for direct loading onto APCs.

The invention further relates to a method of diagnosing the immune competence of a patient comprising selecting γδ T cells out of the patient's peripheral blood mononuclear cells, treating the selected cells with a stimulus for induction of efficient antigen-presenting functions, applying the antigen for which the immune competence has to be determined, and testing for in vitro activation of autologous αβ T cells.

In this method, γδ T cells and their impact on antigen-specific memory αβ T cells from the same donor are used as in vitro tools for the diagnosis of the immune competence of a patient with regard to a particular antigen and for determination whether a vaccination has been successful. Isolating, selecting and stimulating γδ T cells are performed as described in the method of preparation of efficient antigen-presenting human γδ T cells. In the step of applying antigens, the particular antigen for which immune competence has to be determined, is applied to stimulated γδ T cells. Culture conditions and read-outs for determination of αβ T cell responses (in vitro immune response assays) are preferably those described above for αβ T cell responses to TSST-1-presenting γδ T cells in FIGS. 10-14 and the "Examples". The decisive difference is that memory αβ T cells instead of naïve αβ T cells are monitored for enhanced immune responses (proliferation, cytokine production, etc.) during stimulation with antigen-presenting γδ T cells. Successful immunotherapy (vaccination) leads to the generation of antigen-specific effector/memory T cells, which will give many fold improved immune responses during in vitro monitoring of immune status as compared to naïve αβ T cells. These assays are preferentially performed with bulk (unfractionated) αβ T cells, since antigen-specific memory αβ T cells are highly enriched in successfully vaccinated individuals.

EXAMPLES

| Abbreviations | |
|---|---|
| DC | dendritic cell |
| LN | lymph node |
| PP | Peyer's patch |
| TCR | T cell antigen receptor |
| BCR | B cell antigen receptor |
| MHC | major histocompatibility complex |
| APC | antigen-presenting cell |
| Vδ1* T cells | Vδ1*-TCR chain expressing γδ T cells |
| Vγ2Vδ2* T cells | Vγ2Vδ2*-TCR chain expressing γδ T cells |
| IPP | isopentenyl pyrophosphate |
| TT | *Clostridium tetani* tetanus toxin |
| PPD | *Mycobacterium tuberculosis* purified protein derivative |
| TSST-1 | *Staphylococcus aureus* toxic shock syndrome toxin 1 |
| PHA | phytohemagglutinin |
| IFN-γ | interferon-γ |
| TNF-δ | tumor necrosis factor-α |
| IL | interleukin |
| FACS | fluorescence-activated cell sorter |
| MFI | mean fluorescence intensity |
| SD | standard error |
| CFSE | carboxyfluorescein diacetate succinimidyl ester |

1. Cell Isolation and Generation

γδ T Cells

Blood was obtained from healthy volunteers aged between 28 and 42 years. Human peripheral blood mononuclear cells (PBMCs) were isolated from heparin-treated donor blood buffy coats or fresh blood by Ficoll-Paque centrifugation according to standard protocols (Brandes et al., 2003). Out of PBMCs, γδ T cells were positively selected with antibodies to human VγVδ-TCRs using the magnetic cell sorting system from Miltenyi Biotec. In this way, 50 ml of fresh blood routinely yielded 2-5×10$^6$ cells with a purity of 98-99% γδ T cells.

Naïve αβ T Cells

With regard to CD8$^+$ αβ T cell response assays, donors were screened for HLA-A2 expression by flow cytometry with the allele-specific mAb BB7.2 (23, 45), and further subtyped for *0201 by PCR. Untouched, naïve CD4$^+$ or CD8$^+$ αβ T cells (98-99% purity) were isolated from PBMCs by negative magnetic cell sorting with specific antibodies to VγVδ-TCR, CD1c, CD14, CD16, CD19, CD25, CD45RO, CD56, HLA-DR plus CD4 or CD8, respectively, followed by fluorescence-activated cell sorting of cells that stained negative for these markers.

αβ T Cell Lines

From PBMCs CD4$^+$ αβ T cells were positively selected with antibodies to human CD4 by means of the magnetic cell sorting. CD4$^+$ αβ T cells were stimulated with TT- or PPD-presenting autologous, irradiated (30 Gy) PBMCs at a ratio 1:100 in the first and 1:10 in the following cycles, and were expanded in IL-2 containing medium. Antigen-specificity was verified by a CFSE-based proliferation assay (see below) after three cycles of antigenic selection and expansion.

B Cells

B cells were isolated by negative magnetic cell sorting out of PBMCs. B cells were either used directly for γδ T cell stimulation (see below), or B cell lines were generated by EBV-induced transformation following standard protocols and then used for γδ T cells stimulation.

Monocytes

Monocytes were isolated by positive magnetic cell sorting from PBMCs with antibodies to human CD14, and stringent washing of the separation columns before elution of magnetically trapped cells resulted in enrichment of CD14$^{high}$ monocytes.

DCs

Monocyte-derived DCs were generated by culturing CD14$^{high}$ cells in medium containing 10% FCS in the presence of IL-4 (10 ng/ml) and GM-CSF (25 ng/ml). After 6-7 days of culture the majority of cells were immature, as assessed by cell surface staining for HLA-DR, CD1a, CD14, CD80, CD83, CD86 and CCR7. DC maturation was induced by further culture for 8 hours in the presence of 100 ng/ml LPS (from *Salmonella abortus equi*) (Langenkamp et al., 2000). DC maturation was confirmed by flow cytometry staining for cell surface DC maturation markers HLA-DR, CD80, CD83, CD86 and CCR7.

2. T Cell Stimulation

γδ T Cells

50 μM isopentenyl pyrophosphate (IPP) presented by heterologous or autologous EBV-transformed B cell lines or primary B cells at a dilution of 1:10 were used to activate resting (freshly isolated) γδ T cells as described (Brandes et al., 2003). γδ T cells were cultured in medium supplemented with 8% human serum in the presence of IL-2 (20 or 200 IU/ml).

αβ T Cells

Positive selected αβ T cells were activated on plates coated with 10 μg/ml anti-CD3 antibody (OCT3) plus 250 ng/ml anti-CD28 antibody (28.2) or, alternatively, with 10 ng/ml phorbol 12-myristate 13-acetate (PMA) plus 1 μg/ml ionomycin or, alternatively, with 1 μg/ml PHA, and cultured in medium supplemented with 8% human serum in the presence of IL-2 (200 IU/ml).

3. Carboxyfluorescein Diacetate Succinimidyl Ester (CFSE) Labeling

Cells were washed with PBS$^-$ and labeled with 2.5 μM CFSE (Molecular Probes, Eugene, Oreg.) in PBS$^-$ supplemented with 1% FCS for 4 min at room temperature. Labeling was stopped by repeated washing of the cells with ice-cold PBS supplemented with 5% FCS. The CFSE-labeled cells were immediately used in cell activation and proliferation assays.

4. APC Preparation and Antigen Loading.

γδ T-APCs and monocyte-derived DCs were generated as described (Brandes et al., 2005). For preparation of γδ T-APCs, purified γδ T cells were stimulated with 50 μM isopentenyl pyrophosphate (IPP) (Sigma-Aldrich) presented by either primary B cells or HLA-A2*0201 negative EBV-B cell lines (Brandes et al., 2005). Alterations of DCs preparations included culturing of CD14$^{high}$ cells in 100 ng/ml IL-15 and 50 ng/ml GM-CSF as described elsewhere (Mohamadzadeh et al., 2001) as opposed to the standard procedure involving 10 ng/ml IL-4 and 50 ng/ml GM-CSF for 6-7 days. Maturation for 8 h was initiated by applying a combination of shear force (cluster disruption by pipetting) and 1 μg/ml LPS (from *Salmonella abortus equi*, Sigma) or by culturing of DCs with CD40L-expressing J558L cells at a 1:2.5 ratio (CD40L DC) (Delamarre et al., 2003; Salio et al., 2001; Lane et al., 1995). Control B cells consisted of purified autologous B cells that were γ-irradiated with 40 Gy (just as before use as "feeder cells" during γδ T cell activation), washed, incubated for 18 h with IPP in the presence or absence of M1, then γ-irradiated with 9-10 Gy and washed; these control B cells were included in some experiments as control-APCs.

For loading of intact protein (performed in standard culture medium), antigen was added at indicated concentrations 2 h before initiation of Vγ9Vδ2 T cell-activation by IPP or induction of DC maturation. In some experiments, Brefeldin A and Lactacystin were added 2 h before protein antigen was added to Vγ9Vδ2 T cells and DCs. For peptide pulsing, APCs including 18 h IPP-stimulated γδ T-APCs, 5 h matured DCs, monocytes or control B cells were washed extensively with serum-free medium, then incubated for 3 h in this medium supplemented with the peptides at indicated concentrations. APCs were γ-irradiated (9-10 Gy for γδ T-APCs, 26 Gy for Monocytes, and 30 Gy for DCs) and extensively washed before co-culture with responder cells. APCs were not γ-irradiated before use when used in assays measuring short-term responses, i.e. monitoring the IFN-γ production in peptide selective CD8$^+$ T cell clones.

5. In Vitro Antigen-Presentation Assays

Antigen Presentation to αβ T Cell Lines

Blood γδ T cells were activated by the IPP-presenting and irradiated (100 Gy) heterologous EBV-B cell line CP-EBV (see above) for 24 to 60 hours in the presence of 10-20 μg/ml TT (Berna Biotech, Bern, Switzerland) or 20 μg/ml PPD (Statens Serum Institut Copenhagen, Denmark). Monocyte-derived DCs were cultured with TT or PPD for the same period of time and matured for the last 8 hours (see above). After irradiation (26 and 40 Gy for γδ T cells and DCs, respectively) and intensive washing, these APCs were used to stimulate TT- and PPD-specific CD4$^+$ αβ T cells clones at a ratio of 1:5 (if not indicated otherwise). At various time points of culture responder cells were examined by flow cytometry for expression of activation markers (HLA-DR, ICOS, and CD25), TCR internalization (loss of cell surface CD3) and cell proliferation (reduction in CFSE fluorescence signals).

Priming of Naïve CD4$^+$ αβ T Cells

Following stimulation of γδ T cells and αβ T cells or following maturation of monocyte-derived DCs or following isolation of monocytes from PBMCs, these potential APCs were pulsed for 1 hour at 37° C. with various concentrations of toxic shock syndrome toxin (TSST-1) (Toxin Technology, Sarasota, Fla.). Then, the potential APCs were irradiated with 12 Gy (or 40 Gy for DCs), extensively washed and mixed (routinely at a ratio 1:5) with CFSE-labeled naïve CD4$^+$ αβ T cells. Generally, 96-well round bottom plates contained $8\times10^3$ APCs and $4\times10^4$ CFSE-labeled responder cells in culture medium without exogenous cytokines. Cell proliferation was analyzed after 4 days by flow cytometry.

In Th cell differentiation assays, 100 IU/ml IL-2 was added on day 5 of culture, and cells were expanded during subsequent 10-16 days until responder cells ceased to proliferate and returned to a resting state (Langenkamp et al., 2000). At day 21, Th cell differentiation was examined by measuring intracellular cytokine production. Cells were stimulated for 6 hours with PMA/ionomycin in the presence of 10 μg/ml Brefeldin A (Sigma-Aldrich), then fixed with 2% paraformaldehyde, permeabilized with 0.5% saponin in PBS containing 2% FCS, stained with antibodies to IL-2, IFN-γ, IL-4 and Vβ2-TCR, and analyzed by flow cytometry.

Priming of Naïve CD8$^+$ αβ T Cells

In mixed-leukocyte responses, irradiated, IPP-stimulated γδ T cells, superantigen-activated αβ T cells or LPS-matured DCs were co-cultured with heterologous CFSE-labeled naïve CD8$^+$ αβ T cells. Generally, 96-well round bottom plates contained $4\times10^4$ CFSE-labeled responder cells and APCs in the range of $4\times10^4$ cells to 4 cells per well, corresponding to APC:responder cell ratios of 1:1 to 1:10,000. Cell proliferation was analyzed after 6 days of culture by flow cytometry. CD8$^+$ effector cell generation was evaluated, after 14 days of mixed-leukocyte responses with naïve CD8$^+$ αβ T cells, in a cytolytic assay, involving co-culture for 12 h with a mixture of heterologous (true targets) and autologous (negative control) CO4$^+$T cells labeled with high (1 μM) and low dose (0.05 μM) of CFSE, respectively, followed by flow cytometry analyzing CFSE signals. Reduction in the counts of true target cells indicated antigen-specific killing by CD8$^+$ effector cells whereas reduction in the counts of negative control cells indicated unspecific target cell killing by CD8$^+$ effector cells.

6. Antigen Presentation Assays.

CD8$^+$ αβ T cell proliferation responses were determined as described above for CF4+ αβ T cells by using CFSE-labeled (2.5 μM, 4 min in 1% FCS) bulk αβ T cells or purified naïve CD8$^+$ T cells from healthy donors. Studies on the cross-presentation of Influenza Matrix protein M1 and Melan-A protein were done on a HLA-A*0201 background. Peptide HLA-A*0201 tetramer complexes are available for the immunodominant peptides M1p58-66 and Melp26-35 from M1 and Melan-A, respectively. The antigen-specific proliferation or the acquisition of an antigen-experienced phenotype of M1p58-66 or Melp26-35 tetramer binding cells derived from bulk or naïve CD8$^+$ αβ T cell preparations was measured by flow cytometry after 10 days of coculture. Of note, exogenous IL-2 (20 U/ml to bulk and 200 U/ml to naïve CD8$^+$ cultures) was added 48 h after initiation of the cocultures. In addition, M1p58-66 tetramer binding cells derived from naïve CD8$^+$ αβ T cell preparations (after 2 cycles of 10-day-cocultures with γδ T-APCs or DCs) were sorted, further cultured or cloned by limiting-dilution to be analyzed in more detail for their preferential TCR composition and their functionality, i.e. their ability to specifically recognize and kill peptide pulsed, HLA-A2 target cells or produce cytokines. Alternatively, antigen-presentation was monitored by intracellular detection of IFN-γ produced in CD8$^+$ T cell clones specific for the relevant peptides (FLUMA55 for M1p58-66, and LAU337 6B7 for Melp26-35).

7. Culture Media

The medium used throughout was RPMI 1640 supplemented with 2 mM L-glutamine, 1% nonessential amino acids, 1% sodium pyruvate, 50 μg/ml penicillin/streptomycin, $5\times10^{-5}$ M 2-mercaptoethanol (GIBCO Life Technologies, Switzerland) and either 10% FCS (Hyclone Laboratories, Logan, Utah, or GIBCO BRL) or 8% human serum (Swiss Red Cross, Bern, Switzerland). Human recombinant IL-2 was obtained from IL-2 transfected myeloma cultures. I.e., a myeloma-based expression system, and human recombinant IL-4, IL-15 and GM-CSF were purchased (PeproTech, London, U.K.).

8. Flow Cytometry

Cell Preparation

Cells were washed twice in ice-cold PBS supplemented with 2% FCS and 0.01% sodium-acid. After blocking for 10 min with 10 mg/ml human immunoglobulin, cells were sequentially incubated for 20 min on ice with primary antibodies specific for diverse cellular proteins or isotype-matched control antibodies, washed, and in case of untagged primary antibodies, further incubated with fluorescence tag-labeled secondary reagents. After final washing, cells-associated fluorescence was measured with a FACSCalibur (Becton Dickinson, San Jose, Calif.), and the recorded data were analyzed by the CellQuestPro software (Becton Dickinson).

Antibodies

Source of antibodies: Mouse mAbs anti-CD1a (HI149), CD3 (UCHT1), CD4 (RPA-T4), CD8 (HIT8α), CD11b (D12), CD14 (MφP9), CD16 (3G8), CD19 (HIB19), CD20 (2H7), CD25 (M-A251), CD40 (5C3), CD45RA (HI100), CD45RO (UCHL-1), CD50 (TU41), CD54 (HA58), CD56 (B159), CDw70 (Ki-24), CD80 (L307.4), CD83 (HB15e), CD86 (2331; FUN1), CD134 (L106), CD205 (MG38), HLA-DR (G46-6), pan-VγVδ-TCR (11F2), IL-2 (MQ1-17H12), IL-4 (8D4-8), IFNγ (B27), and IL-10 (No 20705A) from BD PharMingen, San Diego, Calif.; mouse mABs anti-CD1a (NaI/34-HLK) and CD19 (HD37) from DAKO Diagnostics, Glastrup, Sweden; mouse mAB anti-TCRVP2 (MPB2D5) from Immunotech, Marseille, France; mouse mAB anti-CD138 (B-B4) from Diaclone, Besanqon, France; mAB anti-CD102 (B-T1) from Leinco Technologies, St. Louis, Mo.; mouse mAbs anti-CD11a (TS1-22) and CD18 (TS1-18) from R. Pardi, Milano, Italy; mouse mAb anti-ICOS (F44) from R. A. Kroczek, Berlin, Germany; rat mAb anti-CCR7 (3D12) from M. Lipp, Berlin, Germany. These were used for flow cytometric analysis or cell isolation.

The following secondary Ab, conjugates and control Ab were used: RPE-conjugated goat anti-mouse IgG from Sigma-Aldrich, St. Louis, Mo.; RPE-conjugated donkey anti-rat IgG from Jackson ImmunoResearch Laboratories, West Grove, Pa.; RPE as well as RPE-Cy5 conjugated streptavidine (SA) from DAKO; APC conjugated SA from BD PharMingen; mouse control IgG1 (MOPC21) from Sigma-Aldrich; other isotype-matching control Abs from BD PharMingen. Antigens for cross-presentation included *M. tuberculosis* purified protein derivative (PPD; Statens Serum Institute, Copenhagen, Denmark), intact Influenza Matrix protein M1 (44) and M1p58-66 peptide, intact Melan-A and the Melan-A peptide with an improved HLA-A2-binding affinity p26-35 (A27L) peptide, referred to here as Melp26-35.

Magnetic MicroBeads coated with monoclonal antibodies (mAbs) anti-FITC, anti-PE, anti-biotin or anti-CD14, the mouse mAb anti CD1c (AD5-8E7), the B cell and the TCR-γ/δ isolation Kit (Miltenyi Biotec, Bergisch Gladbach, Germany) were used for magnetic cell separation. Mouse mAbs anti-CD1a (HI149), CD3 (UCHT1), CD4 (RPA-T4), CD8 (HIT8α), CD14 (MφP9), CD16 (3G8), CD19 (HIB19), CD20 (2H7), CD25 (M-A251), CD45RA (HI100), CD45RO (UCHL-1), CD56 (B159), CD64 (1.10), CD80 (L307.4), CD83 (HB15e), CD86 (2331; FUN1), CD107a (H4A3), MHC I (w6/32), HLA-DR (L243), pan-VγVδ-TCR (11F2), Vδ2-TCR (B6.1), IFNγ (B27), CCR5 (2D7) and CXCR3 (1C6) were from BD PharMingen (San Diego, Calif.); mouse mAb anti-Vγ9-PE-Cy5 (Immu360) from Beckman-Coulter (Krefeld, Germany); mouse mAbs anti-CD1a (NaI/34-HLK), CD19 (HD37) from DAKO Diagnostics (Glastrup, Sweden); mouse mAb anti-HLA-A2 allele (BB7.2) (ATCC) and CD138 (B-B4) from Diacione (Besancon, France); mouse mAb anti-VS2-TCR (BB3) from M. B. Brenner (Brigham and Women's Hospital and Harvard Medical School, Boston, Mass.); rat mAb anti-CCR7 (3D12) from M. Lipp (Max Delbrück Center for Molecular Medicine, Berlin, Germany); HLA-A*0201 tetrameric complexes containing Influenza Matrix protein M1 peptide M1p58-66 or Melan-A derived peptide Melp26-35 including either SA-PE or SA-APC (23) were used for flow cytometric analysis and cell isolation. Secondary Ab, conjugates and control Ab used were RPE-conjugated goat anti-mouse IgG from Sigma-Aldrich (St. Louis, Mo.); RPE-conjugated donkey anti-rat IgG from Jackson ImmunoResearch Laboratories (West Grove, Pa.); RPE- and RPE-Cy5 conjugated streptavidine (SA) from DAKO; APC conjugated SA from BD PharMingen; mouse control IgG1 (MOPC21) from Sigma-Aldrich.

9. Confocal Microscopy.

Immunostaining of paraformaldehyde-fixed cytospins of PBMCs, γδ T cells and monocyte-derived DCs was carried out essentially as described (Brandes et al., 2005). In brief, 1% saponin permeabilized cytospins were blocked with 3 mg/ml human Ig and casein sodium salt, and then stained with labeled anti-human HLA-ABC-Alexafluor647 (clone w6/32, mIgG2a, BioLegend, San Diego, Calif.) and primary antibodies against Vδ2-TCR (clone BB3, migG1; gift from M. Brenner, Boston) followed by treatment with fluorescently labeled goat anti-mouse IgG1-Alexafluor488 (Molecular Probes, Eugene, Oreg.), and finally mounted in Prolong Gold (Molecular Probes). For triple stainings, FITC-labeled anti-human GM130 (clone35, BD Transduction laboratories) was applied together with directly labeled anti-human Vδ2-TCR (clone B6.1, BD Pharmingen) and anti-human HLA-ABC-Alexafluor647. Stacks of confocal images (scaling resolution: 0.06 μm×0.06 μm×0.15 μm) of the samples were acquired with the laser-scanning microscope LSM 510Meta (Zeiss, Germany), processed by Huygens essential deconvolution software (Scientifique Volume Imaging, Hilversum, The Netherlands) and analysed using 3D-image restoration software package Imaris 5.5 (Bitplane, Zurich, Switzerland). For subcellular MHC I (HLA-ABC) localization and quantification in IPP-activated Vγ9Vδ2$^+$ T cells, fluorescence intensities of defined spheres (0.3 μm diameter; threshold 100 counts) within cell surface membrane, cytoplasma and nuclei (negative control) were measured in 3D-restored images. Fluorescence Intensities (relative unit [RU] of 1 equals $10^6$ counts) associated with the respective cell compartments were determined per cell by the spot function.

10. Immunotherapy of Tumors or Chronic/Recurrent Infections

For the preparation of stimulated, tumor antigen-presenting γδ T cells, 50-150 ml of peripheral blood was drawn from tumor patients (or patients with chronic/recurrent infections, see below) and γδ T cells isolation and antigen loading was performed as described above. Alternatively, such freshly isolated γδ T cells were expanded by in vitro culture under Vγ2Vδ2$^+$-TCR-stimulatory conditions (see methods of γδ T cell activation with IPP above) in the presence of 20-1000 IU/ml IL-2 and then stored in liquid nitrogen for later use in the preparation of tumor (or vaccine, see below) antigen-presenting γδ T cells. Importantly, instead of defined tumor/vaccine proteins, many other ways of antigen delivery to γδ T cells for the preparation of APCs are possible, including (among others) addition of crude (undefined) tumor cell extracts or extracts from infected cells (see below) or, alternatively, the treatment of γδ T cells by recombinant RNA/DNA technologies that are routinely used for transfection or transduction of live blood or tissue cells. Also, if defined tumor (or vaccine, see below) peptides for direct loading onto cell surface MHC molecules are known, then such peptides at 0.1-10 μg/ml are added to stimulated γδ T cells at 1-10×10$^6$ cells/ml, which are then incubated at 20-37° C. for short period of time, washed 2-times with isotonic phosphate-buffered saline solution and immediately used for therapy. It is important to emphasize that the number of γδ T cells used per administration as well as the route and frequency of γδ T cells administration depend on the efficacy in immune response induction by the individual tumor (or vaccine, see below) antigen used as well as the type and location of the tumor present in the individual patient. Protocols followed those currently employed in DC-based Immunotherapies (Fong and Engleman, 2000; Steinman et al., 2003; Schuler et al., 2003; Figdor et al., 2004), i.e. 1-20×10⁶ cells/0.5-2 ml per administration with 1 to 6 follow-up administrations with the same or lower amounts of cells at two-weeks to two-months intervals.

Example 1

Human γδ T-APCs Efficiently Cross-Present Soluble Proteins to CD8⁺ αβ T Cells

Figure 18:
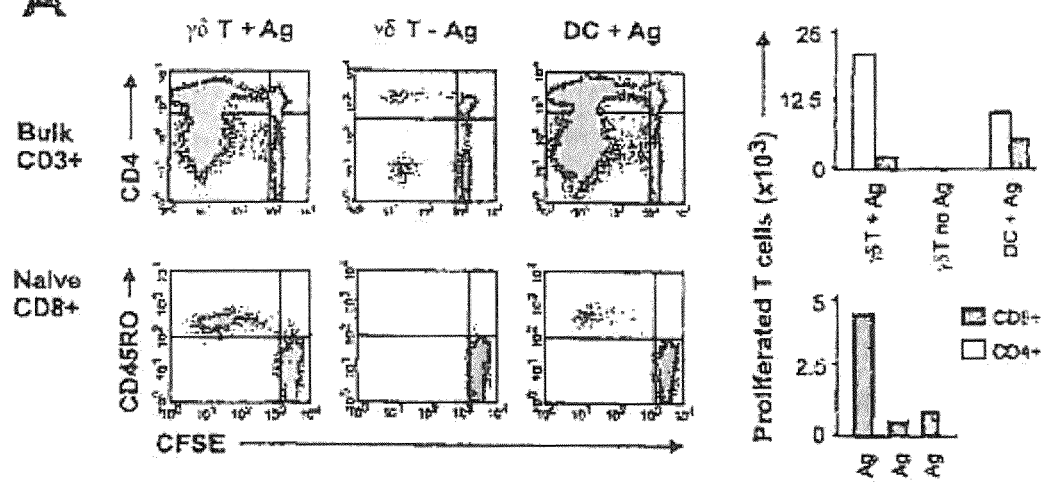
FIG. 18. γδ T-APCs cross-present soluble protein antigen to CD8+ αβ T cells. (A) γδ T-APCs and DCs were treated with PPD, then washed and co-cultured for 10 d with CFSE-labeled bulk αβ T cells or purified naïve CD8+ αβ T cells at a APC/responder cell ratio of 1:10. Bar diagrams show the absolute number of proliferated (CFSE-low) cells. Data are representative of 2 and 3 experiments with bulk and naïve CD8+ αβ T cells, respectively. (B) γδ T-APCs and DCs cross-present influenza matrix protein M1 to the HLA-A2-restricted, M1p58-66-specific CD8+ αβ T cell clone FLUMA55 (APC/responder cell ratio of 1:20). Negative control, 4 µM M1 treated feeder B cell control. The right panel compiles data from 7 independent FLUMA55 cross-priming experiments with γδ T-APCs and DCs treated with 0.4 µM M1; additional control, 0.1 µM M1p58-66 pulsed DCs. Boxes' lower/upper ends and middle lines depict 25/75 percentile and median. (C) Bulk CD8+ αβ T cells were stimulated with M1 treated γδ T-APCs and S/LPS-DCs (APC/responder cell ratio of 1:20) and after 10 d of culture M1p58-66-specific responder cells were quantified by M1p58-66-tetramer staining. Positive control, M1p58-66 pulsed γδ T-APCs and DCs; representative of 2 independent experiments. (D) γδ T-APCs and DCs, either treated with shear force and LPS or with CD40L, differ in their efficiency to cross-present M1 to bulk CD8+ αβ T cells. Data points are obtained with blood cells from 2-4 different donors. One-tailed students t-test; NS, not significant (data points obtained with cells from the same 2 donors).
Figure 18:
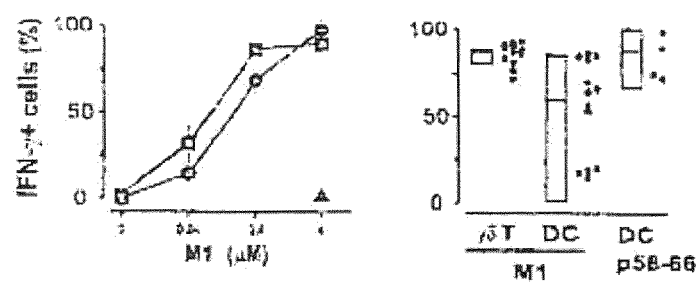
Figure 18:
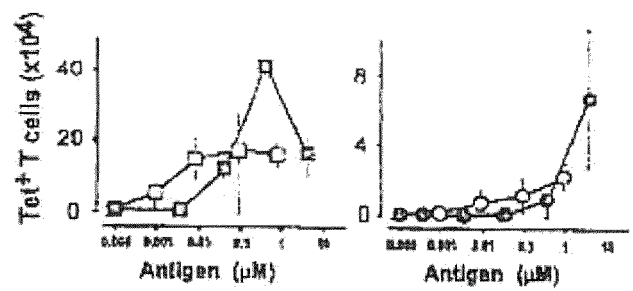
Figure 18:
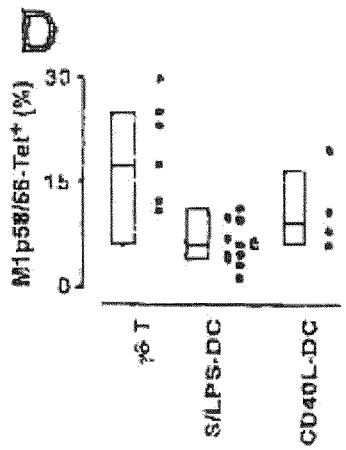

First, we examined the ability of γδ T-APCs to induce αβ T cell proliferation in response to the highly complex protein mixture M. tuberculosis purified protein derivative (PPD). γδ T-APCs or monocyte-derived DCs were loaded with PPD, washed and then co-cultured with autologous, 5-(and 6-) carboxyfluorescein diacetate succinimidyl ester (CFSE)-labeled responder cells. Using bulk CD3⁺ T cells as responder cells, both CD8⁺ T cells and CD4⁺ T cells showed strong proliferation responses, as assessed by reduction in CFSE signals (FIG. 18 A). Similar antigen-dependent responses were obtained with purified naïve CD8⁺ αβ T cells as responder cells. We concluded that γδ T-APCs compared well with DCs in the induction of CD8⁺ αβ T cell responses to complex mycobacteria-derived protein antigens.

To confirm these initial findings in support for cross-presentation by γδ T-APCs, we turned to an experimental model that allowed more detailed investigations. This model included the well defined influenza virus-encoded matrix protein M1 that induces strong CD8⁺ αβ T cell responses to M1p58-66, the immunodominant peptide contained within M1, in human leukocyte antigen A*0201 (HLA-A2)-positive individuals (Pittet et al., 1999). First, cross-presentation was studied in a HLA-A2-restricted CD8⁺ αβ T cell clone, which produces IFN-γ in response to M1p58-66-presenting, HLA-A2⁺ APCs. M1 pre-treated γδ T-APCs induced robust and highly reproducible effector cell activation, and responses were already detected when 0.04 μM of M1 were used during APC preparation (FIG. 18 B). These findings did not result from M1p58-66 peptide contamination in the M1 protein preparation (FIG. 24), demonstrating that γδ T-APCs were able to take up and process exogenous M1 for presentation in the context of MHC I molecules. B cells used as feeder cells during in vitro activation of Vγ9Vδ2⁺ T cells failed to cross-present M1. Of note, γδ T-APCs from different donors gave reproducible results, which is in contrast to the strikingly variable responses obtained with DCs (FIG. 18 B). Pulsing of mature DCs with M1p58-66 produced highly potent APCs, suggesting a rate limiting factor affecting either antigen uptake or intracellular processing in DCs. In the next step we tested M1p58-66-pulsed γδ T-APCs for their ability to induce proliferation in blood CD8⁺ αβ T cells. M1p58-66-specific cells (0.01-0.5%), assessed by M1p58-66-tetramer staining, are primarily found in the memory T cell compartment of healthy HLA-A2⁺ individuals (Pittet et al., 1999). Responses obtained with M1p58-66-pulsed γδ T-APCs were unmatched in terms of potency and efficacy, as compared to DCs, monocytes and controls for feeder B cells (FIG. 25).

Moreover, γδ T-APCs were also very adept in cross-presentation of M1, involving the uptake and intracellular processing of exogenous protein, to this polyclonal M1p58-66-reactive CD8⁺ αβ T cell compartment (FIG. 18 C). Striking variation in responses to DCs prompted us to evaluate different strategies for DC generation, including substituting IL-15 for IL4 during monocyte differentiation (Dubsky et al., 2007), and applying shear force in combination with LPS or CD40-signaling (Larsson et al., 2001; Delamarre et al., 2005) to induce DC maturation. None of these treatments led to substantial improvements (FIG. 18 D), and in all subsequent experiments shear force/LPS-treated DCs were used as before.

Example 2

Antigen Cross-Presentation by γδ T-APCs Involves Proteasome Activity and de Novo Synthesized MHC I Molecules The efficiency of antigen presentation to CD8⁺ αβ T cells correlates with the rate of de novo synthesis of MHC I and transport of peptide-MHC I complexes from the MHC I peptide loading compartment (endoplasmic reticulum) to the cell surface (Cox et al., 1990). The classical MHC I pathway of peptide presentation involves antigen degradation by the proteasome in the cytoplasm, followed by the transporter associated with antigen processing (TAP)-dependent transport of proteolytic products across the endoplasmic reticulum membrane and loading of peptides onto MHC I molecules (Yewdell et al., 2005; Cresswell et al., 2005; Rock et al., 2005; Villadangos et al., 2007). Alternative, TAP- and proteasome-independent pathways have been proposed, including lysosomal (as opposed to cytoplasmic) degradation of internalized antigen followed by peptide loading onto recycling or cell surface MHC I.

Figure 19:
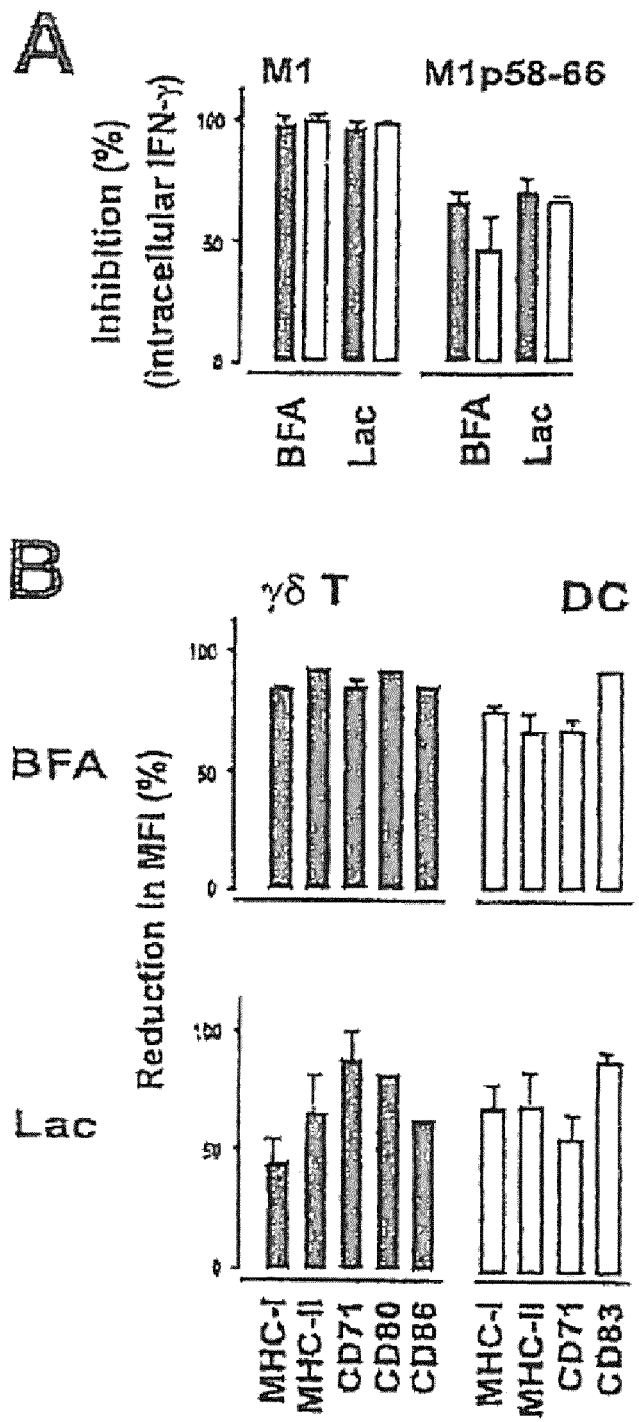
FIG. 19. Antigen cross-presentation by γδ T-APCs depends on de novo MHC I synthesis and proteasome activity. (A) Blockade of protein export and proteasome activity abrogates antigen cross-presentation. Brefeldin A (BFA)- or lactacystin (Lac)-treated γδ T cells (solid bars) and DCs (open bars) were stimulated/matured in the presence of M1 (0.4 µM) or pulsed with M1p58-66 (0.1 µM) and then tested in the FLUMA55 IFN-γ production assay (FIG. 1B). Inhibition (%) corresponds to the reduction in mean fluorescence intensity (MFI) of intracellular IFN-γ stainings in responder cells cultured with inhibitor-pretreated APCs as compared to untreated APCS. (B) Blockade of proteasome activity and protein export greatly diminishes phenotypic γδ T-APC generation and DC maturation. Data in (A) and (B) are representative of 3 experiments with blood from 2 different donors.

The route(s) of antigen processing leading to peptide loading onto MHC I within γδ T-APCs are not known. The two inhibitors lactacystin (Craiu et al., 1997) and brefeldin A (Doms et al., 2003) selectively target the proteasome and the trans-Golgi network, respectively, and thus interfere with the classical (proteasome- and protein export-dependent) MHC I pathway. We found that cross-presentation in γδ T-APCs and DCs was fully inhibited by these compounds, supporting the notion that γδ T-APCs do not differ from DCs in their use of the classical MHC I pathway for processing of exogenous influenza matrix protein M1 (FIG. 19 A). Responses to M1p58-66 pulsed APCs were only partially affected, which agrees with free, albeit reduced access of short peptides to cell surface MHC I molecules (see below). Lysosomal proteases seem to be of minor importance since chloroquin only partially (≦50%) inhibited M1 cross-presentation in γδ T-APCs and DCs, which is in clear contrast to the MHC II pathway in these APCs (Brandes et al., 2005). Peptide loading onto nascent MHC I within the endoplasmic reticulum and protein export are a prerequisite for cell surface expression of newly synthesized MHC I. Therefore, brefeldin A as well as lactacystin were expected to reduce the numbers of cell surface MHC I (FIG. 19 B), which explains their inhibitory effect on M1p58-66 pulsing (reduced numbers of cell surface MHC I for peptide loading; see FIG. 19 A). TCR-triggering in Vγ9Vδ2⁺ T cells also led to the expression of other cell surface APC markers, as previously shown for peptide presentation (MHC II), cell activation (CD71) and co-stimulatory (CD80, CD86) molecules (Brandes et al., 2005), which was inhibited by brefeldin A and lactacystin (FIG. 19 B). In addition to antigen-processing, the proteasome exerts control over signaling cascades (e.g. NF-κB activation) and linked gene expression (Yewdell, 2005). This may explain in part the observed reduction in the expression level of APC markers (including MHC I) when γδ T cell activation was carried out in the presence of the proteasome inhibitor (FIG. 19 B). Collectively, we demonstrated that the proteasome and de novo MHC I synthesis are involved in antigen cross-presentation of M1 protein in γδ T-APCs.

Figure 20:
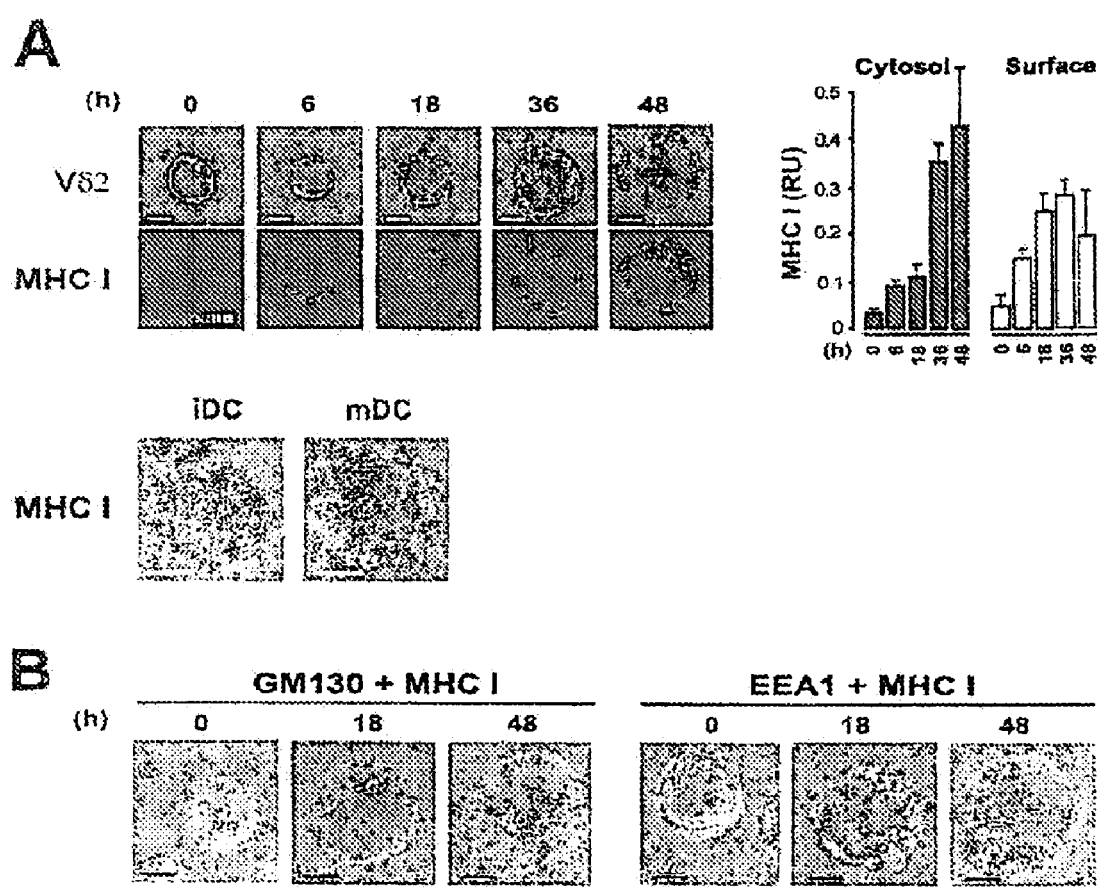
FIG. 20. Cellular distribution of MHC I during activation of Vγ9Vδ2+ T cells. (A) Activation of Vγ9Vδ2+ T cells with IPP for 648 h in the presence of feeder B cells followed by confocal immunofluorescence microscopic analysis of Vδ2-TCR staining (green) in combination with digital interference contrast images (upper row), or with MHC I staining (fire scale color mapping) (lower row); (0 h), resting γδ T cells. As control, digital interference contrast images in combination with MHC I (red) and nuclei (blue) stainings are shown for immature (iDC) and mature DCs (mDC). Bar graph represents quantifications of intracellular (cytosol) and cell membrane (surface) associated MHC I within individual γδ T cells at the indicated IPP stimulation time points; relative unit (RU) of 1 equals $10^6$ counts with 3-6 cells analyzed per data point. (B) Increased cell surface MHC I staining involves de novo MHC I synthesis. Expression of MHC I (red) in conjunction with GM130 (green) is shown as maximum intensity projections in combination with digital interference contrast images (50:50 fluorescence intensity ratio in yellow). Bars in (A) and (B) represent 5 µm (10 µm for DCs).

Since de novo MHC I synthesis is of primary importance for induction of CD8⁺ αβ T cell responses (Cox et al., 1990), we performed immunocytochemical analysis of resting and activated Vg9Vδ2⁺ T cells. TCR-triggered upregulation of MHC I was substantial, paralleled blast formation and was composed of increased cytosolic and cell surface MHC I staining (FIG. 20 A). Peak levels in total MHC I staining were >7-fold above levels in unstimulated γδ T cells and were reached between 18 h and 48 h of culture. As expected (Delamarre et al., 2003), shear force and LPS treatment in DCs resulted also in increased cell surface MHC I expression. Elevated cell surface staining was due to de novo MHC I synthesis as evidenced by lack of intracellular MHC I storage compartments in resting γδ T cells and by sustained co-localization of MHC I with the trans-Golgi network (GM130) during the course of stimulation (FIG. 19 B and FIG. 26).

Example 3

Figure 21:
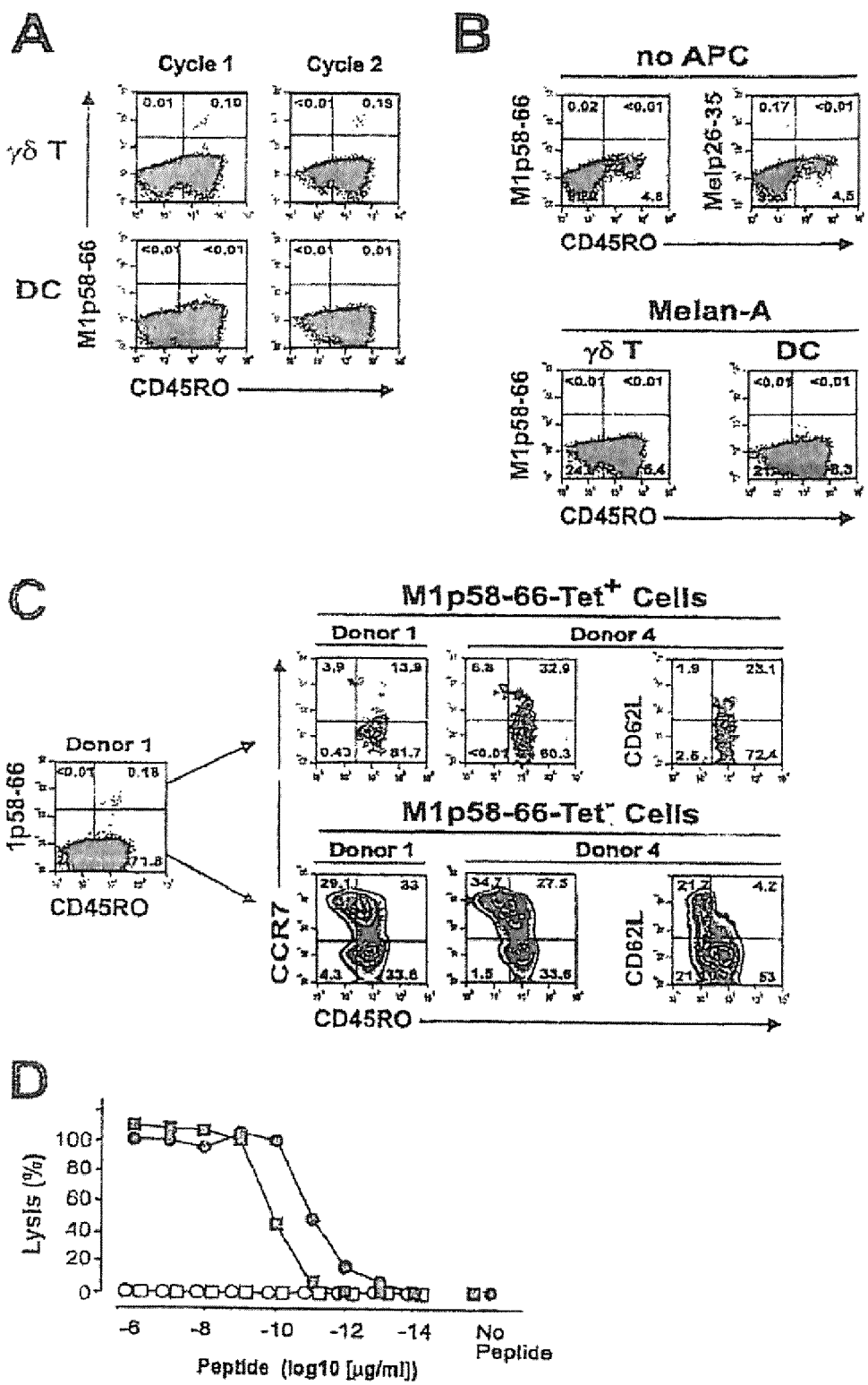
FIG. 21. γδ T-APCs and DCs fail to cross-present Melan-A to Melp26-35-specific CD8+ αβ T cells. (A) Melan-A-treated γδ T-APCs are unable to induce intracellular IFN-γ production in the Melp26-35-specific, HLA-A2-restricted CD8+ αβ T cell clone LAU 337. γδ T-APCs were treated with or without Melan-A and then co-cultured with the Melp26-35-specific responder cells for determination of intracellular IFN-γ production. Controls include Melp26-35-pulsed γδ T-APCs together with LAU 337 responder cells, and M1 cross-presenting γδ T-APCs together with FLUMA55 responder cells. Numbers in brackets represent the mean. (B) Melan-A cross-presenting APCs failed to induce expansion of Melp26-35-specific responder cells in blood CD8+ αβ T cells. γδ T-APCs and DCs were incubated with Melan-A at indicated concentrations and co-cultured with CFSE-labeled, blood CD8+ αβ T cells at a APC/responder cell ratio of 1:10. Alternatively, Melp26-35 pulsed γδ T-APCs or M1 cross-presenting γδ T-APCs were used and the numbers (% of total) of Melp26-

The Immunoproteasome in γδ T-APCs Prevents Induction of Melp26-35-specific CD8$^+$ αβ T Cell Responses To test a potential function in anti-tumor immunity, we next studied the ability of γδ T-APCs to cross-present the melanocyte/melanoma-differentiation antigen Melan-A (MART-1), which contains the immunodominant peptide Melp26-35 recognized by HLA-A2-restricted CD8$^+$ αβ T cells (Romero et al., 2002). Melp26-35 specific CD8$^+$ αβ T cells are readily detected in both melanoma patients and healthy individuals (Pittet et al., 1999), thus allowing us to study Melan-A cross-presentation by γδ T-APCs with blood cells from healthy volunteers. Of note, Melan-A-pretreated γδ T-APCs and DCs both failed to induce IFN-γ production in HLA-A2-restricted, Melp26-35-specific responder cell clones (FIG. 21 A, additional data not shown). This failure was not due to problems with antigen presentation per se or due to a weak responsiveness by the responder clone since Melp26-35-pulsed γδ T-APCs and DCs induced strong IFN-γ responses. Moreover, uptake of soluble proteins was not affected neither since the same γδ T-APC preparations were perfectly capable of cross-presenting M1 to the M1p58-66-specific responder cell clone (FIGS. 18 B and 21 A). These findings were mirrored in a responder cell proliferation assay, showing that Melan-A pretreated γδ T-APCs or DCs failed to induce the expansion of Melp26-35-tetramer$^+$ cells present within bulk CD8$^+$ αβ T cells (FIG. 21 B). Again, control APCs, including Melp2635-pulsed γδ T-APCs and M1 cross-presenting γδ T-APCs, performed well. These findings illustrate that lack of Melan-A cross-presentation was neither due to problems with antigen uptake or processing per se nor peptide presentation.

The proteasome exerts a crucial role in the classical MHC I pathway of peptide presentation and exists in two forms, the standard proteasome present in all nucleated cells and the immunoproteasome, which contains alternative, IFN-γ- or TNF-α-inducible protease subunits (Strehl et al., 2005). The immunoproteasome produces a different spectrum of peptides and thereby influences the shape of CD8$^+$ αβ T cell responses under inflammatory conditions. For instance, it has been shown that immunodominant peptide Melp26-35 is readily produced by the standard proteasome whereas it is rapidly degraded by the immunoproteasome (Chapatte et al., 2006; Morel et al., 2000). We found that peripheral blood γδ T cells and in vitro generated γδ T-APCs contained predominantly the immunoproteasome (FIG. 22 A), as assessed by immunostaining of the immunoproteasome subunit β1i/LMP2 on Western blot (Valmori et al., 1999). By contrast, immature DCs and B cells had much lower amounts of the immunoproteasome. Staining of the standard proteasome subunit α5 was performed to monitor the total amount of proteasome in relation to the immunoproteasome (β1i/LMP2). Purified proteasome from HEK293 cells, which do not contain the immunoproteasome (β1i/LMP2-negative), was included as a negative control. The immunoproteasome in γδ T-APCs was functional as demonstrated by peptide product analysis after digestion of the peptide substrate Melan-A$_{15-40}$ with freshly prepared, purified proteasome (FIG. 22 B). Absence of the signature peptide fragment Melan-A$_{15-35}$ indicates the functional dominance of the immunoproteasome and, vice versa, its presence correlates with the activity of the standard proteasome. Maximal standard protease activity was obtained with the HEK293-derived proteasome preparation. Of note, despite the fact that proteasome purified from immature DCs produces detectable amount of Melan-A$_{15-35}$ fragment (FIG. 22 B), Melan-A cross-presenting DCs still failed to induce substantial and reproducible proliferation in Melp26-35-specific responder cells (FIG. 21 B). These negative results may be explained in part by the overall inefficiency of DCs in cross-presentation of soluble proteins (FIG. 18). Collectively, the predominant immunoproteasome in γδ T-APCs fully agrees with the complete absence of Melp26-35-specific CD8$^+$ αβ T cell responses in our Melan-A cross-presentation assays.

Example 4

γδ T-APCs Induce Effector Cell Differentiation in naïve CD8$^+$ αβ T Cells

To examine if γδ T-APCs have professional cross-presentation capabilities, M1 cross-presenting γδ T-APCs or DCs were cultured with a 20-fold excess of sorted autologous naïve CD8$^+$ αβ T cells. M1p58-66-specific responder cells were quantified after 10 d of culture (cycle 1) or after a second round of stimulation (cycle 2). After cycle 1 a significant portion of CD8$^+$ αβ T cells expressed the memory marker CD45RO (FIG. 23 A). M1p58-66-specific T cells became detectable (0.1-0.3% among total CD8$^+$ αβ T cells), as assessed by tetramer staining, and this T cell subset was maintained during secondary expansion, permitting their further examination (see below). This is remarkable, because the frequency of M1p58-66-specific (M1p58-66-tetramer$^+$) cells in the starting population of naïve blood CD8$^+$ T cells was below the level of detection (<1/50,000) (Lehner et al., 1995). In contrast to γδ T-APCs, the responses of naïve CD8$^+$ αβ T cells to M1 cross-presenting DCs were highly variable or undetectable (example in FIG. 23 A). The exquisite specificity of the M1p58-66 response is supported by the lack of tetramer staining in cultures without APCs or in cultures with γδ T-APCs and DCs cross-presenting the irrelevant antigen Melan-A (FIG. 23 B). The majority of newly generated M1p58-66-tetramer$^+$ T cells lost lymph node homing properties, as evidenced by reduced levels of the chemokine receptor CCR7 and L-selectin (CD62L) (FIG. 27), which is characteristic of effector/memory T cells (Sallusto et al., 1999). By contrast, M1-unrelated memory T cells contained a mixture of effector/memory (CCR7$^-$) T cells and central memory (CCR7$^+$) T cells, while naïve (CD45RO$^-$) T cells in these cultures largely retained both CCR7 and L-selectin.

After the second cycle, 21% of sorted M1p58-66-tetramer$^+$ T cells carried Vβ17-TCRs, and this fraction became enriched (>70%) during further in vitro expansion, in agreement with the reported TCR preference of M1p58436-specific memory T cells in human peripheral blood (Lehner et al., 1995). This finding minimizes the likelihood of a substantial memory cell contamination in our sorted naïve CD8$^+$ αβ T cell preparations. For further analysis, M1p58-66-tetramer$^+$ sorted cells were cloned by limited dilution. Twenty-six T cell clones were M1p58-66-tetramer$^+$, and all of these specifically lysed M1p58-66 pulsed target cells with half maximal effective M1p58-66 concentrations ranging between 10$^{-9}$ and $10^{-11}$ µg peptide/ml (FIG. 23 C). In support of specificity, target cells either unpulsed or pulsed with the unrelated Melan-A peptide Melp26-35 were not recognized (FIG. 23 C). In experiments where M1 cross-presenting DCs induced expansion of M1p58-66-tetramer$^+$ CD8$^+$ αβ T cells, the fraction of Vβ17$^+$ cells also increased during bulk culture (from 21% to 83%) and clones of M1p58-66-tetramer$^+$ cells lysed target cells with similar specificity and efficiency as seen with γδ T-APC-induced clones (FIG. 23 C). These data demonstrated that cross-presenting γδ T-APCs were capable of triggering proliferation and differentiation in naïve, peptide-specific CD8$^+$ responder cells.

The important role for γδ T cells in anti-microbial and anti-tumor immunity is undisputed (Hayday et al., 2000; Holtmeier et al., 2005; Kronenberg et al., 2007). Yet, unlike αβ T cells, many aspects in γδ T cell activation and effector function generation are ill-defined. Vγ9Vδ2$^+$ T cells, which predominate in human peripheral blood, are exquisitely selective for a small selection of structurally related compounds, as illustrated by their vast expansion in response to such compounds during culture of peripheral blood mononuclear cells. The physiologic correlate to this in vitro finding is seen in patients infected with microbes that are known to produce HMB-PP, the most potent compound (Eberl et al., 2003). It is not clear how Vγ9Vδ2$^+$ T cells recognize these non-peptide agonists and whether TCR triggering requires the presentation of such compounds by specialized "feeder cells". It is certain, however, that classical antigen processing and peptide presentation pathways provided by professional APCs are not involved, ruling out an obligatory association with lymph nodes where instruction of αβ T cells occurs (Banchereau et al., 1998). It is equally unclear-why Vγ9VS2$^+$ T cells predominate in peripheral blood and why they are largely excluded from healthy peripheral tissues that harbor other types of γδ T cells (Hayday et al., 2000; Holtmeier et al., 2005; Kronenberg et al., 2007; Eberl et al., 2006). Furthermore, it is not known when this unique memory Vγ9Vδ2$^+$ T cell compartment is established (exposure of naïve γδ T cells to HMB-PP-producing microbes during early childhood being a possible explanation). Activation of human Vγ9Vδ2$^+$ T cells with HMB-PP and related compounds leads to highly diverse effector functions, including cytokine and chemokine production, provision of B cell help and target cell lysis (Hayday et al., 2000; Holtmeier et al., 2005; Kronenberg et al., 2007). Importantly, fully activated Vγ9VS2$^+$ T cells (termed γδ T-APCs) express CCR7 that enables lymph node homing together with a plethora of antigen-presentation and co-stimulation molecules (Brandes et al., 2003; Brandes et al., 2005).

Reactivity to microbes (and tumors), responsiveness to inflammatory chemokines and localization in peripheral blood underscores the rapid participation of Vγ9Vδ2$^+$ T cells in host defense (Hayday et al., 2000; Holtmeier et al., 2005; Kronenberg et al., 2007; Moser et al., 2007). This view is supported by the present study demonstrating that γδ T-APCs are highly efficient antigen cross-presenting cells. We have shown that γδ T-APCs are capable of processing exogenous soluble proteins and presenting peptide-MHC I complexes to antigen-specific CD8$^+$ αβ T cells. γδ T-APCs did not only activate memory CD8$^+$ αβ T cells but also induced robust naïve CD8$^+$ αβ T cell proliferation and effector cell generation, a process which is known to depend on professional APCs (Banchereau et al., 2005). Surprisingly, γδ T-APCs were much more reliable than monocyte-derived DCs in terms of effectiveness and reproducibility. It is possible that monocyte-derived DCs do not represent the bona fide cross-presenting DCs in human (den Hauer et al., 2000; Stoitzner et al., 2006; Dudziak et al., 2007). Modulation of our DC preparation protocol, for instance by substituting IL-15 for IL-4 during monocyte differentiation (Dubsky et al., 2007) or by including alternative DC maturation stimuli (Larsson et al., 2001; Delamarre et al., 2005), did not improve their performance. Also, we noticed substantial functional variation in individual DC preparations derived from monocytes of the same blood donor, pointing toward some undefined difficulties in the in vitro generation of cross-presenting DCs. Such difficulties were not encountered in previous CD4$^+$ αβ T cell activation studies (Brandes et al., 2005). The observed superior antigen cross-presentation activity in γδ T-APCs may also be due to highly efficient antigen processing and peptide-MHC I presentation mechanisms. Indeed, treatment with IPP led to impressive de novo synthesis of MHC I, which is a prerequisite for optimal operation of the classical MHC I pathway (Cox et al., 1990). The predominant immunoproteasome in γδ T-APCs is another feature that promotes efficient antigen cross-presentation (Strehlet et al., 2005; Deol et al., 2007). Monocyte-derived DCs also contain the immunoproteasome, albeit at much lower level than the standard proteasome. Future studies will tell which stages in antigen cross-presentation (uptake of soluble protein, access to the cytoplasm, protein degradation, peptide loading onto MHC I, peptide-MHC I cell surface presentation) are accountable for the extraordinary antigen cross-presentation in γδ T-APCs.

Our findings support a model whereby γδ T-APCs are induced from peripheral blood Vγ9Vδ2$^+$ T cells following their recruitment to the site of infection in response to local inflammatory chemokines (Brandes et al., 2003; Cipriani et al., 2000) and their exposure to microbe-derived agonists (Morita et al., 2007; Brandes et al., 2005; Moser et al., 2007). Positioning in peripheral blood and immediate responsiveness to inflammatory cues ensure their rapid involvement in host defense, well before microbe-specific αβ T cells become engaged. γδ T-APCs not only mobilize proinflammatory (IFN-γ, TNF-α, chemokines) and cytotoxic activities (Hayday et al., 2000; Holtmeier et al., 2005; Kronenberg et al., 2007) but also process microbial antigen for induction of CD8$^+$ αβ T cell responses, as suggested by the present data. These APC functions are facilitated by lysis of microbe-infected tissue cells, generating substrates for endocytosis, and by the immunoproteasome, which efficiently processes the microbial material into immunogenic peptides. Equally important, newly generated γδ T-APCs feature lymph node homing and CD8$^+$ αβ T cells attracting properties (Brandes et al., 2003; Cipriani et al., 2000), a prerequisite for productive antigen-presentation to rare naïve, microbe-specific CD8$^+$ T cells present in draining lymph nodes (Castellino et al., 2006). Collectively, these features support the view that γδ T-APCs are important players in the fast generation of microbe-specific, cytotoxic effector T cells at initial stages of infections. Since Vγ9Vδ2$^+$ T cells also respond to tumor antigens, γδ T-APCs may play a similar role in tumor-specific CD8$^+$ αβ T cell responses.

REFERENCES

Alcami, A. 2003. Viral mimicry of cytokines, chemokines and their receptors. Nat. Rev. Immunol. 3: 36-50.

Banchereau, J., Pascual, V., and Palucka, A. K. (2004). Autoimmunity through cytokine-induced dendritic cell activation. Immunity. 20, 539-550.

Banchereau, J. and Steinman, R. M. (1998). Dendritic cells and the control of immunity. Nature 392, 245-252.

Brandes, M., Willimann, K., Lang, A. B., Nam, K. H., Jin, C., Brenner, M. B., Morita, C. T., and Moser, B. (2003). Flexible migration program regulates gamma delta T-cell involvement in humoral immunity. Blood 102, 3693-3701.

Brandes, M., K. Willimann, and B. Moser. 2005. Professional antigen-presentation function by human gammadelta T Cells. Science 309:264-268.

Carding, S. R. and Egan, P. J. (2002). Gammadelta T cells: functional plasticity and heterogeneity. Nat. Rev. Immunol. 2, 336-345.

Castellino, F., A. Y. Huang, G. Altan-Bonnet, S. Stoll, C. Scheinecker, and R. N. Germain. 2006. Chemokines enhance immunity by guiding naive CD8+ T cells to sites of CD4+ T cell-dendritic cell interaction. Nature 440:890-895.

Chapatte, L., M. Ayyoub, S. Morel, A. L. Peitrequin, N. Levy, C. Servis, B. J. Van den Eynde, D. Valmori, and F. Levy. 2006. Processing of tumor-associated antigen by the proteasomes of dendritic cells controls in vivo T-cell responses. Cancer Res. 66:5461-5468.

Chen, Z. W. and Letvin, N. L. (2003). Adaptive immune response of Vgamma2Vdelta2 T cells: a new paradigm. Trends Immunol. 24, 213-219.

Cipriani, B., G. Borsellino, F. Poccia, R. Placido, D. Tramonti, S. Bach, L. Battistini, and C. F. Brosnan. 2000. Activation of C—C β-chemokines in human peripheral blood gammaδ T cells by isopentenyl pyrophosphate and regulation by cytokines. Blood 95:39-47.

Cox, J. H., J. W. Yewdell, L. C. Eisenlohr, P. R. Johnson, and J. R. Bennink. 1990. Antigen presentation requires transport of MHC class I molecules from the endoplasmic reticulum. Science 247:715-718.

Craiu, A., M. Gaczynska, T. Akopian, C. F. Gramm, G. Fenteany, A. L. Goldberg, and K. L. Rock. 1997. Lactacystin and clasto-lactacystin beta-lactone modify multiple proteasome beta-subunits and inhibit intracellular protein degradation and major histocompatibility complex class I antigen presentation. J. Biol. Chem. 272:13437-13445.

Cresswell, P., A. L. Ackerman, A. Giodini, D. R. Peaper, and P. A. Wearsch. 2005. Mechanisms of MHC class I-restricted antigen processing and cross-presentation. Immunol. Rev. 207: 145-157.

Delamarre, L., H. Holcombe, and I. Mellman. 2003. Presentation of exogenous antigens on major histocompatibility complex (MHC) class I and MHC class II molecules is differentially regulated during dendritic cell maturation. J. Exp. Med. 198:111-122.

Delamarre, L., M. Pack, H. Chang, I. Mellman, and E. S. Trombetta. 2005. Differential lysosomal proteolysis in antigen-presenting cells determines antigen fate. Science 307:1630-1634.

den Haan, J. M., S. M. Lehar, and M. J. Bevan. 2000. CD8(+) but not CD8(−) dendritic cells cross-prime cytotoxic T cells in vivo. J. Exp. Med. 192:1685-1696.

Deol, P., D. M. Zaiss, J. J. Monaco, and A. J. Sijts. 2007. Rates of processing determine the immunogenicity of immunoproteasome-generated epitopes. J. Immunol. 178: 7557-7562.

Doherty, P. C. and J. P. Christensen. 2000. Accessing complexity: the dynamics of virus-specific T cell responses. Annu. Rev. Immunol. 18: 561-592.

Doms, R. W., G. Russ, and J. W. Yewdell. 1989. Brefeldin A redistributes resident and itinerant Golgi proteins to the endoplasmic reticulum. J. Cell Biol. 109:61-72.

Dubsky, P., H. Saito, M. Leogier, C. Dantin, J. E. Connolly, J. Banchereau, and A. K. Palucka. 2007. IL-15-induced human DC efficiently prime melanoma-specific naïve CD8+ T cells to differentiate into CTL. Eur. J. Immunol. 37: 1678-1690.

Dudziak, D., A. O. Kamphorst, G. F. Heidkamp, V. R. Buchholz, C. Trumpfheller, S. Yamazaki, C. Cheong, K. Liu, H. W. Lee, C. G. Park, R. M. Steinman, and M. C. Nussenzweig. 2007. Differential antigen processing by dendritic cell subsets in vivo. Science 315:107-111.

Eberl, L. M., S. Meuter, and B. Moser. 2006. Homing and function of human skin gammadelta T cells and NK cells: relevance for tumor surveillance. J. Immunol. 176:4331-4336.

Eberl, M., Hintz, M., Reichenberg, A., Kollas, A. K., Wiesner, J., and Jomaa, H. (2003). Microbial isoprenoid biosynthesis and human gammadelta T cell activation. FEBS Lett. 544, 4-10.

Figdor, C. G., de Vries, I. J., Lesterhuis, W. J., and Melief, C. J. (2004). Dendritic cell immunotherapy: mapping the way. Nat. Med. 10, 475-480.

Fong, L. and Engleman, E. G. (2000). Dendritic cells in cancer immunotherapy. Annu. Rev. Immunol. 18, 245-273.

Hayday, A. C. 2000. [gamma][delta] cells: a right time and a right place for a conserved third way of protection. Annu. Rev. Immunol. 18:975-1026.

Holtmeier, W. and D. Kabelitz. 2005. gammadelta T cells link innate and adaptive immune responses. Chem. Immunol. Allergy 86:151-183.

Kronenberg, M. and W. L. Havran. 2007. Frontline T cells: gammadelta T cells and intraepithelial lymphocytes. Immunol. Rev. 215:5-7.

Lane, P., C. Burdet, F. McConnell, A. Lanzavecchia, and E. Padovan. 1995. CD40 ligand-independent B cell activation revealed by CD40 ligand-deficient T cell clones: evidence for distinct activation requirements for antibody formation and B cell proliferation. Eur. J. Immunol. 25: 1788-1793.

Langenkamp, A., Messi, M., Lanzavecchia, A., and Sallusto, F. (2000). Kinetics of dendritic cell activation: impact on priming of TH1, TH2 and nonpolarized T cells. Nat. Immunol. 1, 311-316.

Larsson, M., J. F. Fonteneau, S. Somersan, C. Sanders, K. Bickham, E. K. Thomas, K. Mahnke, and N. Bhardwaj. 2001. Efficiency of cross presentation of vaccinia virus-derived antigens by human dendritic cells. Eur. J. Immunol. 31:3432-3442.

Lehner, P. J., E. C. Wang, P. A. Moss, S. Williams, K. Plaft, S. M. Friedman, J. I. Bell, and L. K. Borysiewicz. 1995. Human HLA-A0201-restricted cytotoxic T lymphocyte recognition of influenza A is dominated by T cells bearing the V beta 17 gene segment. J. Exp. Med. 181:79-91.

Miller, M. J., Hejazi, A. S., Wei, S. H., Cahalan, M. D., and Parker, I. (2004). T cell repertoire scanning is promoted by dynamic dendritic cell behavior and random T cell motility in the lymph node. Proc. Natl. Acad. Sci. U.S. A 101, 998-1003.

Mohamadzadeh, M., F. Berard, G. Essert, C. Chalouni, B. Pulendran, J. Davoust, G. Bridges, A. K. Palucka, and J. Bancbereau. 2001. Interleukin 15 skews monocyte differentiation into dendritic cells with features of Langerhans cells. J. Exp. Med. 194:1013-1020.

Morel, S., F. Levy, O. Burlet-Schiltz, F. Brasseur, M. Probst-Kepper, A. L. Peitrequin, B. Monsarrat, R. Van Velthoven, J. C. Cerottini, T. Boon, J. E. Gairin, and B. J. Van den Eynde. 2000. Processing of some antigens by the standard proteasome but not by the immunoproteasome results in poor presentation by dendritic cells. Immunity. 12:107-117.

Morita, C. T., Mariuzza, R. A., and Brenner, M. B. (2000). Antigen recognition by human gamma delta T cells: pattern recognition by the adaptive immune system. Springer Semin. Immunopathol. 22, 191-217.

Morita, C. T., C. Jin, G. Sarikonda, and H. Wang. 2007. Nonpeptide antigens, presentation mechanisms, and immunological memory of human Vgamma2Vdelta2 T cells: discriminating friend from foe through the recognition of prenyl pyrophosphate antigens. *Immunol. Rev.* 215: 59-76.

Moser, B. and M. Eberl. 2007. gammadelta T cells: novel initiators of adaptive immunity. Immunol. Rev. 215:89-102.

Moser, B., Wolf, M., Walz, A., and Loetscher, P. (2004). Chemokines: multiple levels of leukocyte migration control. Trends Immunol. 25, 75-84.

Pittet, M. J., D. Valmori, P. R. Dunbar, D. E. Speiser, D. Lienard, F. Lejeune, K. Fleischhauer, V. Cerundolo, J. C. Cerottini, and P. Romero. 1999. High frequencies of naïve Melan-A/MART-1-specific CD8(+) T cells in a large proportion of human histocompatibility leukocyte antigen (HLA)-A2 individuals. *J. Exp. Med.* 190:705-715.

Rock, K. L. and L. Shen. 2005. Cross-presentation: underlying mechanisms and role in immune surveillance. *Immunol. Rev.* 207:166-183.

Romero, P., D. Valmori, M. J. Pittet, A. Zippelius, D. Rimoldi, F. Levy, V. Dutoit, M. Ayyoub, V. Rubio-Godoy, O. Michielin, P. Guillaume, P. Batard, I. F. Luescher, F. Lejeune, D. Lienard, N. Rufer, P. Y. Dietrich, D. E. Speiser, and J. C. Cerottini. 2002. Antigenicity and immunogenicity of Melan-A/MART-1 derived peptides as targets for tumor reactive CTL in human melanoma. *Immunol. Rev.* 188:81-96.

Salio, M., D. Shepherd, P. R. Dunbar, M. Palmowski, K. Murphy, L. Wu, and V. Cerundblo. 2001. Mature dendritic cells prime functionally superior melan-A-specific $CD8^+$ lymphocytes as compared with nonprofessional APC. *J. Immunol*, 167:1188-1197.

Sallusto, F., D. Lenig, R. Förster, M. Lipp, and A. Lanzavecchia. 1999. Two subsets of memory T lymphocytes with distinct homing potentials and effector functions. *Nature* 401:708-712.

Schuler, G., Schuler-Thurner, B., and Steinman, R. M. (2003). The use of dendritic cells in cancer immunotherapy. Curr. Opin. Immunol. 15, 138-147.

Steinman, R. M., Hawiger, D., and Nussenzweig, M. C. (2003). Tolerogenic dendritic cells. Annu. Rev. Immunol. 21, 685-711.

Stoitzner, P., C. H. Tripp, A. Eberhart, K. M. Price, J. Y. Jung, L. Bursch, F. Ronchese, and N. Romani. 2006. Langerhans cells cross-present antigen derived from skin. *Proc. Natl. Acad. Sci. U.S. A* 103:7783-7788.

Strehl, B., U. Seifert, E. Kruger, S. Heink, U. Kuckelkom, and P. M. Kloetzel. 2005. Interferon-gamma, the functional plasticity of the ubiquitin-proteasome system, and MHC class I antigen processing. *Immunol. Rev.* 207:19-30.

Valmori, D., U. Gileadi, C. Servis, P. R. Dunbar, J. C. Cerottini, P. Romero, V. Cerundolo, and F. Levy. 1999. Modulation of proteasomal activity required for the generation of a cytotoxic T lymphocyte-defined peptide derived from the tumor antigen MAGE-3. *J. Exp. Med.* 189:895-906.

Villadangos, J. A. and P. Schnorrer. 2007. Intrinsic and cooperative antigen-presenting functions of dendritic-cell subsets in vivo. *Nat. Rev. Immunol.* 7:543-555.

Yewdell, J. W. 2005. Immunoproteasomes: regulating the regulator. *Proc. Natl. Acad. Sci. U.S. A* 102:9089-9090.

Yewdell, J. W. and S. M. Haeryfar. 2005. Understanding presentation of viral antigens to CD8+ T cells in vivo: the key to rational vaccine design. *Annu. Rev. Immunol.* 23:651-682.

Zhong, G., Rels e Sousa, and Germain, R. N. (1997). Antigen-unspecific B cells and lymphoid dendritic cells both show extensive surface expression of processed antigen-major histocompatibility complex class II complexes after soluble protein exposure in vivo or in vitro. J. Exp. Med. 186, 673-682.

What is claimed is:

1. A method for cross-presentation of antigen to a $CD8^+$ $\alpha\beta$ T cell, comprising:
    obtaining an enriched $\gamma\delta$ T cell population from a population of human peripheral blood mononuclear cells;
    stimulating an antigen-presenting function in the enriched $\gamma\delta$ T cell population by exposing the enriched $\gamma\delta$ T cell population to a non-peptide stimulus effective for inducing an antigen-presenting function, said non-peptide stimulus being specifically presented to the enriched $\gamma\delta$ T cell population by a B cell population;
    obtaining a viable antigen-presenting $\gamma\delta$ T cell population by exposing the stimulated $\gamma\delta$ T cell population to a tumor- or microbial organism-derived antigen for uptake, processing, and presentation by the stimulated $\gamma\delta$ T cell population; and
    specifically presenting the tumor- or microbial organism-derived antigen to a population of $CD8^+$ $\alpha\beta$ T cells contained in a human blood cell population via the viable antigen-presenting $\gamma\delta$ T cell population.

2. The method of claim 1, wherein the population of human peripheral blood mononuclear cells is fractionated.

3. The method of claim 2, wherein the step of obtaining an enriched $\gamma\delta$ T cell population comprises subjecting the human peripheral blood mononuclear cells to at least one of differential centrifugation, magnetic cell sorting using antibodies to human V$\gamma$V$\delta$-T cell receptors, and selective expansion.

4. The method of claim 2, wherein the step of obtaining an enriched $\gamma\delta$ T cell population comprises exposing freshly isolated peripheral blood lymphocytes to structurally defined small molecular weight non-peptide compounds that induce a selective expansion of V$\gamma$9V$\delta$2$^+$-T cell receptor chain-expressing $\gamma\delta$ T cells.

5. The method of claim 4, wherein the structurally defined small molecular weight non-peptide compound is a prenyl-pyrophosphate, an alkyl-amine, or a metabolite of isoprenoid biosynthesis.

6. The method of claim 5, wherein the structurally defined small molecular weight non-peptide compound is selected from the group of compounds consisting of isopentenyl pyrophosphate (IPP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl -1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine, nitrogen containing bisphosphonates, and combinations thereof.

7. The method of claim 6, wherein the structurally defined small molecular weight non-peptide compound is isopentenyl pyrophosphate.

8. The method of claim 1, wherein the stimulus for induction of an antigen-presenting function is a structurally defined small molecular weight non-peptide compound selected from at least one of a prenyl-pyrophosphate, an alkyl-amine, or a metabolite of isoprenoid biosynthesis.

9. The method of claim 8, wherein the structurally defined small molecular weight non-peptide compound is selected from the group of compounds consisting of isopentenyl pyrophosphate (IPP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine, nitrogen containing bisphosphonates, and combinations thereof.

10. The method of claim 8, wherein the structurally defined small molecular weight non-peptide compound is at least one of isopentenyl pyrophosphate or 4-hydroxy-3-methyl-but-2-enyl pyrophosphate.

11. The method of claim 1, wherein the tumor- or microbial organism-derived antigen is derived from at least one of a tumor cell, a virus, a bacterium, a yeast, and a parasite;
further wherein the tumor- or microbial organism-derived antigen is presented to the stimulated γδ T cell population as a defined protein or peptide, as a nucleic acid encoding an antigenic portion of said defined protein or peptide, as an undefined protein or peptide mixture, as a crude or an enriched extract from a tumor, as a crude or an enriched extract from an infected cell, or as a combination thereof.

12. The method of claim 11, wherein the antigen is *Mycobacterium tuberculosis* purified protein derivative (PPD).

13. A method for treatment of a tumor or a chronic or recurrent infectious disease, comprising delivering an antigen-presenting autologous γδ T cell population prepared as set forth in claim 11 into a patient in need thereof;
wherein the antigen-presenting autologous γδ T cell population cross-presents an antigen derived from a tumor cell or from a chronic or recurrent infectious disease-causing microbial organism to a CD8+ αβ T cell of said patient.

14. The method of claim 13, wherein the autologous γδ T cell population derives said antigen for cross-presentation from a defined protein or peptide, from an undefined protein or peptide mixture, from a crude or an enriched extract from a tumor, from a crude or an enriched extract from an infected cell, or from a combination thereof.

15. The method of claim 13, wherein said step of delivering comprises single or repeated injections of said antigen-presenting autologous γδ T cell population intradermally, subcutaneously, intramuscularly, intravenously, mucosally or submucosally.

16. A method for cross-presentation of antigen to a CD8+ αβ T cell, comprising:
obtaining an enriched Vγ9Vδ2+-T cell receptor chain-expressing γδ T cell population from a population of human peripheral blood mononuclear cells;
stimulating an antigen-presenting function in the enriched Vγ9Vδ2+-T cell receptor chain-expressing γδ T cell population by exposing the enriched Vγ9Vδ2+-T cell receptor chain-expressing γδ T cell population to a nitrogen containing bisphosphonate effective for inducing an antigen-presenting function, the nitrogen containing bisphosphonate being specifically presented to the enriched Vγ9Vδ2+-T cell receptor chain-expressing γδ T cell population by a B cell population;
obtaining a viable antigen-presenting Vγ9Vδ2+-T cell receptor chain-expressing γδ T cell population by exposing the stimulated Vγ9Vδ2+-T cell receptor chain-expressing γδ T cell population to a tumor- or microbial organism-derived antigen for uptake, processing, and presentation by the stimulated Vγ9Vδ2+-T cell receptor chain-expressing γδ T cell population; and
specifically presenting the tumor- or microbial organism-derived antigen to a population of CD8+ αβ T cells contained in a human blood cell population via the viable antigen-presenting Vγ9Vδ2+-T cell receptor chain-expressing γδ T cell population.

17. The method of claim 16, wherein the tumor- or microbial organism-derived antigen is derived from at least one of a tumor cell, a virus, a bacterium, a yeast, and a parasite;
further wherein the tumor- or microbial organism-derived antigen is presented to the stimulated γδ T cell population as a defined protein or peptide, as a nucleic acid encoding an antigenic portion of said defined protein or peptide, as an undefined protein or peptide mixture, as a crude or an enriched extract from a tumor, as a crude or an enriched extract from an infected cell, or as a combination thereof.

18. A method for preparing a peptide-specific effector T cell, comprising:
obtaining an enriched Vγ9Vδ2+-T cell receptor chain-expressing γδ T cell population from a population of human peripheral blood mononuclear cells;
stimulating an antigen-presenting function in the enriched Vγ9Vδ2+-T cell receptor chain-expressing γδ T cell population by exposing the enriched Vγ9Vδ2+-T cell receptor chain-expressing γδ T cell population to a nitrogen containing bisphosphonate effective for inducing an antigen-presenting function, the nitrogen containing bisphosphonate being specifically presented to the enriched Vγ9Vδ2+-T cell receptor chain-expressing γδ T cell population by a B cell population;
obtaining a viable antigen-presenting Vγ9Vδ2+-T cell receptor chain-expressing γδ T cell population by exposing the stimulated Vγ9Vδ2+-T cell receptor chain-expressing γδ T cell population to a tumor- or microbial organism-derived soluble peptide antigen for uptake, processing, and presentation by the stimulated Vγ9Vδ2+-T cell receptor chain-expressing γδ T cell population; and
obtaining a peptide-specific effector T cell by specifically presenting the tumor- or microbial organism-derived soluble peptide antigen to a population of CD8+ αβ T cells via the viable antigen-presenting Vγ9Vδ2+-T cell receptor chain-expressing γδ T cell population.

19. The method of claim 18, wherein the soluble peptide antigen is derived from at least one of a tumor cell, a virus, a bacterium, a yeast, and a parasite.

20. The method of claim 19, wherein the soluble peptide antigen is derived from the group consisting of a defined protein or peptide, an undefined protein or peptide mixture, a crude or an enriched extract from a tumor, a crude or an enriched extract from an infected cell, and a combination thereof.

* * * * *